US012759987B2

(12) United States Patent
Chan et al.

(10) Patent No.: US 12,759,987 B2
(45) Date of Patent: Oct. 13, 2026

(54) CARDIAC THERAPEUTIC

(71) Applicant: National University of Singapore, Singapore (SG)

(72) Inventors: Chun Yong Eric Chan, Singapore (SG); Aneesh Vidyadhar Karkhanis, Singapore (SG); Gopalakrishnan Venkatesan, Singapore (SG)

(73) Assignee: National University of Singapore, Singapore (SG)

(*) Notice: Subject to any disclaimer, the term of this patent is extended or adjusted under 35 U.S.C. 154(b) by 794 days.

(21) Appl. No.: 17/625,421

(22) PCT Filed: Jul. 8, 2020

(86) PCT No.: PCT/SG2020/050389

§ 371 (c)(1),
(2) Date: Jan. 7, 2022

(87) PCT Pub. No.: WO2021/006817

PCT Pub. Date: Jan. 14, 2021

(65) Prior Publication Data

US 2022/0267288 A1 Aug. 25, 2022

(30) Foreign Application Priority Data

Jul. 8, 2019 (GB) .................................... 1909732
Feb. 3, 2020 (GB) .................................... 2001434

(51) Int. Cl.
*A61P 9/06* (2006.01)
*A61P 7/02* (2006.01)
*A61P 9/00* (2006.01)
*C07D 307/80* (2006.01)

(52) U.S. Cl.
CPC .............. *C07D 307/80* (2013.01); *A61P 9/06* (2018.01); *C07B 2200/05* (2013.01)

(58) Field of Classification Search
CPC .. C07D 307/80; A61P 9/06; A61P 7/02; A61P 9/00; C07B 2200/05
See application file for complete search history.

(56) References Cited

U.S. PATENT DOCUMENTS 9,505,667 B2 * 11/2016 Howard, Jr. ......... C07D 487/04
2009/0076137 A1 * 3/2009 Czarnik .................... A61P 9/06 549/467
2013/0274325 A1 10/2013 Duggan et al.

OTHER PUBLICATIONS

GB 1909732.8 Search Report mailed on Dec. 18, 2019 (5 pages).
PCT/SG2020/050389 International Search Report and Written Opinion mailed on Aug. 25, 2020 (16 pages).
Kambayashi et al., "How the Deuteration of Dronedarone Can Modify Its Cardiovascular Profile: In Vivo Characterization of Electropharmacological Effects of Poyendarone, a Deuterated Analogue of Dronedarone," *Cardiovasc Toxicol*. 20:339-350, 2020.
McDonald et al., "Warfarin-Amiodarone Drug-Drug Interactions: Determination of $[I]_u/K_{I,u}$, for Amiodarone and Its Plasma Metabolites," *Clin Pharmacol Ther*. 91:709-717, 2012.
Schofield et al., "Effect of deuteration on the metabolism and clearance of some pharmacologically active compounds—synthesis and in vitro metabolism of deuterated derivatives of dronedadron," *J Labelled Comp Radiopharm*. 56:504-512, 2013.
Karkhanis, et al., "Site-directed deuteration of dronedarone preserves cytochrome P4502J2 activity and mitigates its cardiac adverse effects in canine arrhythmic hearts," *Acta Pharmaceutica Sinica B* 12(10): pp. 3905-3923, Oct. 2022.
Atzrodt, Jens, et al., "The renaissance of H/D exchange," *Angewandte Chemie International Edition* 46(41): pp. 7744-7765, Oct. 2007.
Barefield, et al., "Catalysis of aromatic hydrogen-deuterium exchange by metal hydrides," *Journal of the American Chemical Society* 92(17): pp. 5234, Aug. 1970.
Benson, "Bond Energies," *Journal of Chemical Education* 42(9): pp. 502-518, Sep. 1965.
Boix, et al., "Efficient HD exchange of aromatic compounds in near-critical D2O catalysed by a polymer-supported sulphonic acid," *Tetrahedron letters* 40(23): pp. 4433-4436, Jun. 1999.
Cottrell, "Strengths of Chemical Bonds," 1954.
Dean, "Lange's Handbook of Chemistry," McGraw-Hill, Inc., 1999.
Garnett, et al., "Homogeneous Metal-Catalyzed Exchange of Aromatic Compounds. A New General Isotopic Hydrogen Labeling Procedure," *Journal of the American Chemical Society* 89(17): pp. 4546, Aug. 1967.
IItian Academy, "CIE AS/A Level Chemistry 37.4 Proton 1H NMR spectroscopy Study Notes—2025-2027 Syllabus," https://www.iitianacademy.com/a-level/cie-as-a-level-chemistry-9701-revisionresources/37-4-proton-1h-nmr-spectroscopy-study-notes/?utm_source.
Kerr, "Bond dissociation energies by kinetic methods," *Chemical Reviews* 66(5): 465-500, Sep. 1966.
Kuang, et al., "Visible light driven deuteration of formyl C-H and hydridic C (sp 3)-H bonds in feedstock chemicals and pharmaceutical molecules," *Chemical science* 11(33): pp. 8912-8918, Aug. 2020.
Oae, et al., "Acid-catalyzed Hydrogen-Deuterium Exchange Reactions of Deuterated Anisole, Thioanisole and Benzene," *Bulletin of the Chemical Society of Japan* 35(4): pp. 681-683, 1962.

(Continued)

*Primary Examiner* — Kortney L. Klinkel
*Assistant Examiner* — Alison Azar Hastings
(74) *Attorney, Agent, or Firm* — Klarquist Sparkman, LLP

(57) ABSTRACT

The invention concerns a novel cardiac therapeutic effective against atrial fibrillation (AF); a pharmaceutical composition comprising same; the use of same to treat cardiac disease; and a method of treating cardiac disease involving the use of same.

12 Claims, 51 Drawing Sheets

Figure 1A:
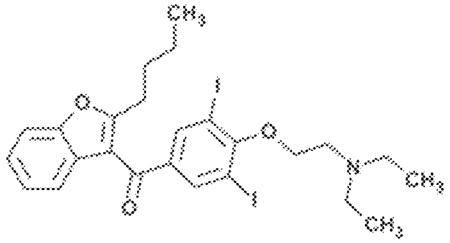

Specification includes a Sequence Listing.

(56) References Cited

OTHER PUBLICATIONS

OpenOChem, “Exchangeable Protons and Deuterium Exchange,” https:/learn.openochem.org/learn/nmr-ir-uv-and-ms/hnmr/exchangeable-protons-and-deuterium-exchange?utm_source.

Sajiki, et al., “Aromatic ring favorable and efficient H-D exchange reaction catalyzed by Pt/C,” *Tetrahedron letters* 46(41): pp. 6995-6998, Oct. 2005.

* cited by examiner

AA
5,6-EET
8,9-EET
11,12-EET
14,15-EET
5,6-DHET
8,9-DHET
11,12-DHET
14,15-DHET

D1
D2
D3
D4
D5
D6
D7
D8 ln (% 2J2 activity remaining)
4.0
3.0
2.0
0
10
20
30
40
Preincubation time (min)
Vehicle
0.1 μM
2 μM
5 μM
10 μM
20 μM $k_{obs}$ (min$^{-1}$)
0.04
0.03
0.02
0.01
0.00
0
5
10
15
20
25
[Dronedarone] (μM)

ln (% 2J2 activity remaining)
4.0
3.0
2.0
0
10
20
30
40
Preincubation time (min)
Vehicle
0.1 μM
2 μM
5 μM
10 μM
20 μM $k_{obs}$ (min$^{-1}$)
0.015
0.010
0.005
0.000
0
5
10
15
20
25
[Poyendarone] (μM)

-120 mV
-20
DMSO
DMSO 11 min

-120 mV
-20
DMSO
6 uM poyendarone 11 min

Baseline
% remaining Nav1.5 peak current
100
50
0
0
2
4
6
8
10
12
Time (min)
DMSO
1 uM poyendarone
3 uM poyendarone
6 uM poyendarone
10 uM poyendarone % inhibition of peak $I_{Nav1.5}$
100
80
60
40
20
0
-6.50
-6.00
-5.50
-5.00
-4.50
log [M]
IC50 = 5.514 μM
HillSlope = 4.046 ± 2.720

-80 mV
0
DMSO
DMSO 10 min

-80 mV
0
DMSO
5 uM amiodarone

Baseline
% remaining Cav1.2 peak current
100
50
0
0
5
10
Time (min)
DMSO
1 uM amiodarone
2 uM amiodarone
5 uM amiodarone
10 uM amiodarone % inhibition of peak ICav1.2
100
80
60
40
20
0
-7.00
-6.00
-5.00
-4.00
log [M]
IC50 = undetermined
HillSlope = undetermined 20
-80 mV
-50
-80
DMSO
0.2 uM amiodarone Baseline
% remaining KCNH2 peak current
100
50
0
0
5
10
15
Time (min)
10 nM amiodarone
0.1 uM amiodarone
0.2 uM amiodarone
1 uM amiodarone % inhibition of peak KCNH2 current
100
80
60
40
20
0
-9.00
-8.00
-7.00
-6.00
-5.00
log [M]
IC50 = 0.164 μM
HillSlope = 3.475 ± 1.357

Plasma concentration (µg/mL)
Time (h)
Dronedarone
Clinical data
95th percentile (top)
5th percentile (bottom)
Poyendarone

B

Plasma concentration (µg/mL)
0.04
0.03
0.02
0.01
0.00
Time (h)
0
96
192
288
384
480
300
350
400

CARDIAC THERAPEUTIC

CROSS REFERENCE TO RELATED APPLICATIONS

This is the U.S. National Stage of International Application No. PCT/SG2020/050389, filed Jul. 8, 2020, which was published in English under PCT Article 21(2), which in turn claims the benefit of Great Britain Application No. 1909732.8, filed Jul. 8, 2019, and Great Britain Application No. 2001434.6, filed Feb. 3, 2020.

FIELD OF THE INVENTION

The invention concerns a novel cardiac therapeutic effective against atrial fibrillation (AF), stroke and thromboembolism; a pharmaceutical composition comprising same; the use of same to treat cardiac disease; and a method of treating cardiac disease involving the use of same.

BACKGROUND OF THE INVENTION

Atrial fibrillation (AF) is the most common sustained arrhythmia with a global increase in prevalence due to ageing populations. AF affects about 2.3 million people in North America and 4.5 million people in the European Union. AF causes more than 750,000 hospitalisations and an estimated 130,000 deaths per year in the US. AF results in 5-fold increase in stroke and thromboembolism and 2-fold increase in mortality. Global AF market is estimated to be at $16 billion by 2020. To date, pharmacotherapy remains clinically important.

AF is characterized by an irregular and rapid heart rate that may occur without any prior cardiac complications (lone AF, 3%) or be associated with underlying cardiac diseases such as congestive heart failure, coronary artery disease, hypertension, diabetes or atherosclerosis.

Amiodarone (FIG. 1A) and dronedarone (FIG. 1B) are benzofuran derived multiple cardiac ion channel blockers and FDA-approved antiarrhythmic drugs.

Amiodarone is used to treat 45% of AF cases, but has severe adverse effects including thyroid toxicity, lung inflammation, interstitial pneumonitis and lung fibrosis. While dronedarone circumvents the thyroid and pulmonary toxicities associated with amiodarone, clinical trials have reported dronedarone's higher risk of death compared to placebo, resulting in a boxed warning against its use in patients with NYHA Class IV heart failure, NYHA Class II-III heart failure with a recent decompensation or permanent AF. Surgical treatment through catheter ablation is an alternative option but is relatively low in success rate (28% for first procedure), expensive and inaccessible by patients in selected countries.

Human cardiac CYP2J2 metabolizes arachidonic acid (AA) to epoxyeicosatrienoic acids (EETs) which have been implicated in heart rhythm control.

We have surreptitiously discovered a critical correlation between the potent, covalent inactivation of cardiac CYP2J2, by a reactive metabolite benzofuran derivatives such as dronedarone, and beat-to-beat variability (BBV) of cardiomyocytes. Our observations were measured in human induced pluripotent stem cells-derived cardiomyocytes (hiPSC-CM).

With this information we have developed a novel, site-directed deuterated analogue of dronedarone, termed herein poyendarone.

The deuteration process involves an atomic scale modification to the target compound, exchanging hydrogen (a proton with an orbiting electron) for deuterium (a protein and neutron with an orbiting electron). In pharmacology, deuteration is often applied to stabilise a drug compound metabolically to improve its pharmacokinetics. In this work, deuteration was used to modify the chemical reactivity of an electrophilic intermediate of dronedarone to avoid the inhibition of CYP2J2 and so improve its safety profile by mitigating a critical off-target cardiac adverse effect. Counterintuitively, the pharmacokinetics of dronedarone are preserved in poyendarone by avoiding random deuteration.

Advantageously, targeted deuteration results in the production of a molecule, poyendarone, that has the same favourable pharmacokinetics and anti-atrial fibrillatory effect as its non-deuterated analogue (i.e. dronedarone) but with a highly desirable reduction in proarrhythmic risk. Consistent, with this finding we have also discovered poyendarone does not inactivate recombinant CYP2J2 enzyme nor does it inactivate CYP2J2 in a human cell model i.e. hiPSC-CM, that is to say, unlike dronedarone it does not give rise to BBV in hiPSC-CM. Furthermore, we have discovered poyendarone, when tested in vivo, gives rise to similar pharmacokinetics and cardiohemodynamic profiles as dronedarone and it demonstrates anti-atrial fibrillatory potential yet negligible ventricular proarrhythmic, compared to dronedarone.

In summary, we have developed a novel small molecule therapeutic, typically for treating cardiac arrhythmia, that has the favourable pharmacokinetics and antiarrhythmic pharmacology of FDA-approved benzofuran derived drugs such as dronedarone, but does not possess significant ventricular proarrhythmic toxicology. Further, when used in man, poyendarone is expected to have minimal organ toxicity when compared with amiodarone, thus rendering it protective of at least the thyroid and lungs.

STATEMENTS OF INVENTION

According to a first aspect of the invention there is provided a compound according to Formula (I) or a pharmaceutically acceptable salt thereof:

Formula (I)

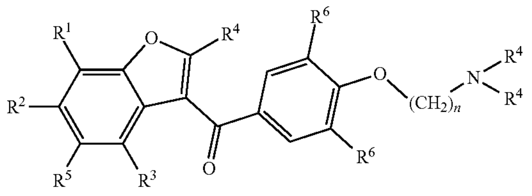

wherein:

$R^1$, $R^2$ and $R^3$ each represents deuterium;

n represents 2 or 3;

each $R^4$ independently represents a $C_{1-6}$ hydrocarbyl group which may be substituted with one or more of nitro, halogen, amino, amido, cyano, carboxyl, sulphonyl, hydroxyl, ketone and aldehyde groups;

$R^5$ represents hydrogen or

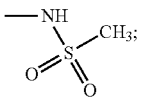

and each $R^6$ independently represents hydrogen or halogen; provided that each atom not designated as deuterium is present at its natural isotopic abundance, and each position designated as deuterium has at least 45% incorporation of deuterium.

The compounds of the present invention have been shown not only to retain the same favourable pharmacokinetics and anti-atrial fibrillatory effect as their non-deuterated analogues (e.g. dronedarone), but they have also been shown to possess a lower ventricular proarrhythmic toxicology.

In the compounds of this invention any atom not specifically designated as a particular isotope is present at its natural isotopic abundance. For example, unless otherwise stated, when a position is designated specifically as "H" or "hydrogen", the position is understood to have hydrogen present at its natural abundance isotopic composition. Also unless otherwise stated, when a position is designated specifically as "deuterium", the position is understood to have the deuterium ($^2H$) isotope at an abundance that is at least 3000 times greater than the natural abundance of deuterium, which is 0.015% (i.e. at least 45% incorporation of deuterium is required).

In the compounds of the present invention, the amount of deuterium present in each of three specific sites $R^1$, $R^2$ and $R^3$ is elevated above its natural isotopic abundance. Preferably, each position designated as deuterium (i.e. $R^1$, $R^2$ and $R^3$) has at least 90% (i.e. at least 6000 times greater than the natural abundance of deuterium), still more preferably at least 95% and most preferably 100% incorporation of deuterium.

As used herein, all percentages expressed in relation to the abundance of deuterium within the compounds of the invention are mole percentages.

Deuteration can be achieved either by exchanging protons with deuterium within a non-deuterated analogue or by synthesizing the compound using deuterated starting materials.

In the compounds of the invention, each $R^4$ independently represents a $C_{1-6}$ hydrocarbyl group which may be substituted with one or more of nitro, halogen, amino, amido, cyano, carboxyl, sulphonyl, hydroxyl, ketone or aldehyde groups. As used herein, the expression 'hydrocarbyl' refers to a group made up of carbon and hydrogen atoms. These include aliphatic (i.e. alkyl, alkenyl or alkynyl) groups, as well as aromatic groups such as phenyl or combinations of these. Aliphatic groups may be straight or branched chains, or they may form or include non-aromatic ring structures. As is readily appreciated, terms such as '$C_{1-6}$ hydrocarbyl' have a similar meaning with the additional requirement that any such functional group comprises a total of 1 to 6 carbon atoms.

As used herein, the term halogen refers to a fluoro, chloro, bromo or iodo group.

In preferred embodiments, each $R^4$ independently represents an unsubstituted $C_{1-6}$ hydrocarbyl group, more preferably an unsubstituted $C_{2-4}$ hydrocarbyl group. In particularly preferred embodiments, said hydrocarbyl group is an alkyl group. In particularly preferred embodiments, each $R^4$ is a $C_4$ alkyl group, and is typically n-butyl.

In the compounds of the invention, $R^5$ may represent hydrogen or

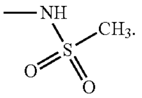

However, $R^5$ preferably represents

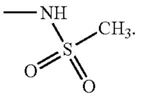

Similarly, each $R^6$ may represent hydrogen or a halogen group, typically iodine. However, in preferred embodiments, each $R^6$ is hydrogen. The exclusion of halogen atoms (at $R^6$) results in a compound devoid of lung and thyroid toxicities, and the inclusion of such a methanesulphonamide group (at $R^5$) modifies the lipophilicity of the compound, resulting in lower tissue accumulation and systemic toxicity.

In the compounds of the invention, n is preferably 3.

Particularly suitable compounds of the invention are those according to Formula (II), wherein $R^1$, $R^2$ and $R^3$ are as defined above.

Formula (II)

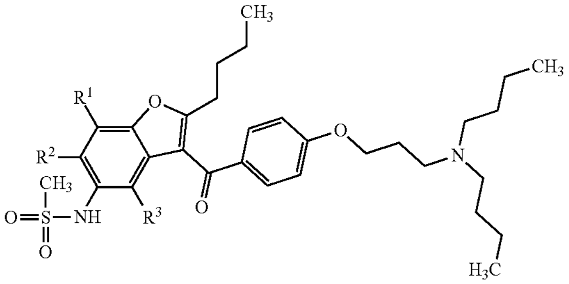

As discussed above, the compounds of the present invention are suitable for use in the treatment of cardiac arrhythmia, in particular atrial fibrillation. Further, and in contrast to non-deuterated analogues, these compounds possess a negligible ventricular proarrhythmic toxicology.

Therefore, in a second aspect of the invention there is provided a compound according the first aspect of the invention for use in medicine.

Also provided is a compound according to the first aspect of the invention for use in the treatment of cardiac disease. In preferred embodiments, the cardiac disease is a cardiac arrhythmia, and in particularly preferred embodiments is atrial fibrillation.

In a third aspect, the invention provides a method for the treatment of cardiac disease, the method comprising administering to a patient in need of such a treatment a therapeutically effective amount of a compound according to the first aspect of the invention.

In some cases, the cardiac disease to be treated is a cardiac arrhythmia and is preferably atrial fibrillation.

The compounds of the present invention will usually be administered in a pharmaceutical composition and therefore in a further aspect of the invention there is provided a pharmaceutical composition comprising a compound of the first aspect of the invention and a pharmaceutically acceptable excipient or carrier.

The composition may be administered by any appropriate route, for example oral, buccal, nasal, transdermal or parenteral, for example intravenous or intramuscular. Preferably the composition is for oral administration.

Formulations of the present invention for oral administration invention may be presented as: discrete units such as capsules, sachets, tablets, troches or lozenges each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a syrup or elixir; or as a bolus, etc.

For compositions for oral administration (e.g. tablets, capsules, formulations comprising a mucoadherent etc.), the term "acceptable carrier" includes vehicles such as common excipients e.g. binding agents, for example syrup, acacia, gelatin, sorbitol, tragacanth, polyvinylpyrrolidone (povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; wetting agents/surfactants such as poloxamers, polysorbates, sodium docusate and sodium lauryl sulfate; disintegrants such as starch or sodium starch glycolate; and lubricants such as magnesium stearate, sodium stearate and other metallic stearates, glycerol stearate, stearic acid, silicone fluid, talc waxes, oils and colloidal silica. Sweetening agents and flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Some formulations may comprise a mucoadherent, for example a mucopolysaccharide such as sodium hyaluronate. Such compositions may be formulated as, for example, liquids, liquid syrups, soft gels, liquid gels, flowable gels or aqueous suspensions and may, in addition to the active agent and the mucoadherent, also contain one or more additional excipients as set out above. Liquid formulations will usually also contain a liquid carrier, which may be a solvent or suspending agent, for example water or saline solution and may also contain a substance to increase their viscosity, for example sodium carboxymethylcellulose, sorbitol or dextran.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Parenteral formulations will generally be sterile

In a fourth aspect of the invention, there is provided a compound according to Formula (III) or a pharmaceutically acceptable salt thereof:

Formula (III)

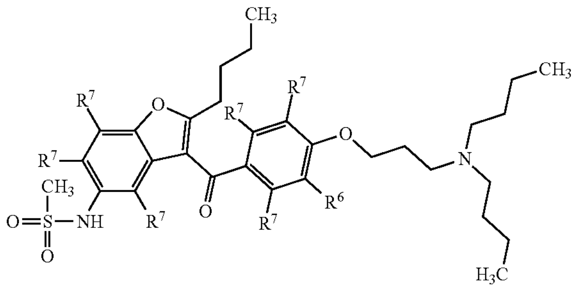

wherein each $R^7$ represents deuterium.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Figure 1B:
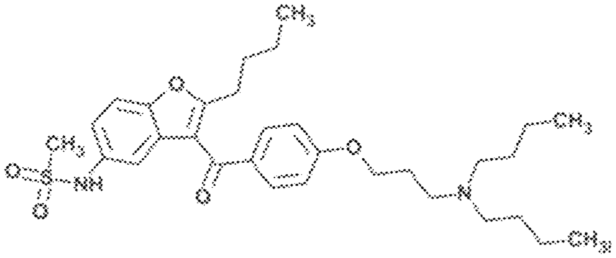

The Invention will now be described by way of example only with reference to the Examples below and to the following Figures wherein:

FIGS. 1A-1B. Show chemical structures of benzofuran-derived and FDA approved antiarrhythmic drugs (FIG. 1A) amiodarone and (FIG. 1B) dronedarone. Dronedarone is devoid of iodine atoms but has methanesulphonamide group. In addition, dronedarone comprises an N-dibutylamine moiety whereas amiodarone comprises an N-diethylamine moiety. Further, dronedarone comprises a propoxy ($-O-CH_2-CH_2-CH_2-$) linker between the N-dibutylamine moiety and phenyl group whereas amiodarone comprises an ethoxy (—O—$CH_2$—$CH_2$—) linker between the N-diethylamine moiety and phenyl group.

Figure 2:
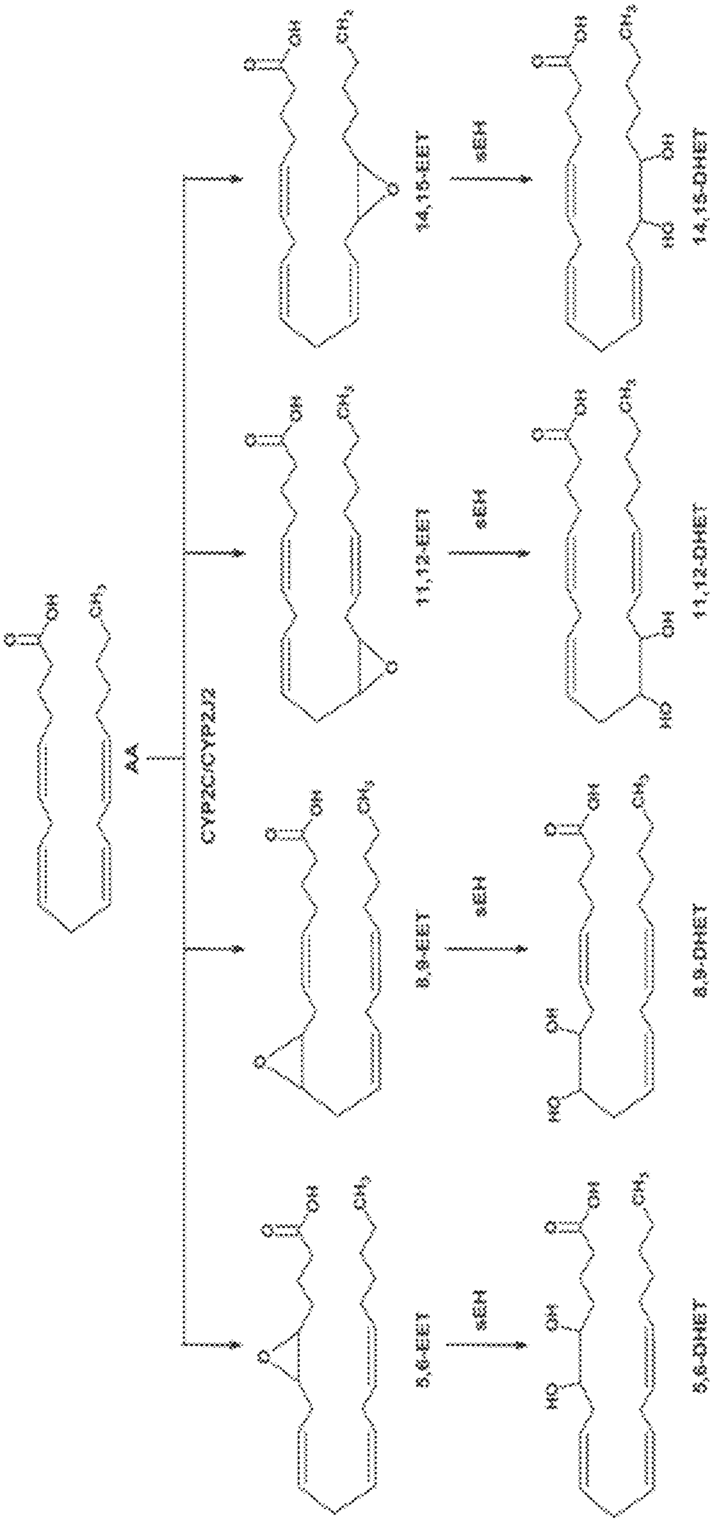

FIG. 2. Shows CYP450-mediated AA metabolism pathway. AA is metabolised to regioisomeric EETs by CYP2J2. EETs get metabolised further to DHETs by sEH.

Figure 3:
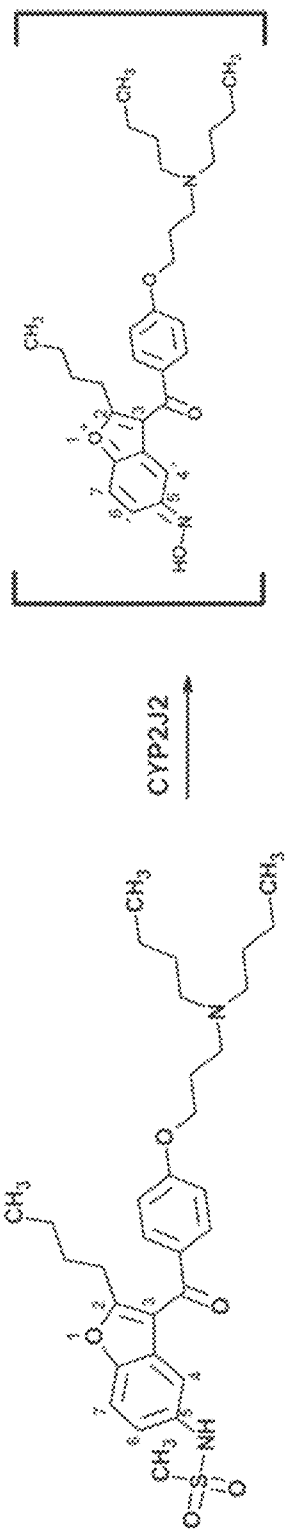

FIG. 3. Shows metabolism of dronedarone to quinone-oxime reactive metabolite by CYP2J2. The electrophilic sites on the reactive metabolite are shown in asterisks (positions 4 and 6).

Figure 4:
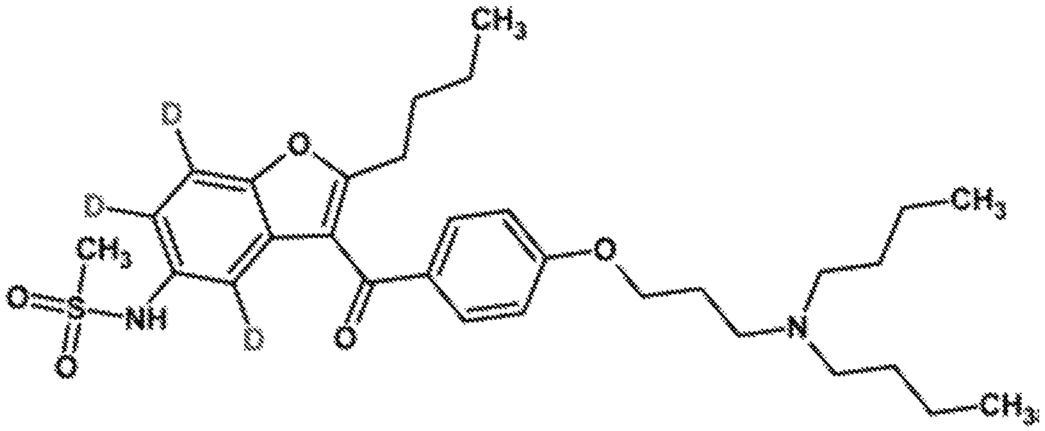

FIG. 4. Shows the chemical structure of the deuterated benzofuran derivative poyendarone. 'D' denotes the presence of the deuterium isotope.

Figure 5:
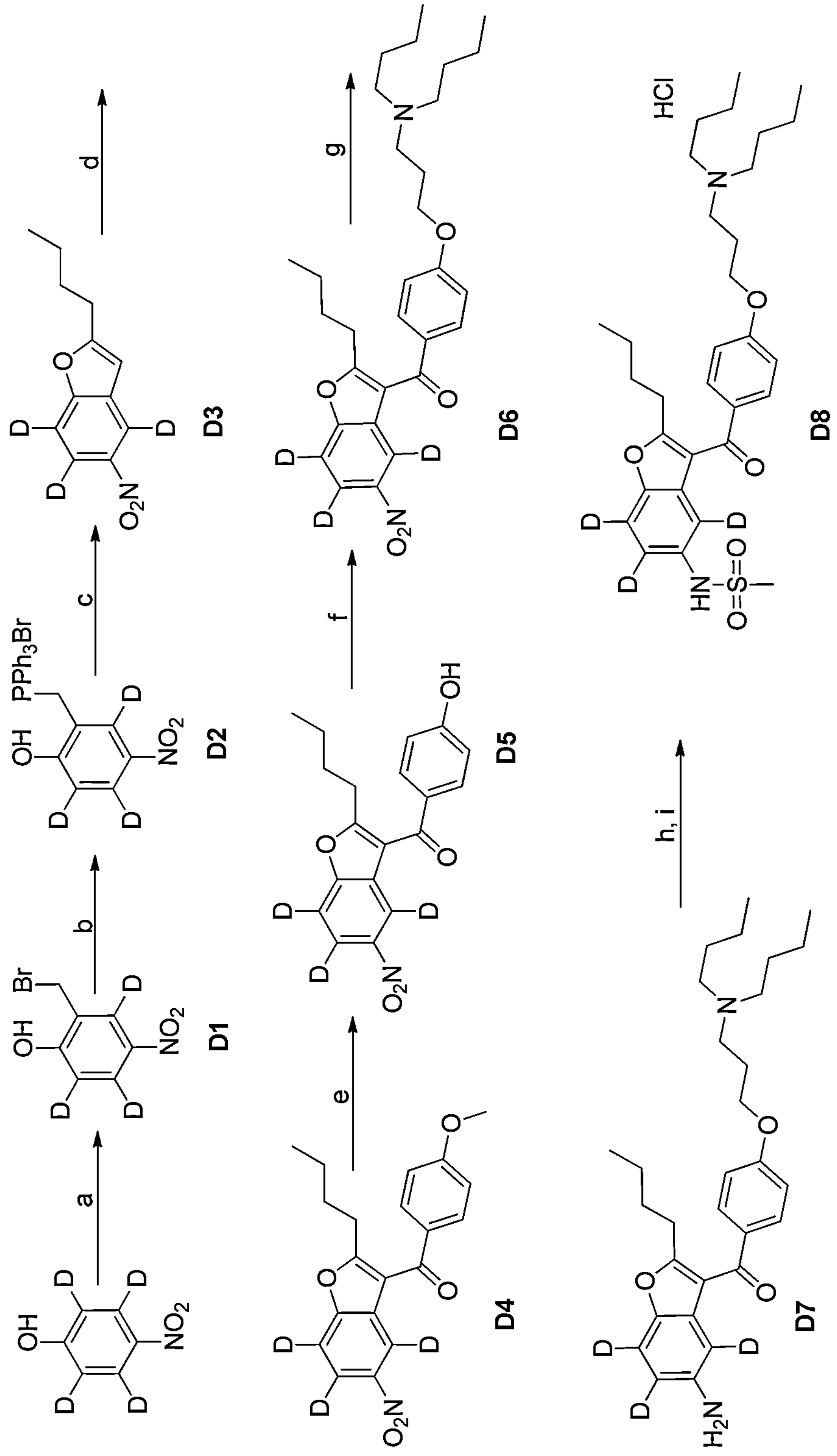

FIG. 5. Shows the synthesis of the hydrochloride salt of the deuterated benzofuran derivative poyendarone ('poyendarone HCl'). 'D' denotes the presence of the deuterium isotope. Reagents and conditions: (a) conc. $H_2SO_4$, 48% HBr, 35% HCHO, 75° C., 6 h. D1 yield: 76.5%; (b) toluene, $PPh_3$, reflux, 1 h. D2 yield: 99.0%; (c) $CHCl_3$, pyridine, valeroyl chloride, reflux 2h; toluene, triethylamine, reflux, 3h. D3 yield: 73.5%; (d) dichloromethane, $C_6H_5COCl$(p-$OCH_3$), $SnCl_4$, rt, 24 h. D4 yield: 93.5%; (e) dichloromethane, $AlCl_3$, reflux, 24h. D5 yield: 98.0%; (f) acetone, anhyd.$K_2CO_3$, 1-chloro-3-di-n-butylaminopropane, reflux, overnight. D6 yield: 77.0%; (g) Fe, EtOH, $H_2O$, conc. HCl, 65° C., 3h. D7 yield: 80.3%; (h) dichloromethane, pyridine, $CH_3SO_2Cl$, 35° C., 3h; (i) methanol, hydrochloric acid, 0° C., 3 h. D8 yield: 79.0%.

Figure 6:
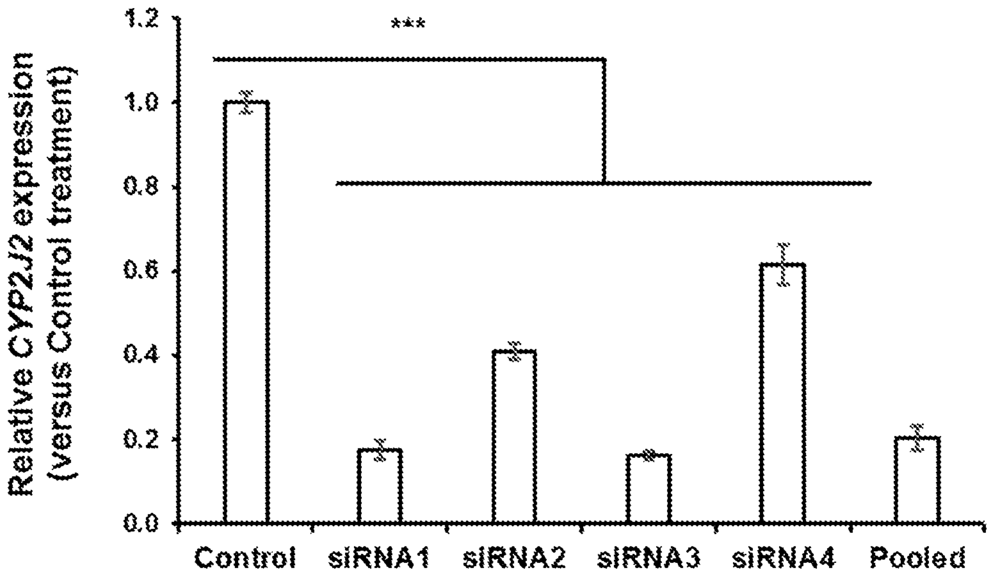

FIG. 6. Shows a representative plot on the effects of each CYP2J2 siRNA treatment condition on CYP2J2 gene expression. qPCR was done 96 h post siRNA transfection, after their calcium transients were captured on video. Across all siRNA treatments, there is a 40-80% knockdown of CYP2J2 (***, p<0.001, N=3).

Figure 7:
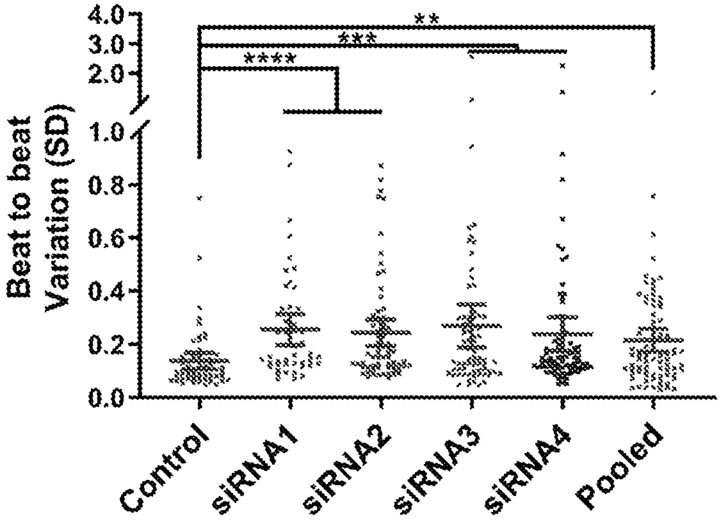

FIG. 7. Shows the effect of each CYP2J2 siRNA treatment condition on the beat to beat variation measured in standard deviations experienced by individual clusters of cardiomyocytes across biological replicates. Each point represents the beat to beat variation of an individual cluster of cardiomyocytes measured during a 30 second window. The mean and 95% confidence interval is plotted. Number of individual clusters measured: Control, 60; siRNA1, 48; siRNA2, 66; siRNA3, 72; siRNA4, 86; Pooled, 81. Nonparametric Mann-Whitney U test was used to assess significance as the distribution of the data is not normal, determined using Shapiro-Wilk normality test (, p<0.01; *, p<0.001; ****, p<0.0001).

Figure 8:
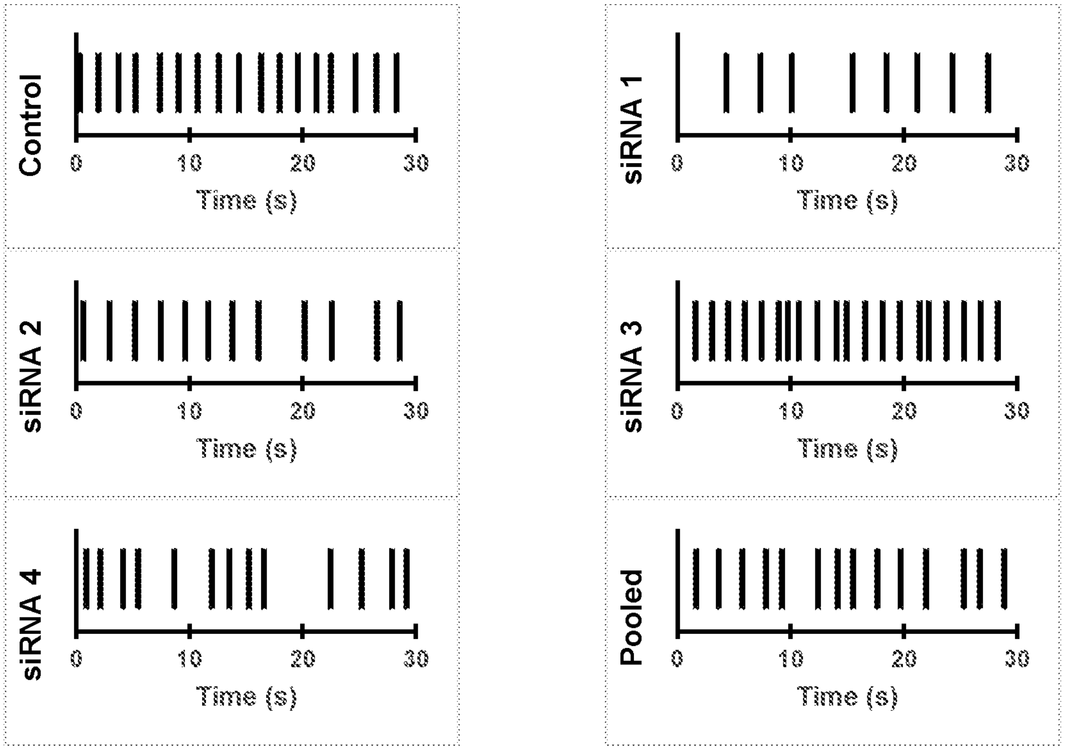

FIG. 8. Shows representative raster plots of individual clusters of cardiomyocytes of each treatment condition. Each line represents a contraction occurrence along the time axis within 30 seconds. Regularity of contraction can be visually confirmed in these graphs and quantified using standard deviations between contraction occurrences.

Figure 9:
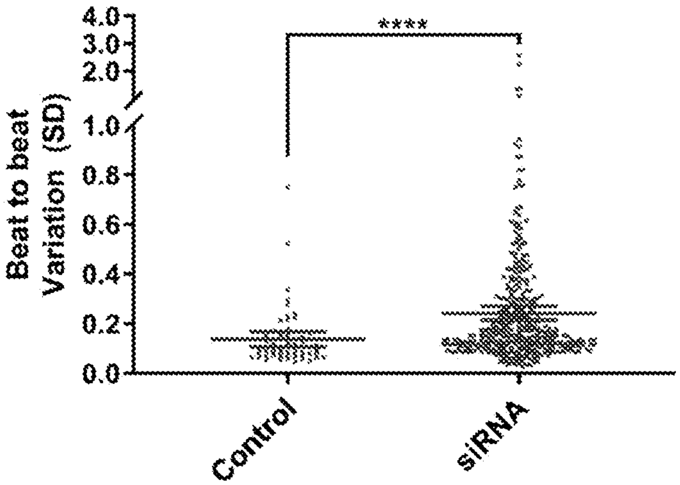

FIG. 9. Shows the effect of CYP2J2 siRNA treatment on the beat to beat variation measured in standard deviations experienced by individual clusters of cardiomyocytes across biological replicates. Each point represents the beat to beat variation of an individual cluster of cardiomyocytes measured during a 30 second window. The mean and 95% confidence interval is plotted. Number of individual clusters measured: Control, 60; siRNA (includes all four individual treatment conditions and the pooled condition), 353. Nonparametric Mann-Whitney U test was used to assess significance as the distribution of the data is not normal, determined using Shapiro-Wilk normality test (****, p<0.0001).

Figure 10A:
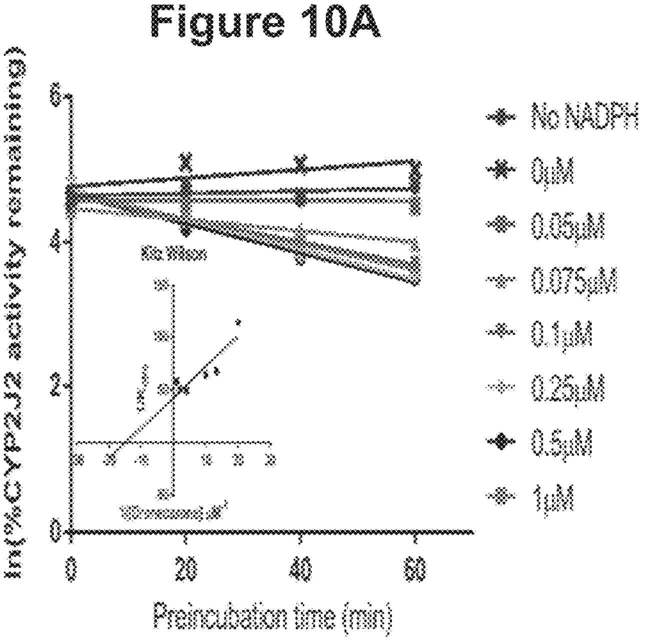
Figure 10B:
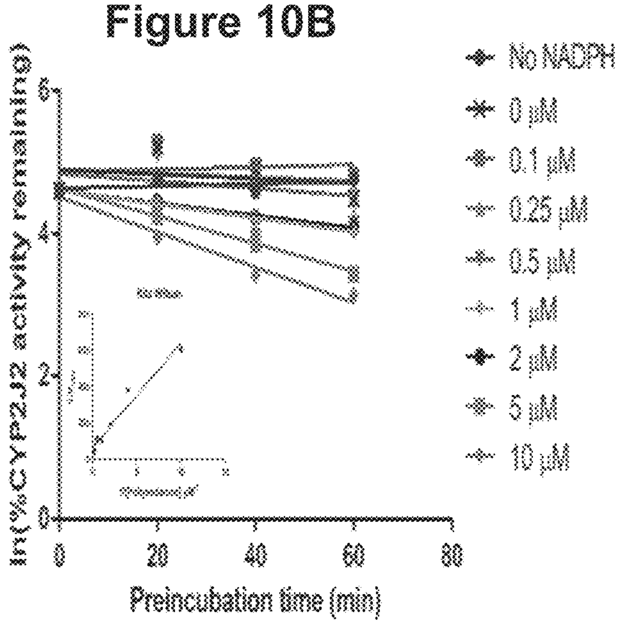

FIGS. 10A-10B. Show time-, concentration-, NADPH-dependent inactivation of CYP2J2 using astemizole as the probe substrate. The figures show[[s]] that in the absence of the inhibitor (0 μM drug) or NADPH (no NADPH), CYP2J2 is not inactivated. However, in the presence of the inhibitor and NADPH, there is concentration-dependent decrease in CYP2J2 activity. The logarithm of percentage CYP2J2 activity was plotted against pre-incubation time in the presence of (FIG. 10A) dronedarone and (FIG. 10B) poyendarone. The reciprocal of the observed inactivation rate ($k_{obs}$) was plotted against the reciprocal of inhibitor concentration to form Kitz-Wilson plot to calculate kinact/KI. The higher the kinact/KI ratio, the greater is the potency of MBI of CYP2J2. Each point represents mean and S.D of three experiments.

FIGS. 11A-11D. Show Time- and concentration-dependent inactivation of CYP2J2 by (FIG. 11A) dronedarone and (FIG. 11C) poyendarone using rivaroxaban as the probe substrate. The observed inactivation rates ($k_{obs}$) was used to calculate the inactivation kinetic constants $K_I$ and $k_{inact}$ for (FIG. 11B) dronedarone and (FIG. 11D) poyendarone using nonlinear regression.

FIGS. 12A-12D. Show Time- and concentration-dependent inactivation of CYP2J2 by (A) Compound 2 of Table 3 and (C) Compound 3 of Table 3 using rivaroxaban as the probe substrate. The observed inactivation rates ($k_{obs}$) was used to calculate the inactivation kinetic constants $K_{and}$ $k_{inact}$ for (B) Compound 2 and (D) Compound 3 using nonlinear regression.

Figure 13A:
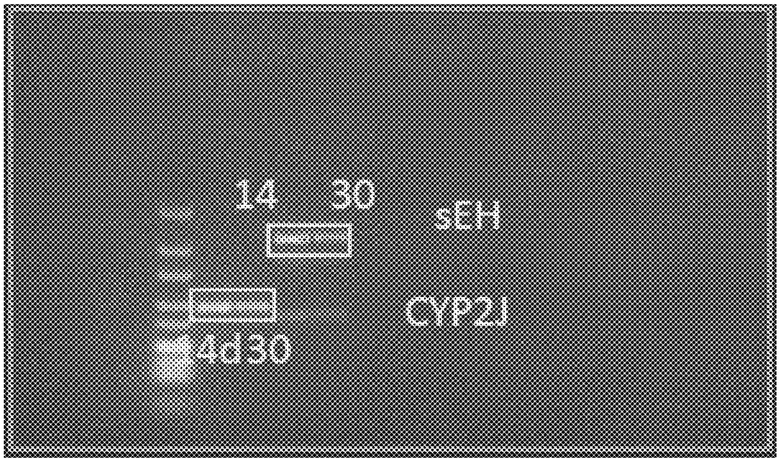
Figure 13B:
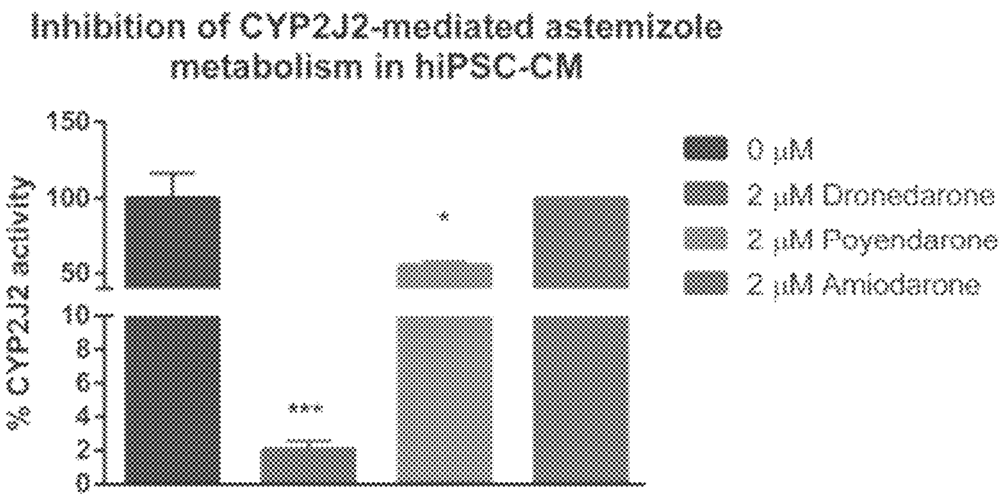

FIGS. 13A-13B. Show (FIG. 13A) relative expression of CYP2J2 and sEH mRNA. Total RNA was isolated from control hiPSC-CM and was transcribed to cDNA using Superscript II first-strand synthesis system. 5 ng complementary DNA (cDNA) was amplified using Quantifast PCR master mix using SYBR Green dye. The samples were run on 3% agarose gel electrophoresis. HiPSC-CM express both CYP2J2 and sEH after 14 and 30 days of differentiation. (FIG. 13B) HiPSC-CM were co-treated with astemizole and the inhibitor for 24 h and the metabolite of astemizole, O-desmethylastemizole, was measured using LC/MS/MS. Percentage of CYP2J2 activity was calculated and compared between the inhibitor and control. ***p<0.001; *p<0.05

Figures 14A, 14B:
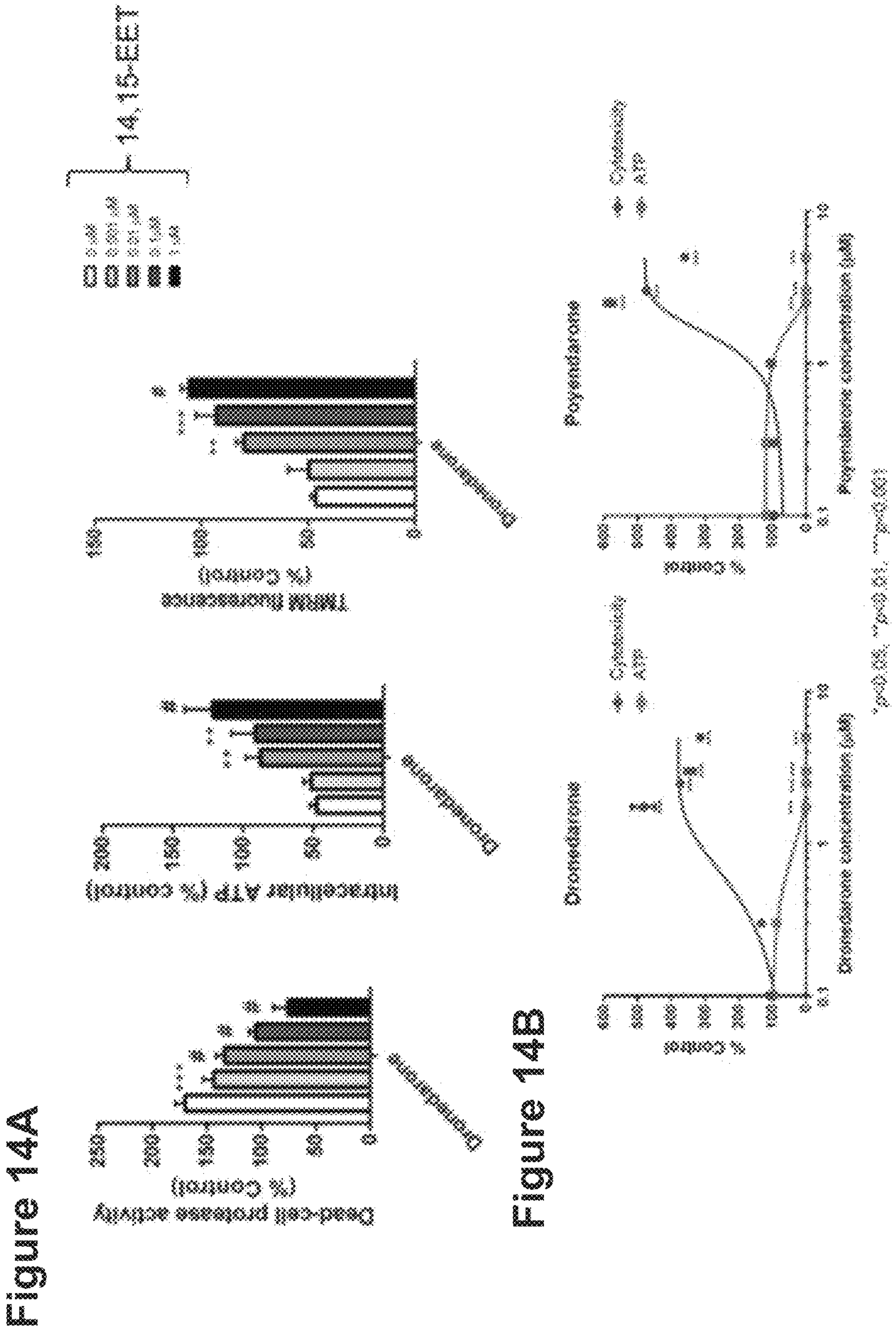

FIG. 14A-14B. Show (FIG. 14A) Dronedarone is cytotoxic to cardiomyocytes (increased dead-cell protease activity, reduced intracellular ATP, reduced TMRM fluorescence) but toxicity is rescued with enriched 14,15-EET in a concentration-dependent manner. (FIG. 14B) Poyendarone is significantly less toxic to cardiomyocytes (13-fold lower reduction in $IC_{50}$ of ATP decrease and 23-fold lower $EC_{50}$ in cytotoxicity where the $IC_{50}$ and $EC_{50}$ of dronedarone are 3.1 μM and 1.2 μM respectively).

Figure 15A:
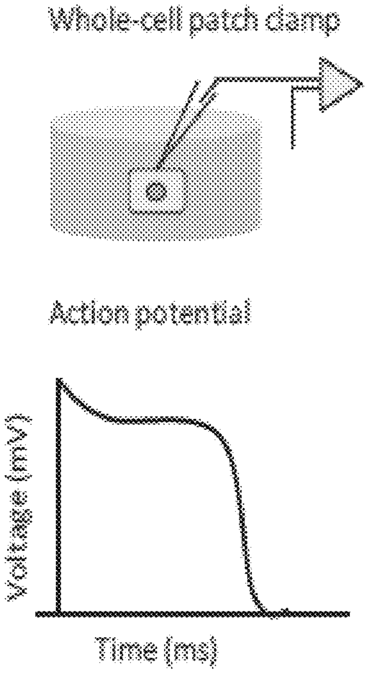
Figure 15B:
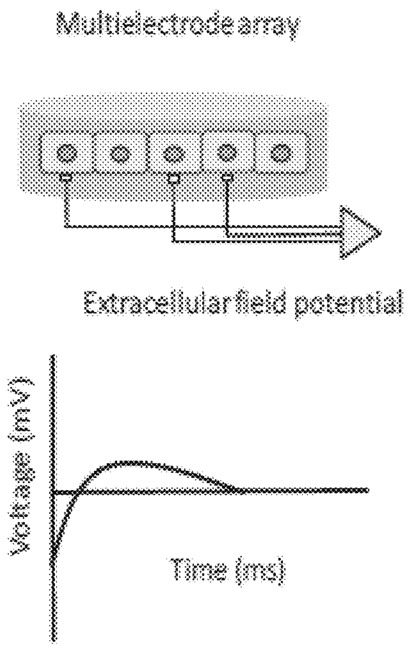
Figure 15C:
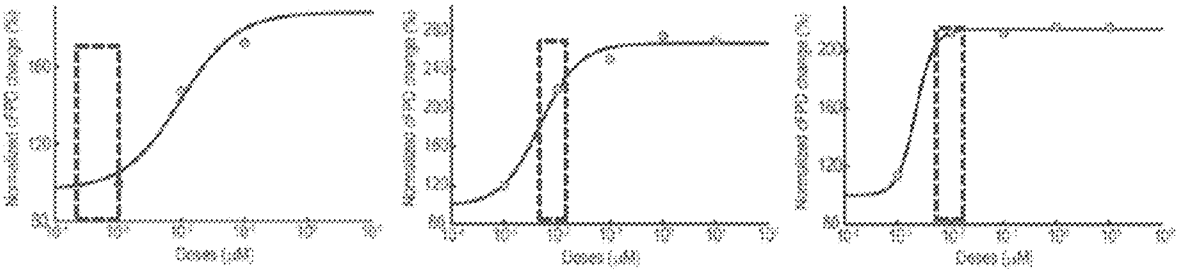
Figure 16A:
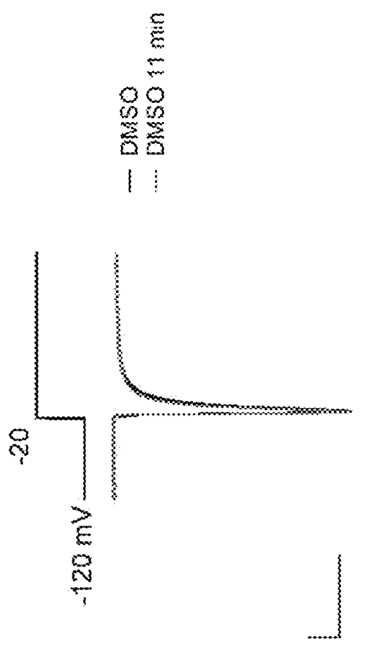
Figure 16B:
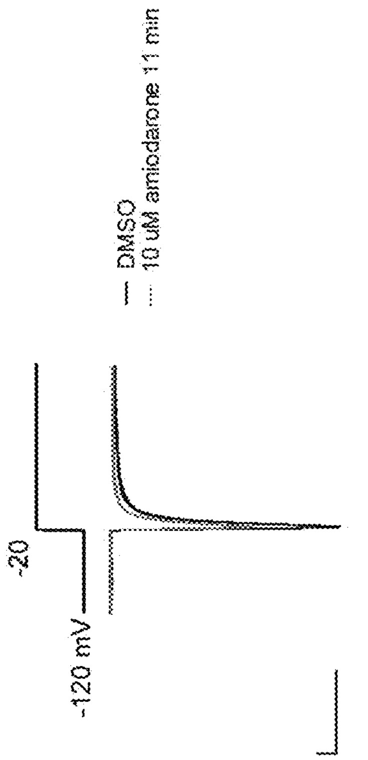
Figure 16C:
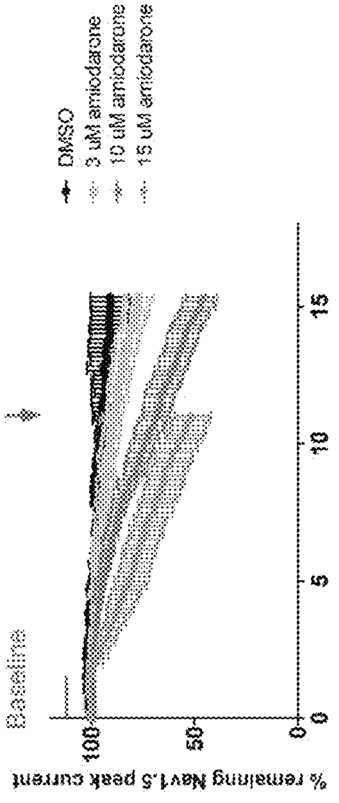
Figure 16D:
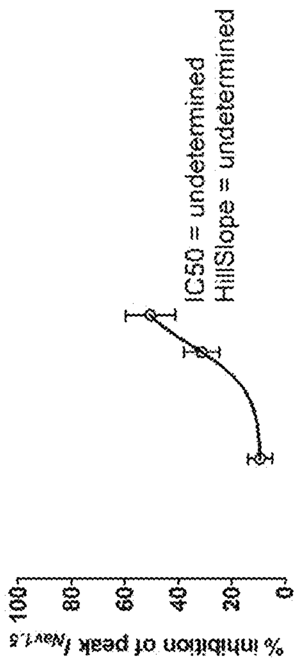

FIGS. 15A-15C. Show schematic of differences between action and extracellular field potential. (FIG. 15A) Action potentials are conventionally measured in a single cell using whole-cell patch clamp where the effect of single ion channel (e.g hERG channel) can be recorded. (FIG. 15B) Field potentials are measured in a group of cells (e.g embryoid bodies) using multiple electrodes (e.g. titanium nitride, 30 μm diameter) where a cumulative effect on all ion channels (e.g hERG and L-type calcium channel) and ion exchangers (e.g. NCX) can be measured simultaneously. (FIG. 15C) HiPSC-CM were treated with dronedarone, amiodarone and poyendarone (i.e. deuterated dronedarone) for 5 min and extracellular field recordings were performed for 180-300 ms at baseline. The local activation maps were generated using Cardio2D software (Multichannel systems, Reutlingen, Germany). The field potential duration (FPD) was normalized to beating rate of contracting areas with Bazzet correction formula and plotted against drug concentrations. Dose-dependent increase in the FPD of hiPSC-CM to dronedarone, amiodarone and poyendarone. Box with the broken line represents the effective therapeutic unbound plasma concentrations (ETUPC) of dronedarone and amiodarone as published previously. For comparison purposes, we have assumed the ETUPC of poyendarone to be similar to dronedarone FIGS. 16A-16D. Show Inhibition of Nav1.5 peak current by amiodarone. FIG. 16A. Nav1.5 channels current recorded at −20 mV from holding potential of −120 mV. Bottom, exemplary traces recorded in the presence of DMSO; start (black) or 11 min later (red). Scale bar; Y=1000 pA, X=10 ms. FIG. 16B. Exemplary traces of Nav1.5 channels current in the presence of DMSO (black) and 11 min after perfusion of 10 μM Amiodarone, format as in FIG. 16A. FIG. 16C. Averaged diary plot of % remaining Nav1.5 peak current for respectively conditions. The current was normalized against stable baseline peak current prior to averaging. FIG. 16D. Dose response curve for amiodarone inhibition on Nav1.5 current.

Figure 17A:
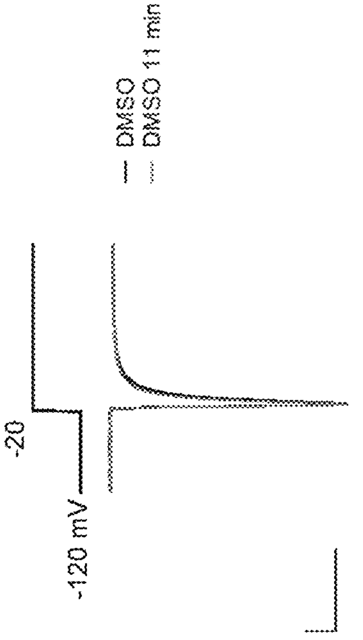
Figure 17B:
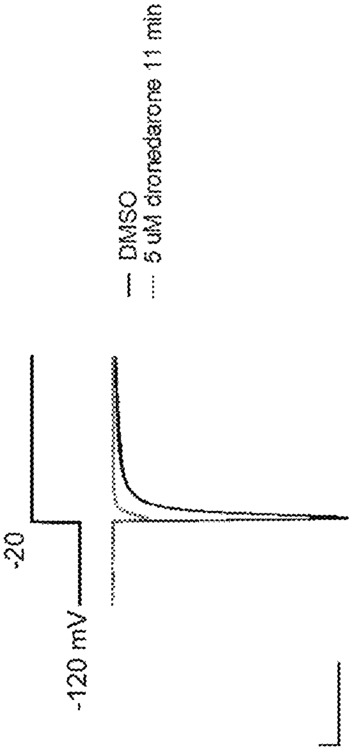
Figure 17C:
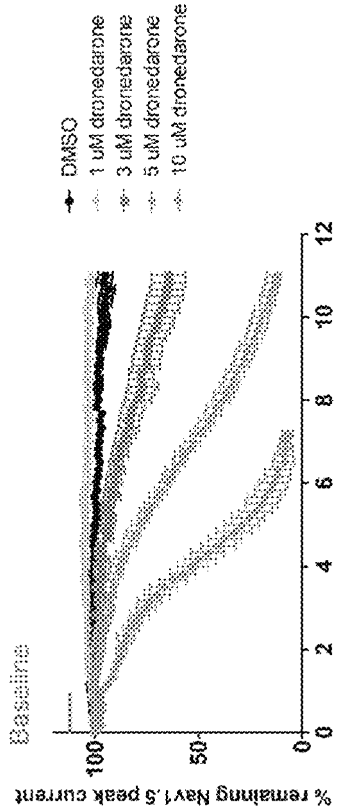
Figure 17D:
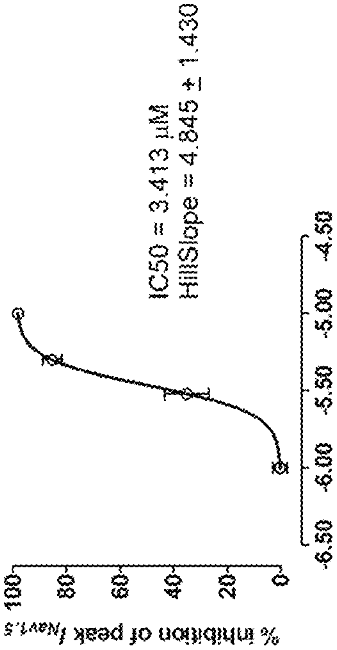

FIGS. 17A-17D. Show Inhibition of Nav1.5 peak current by dronedarone. FIG. 17A. Nav1.5 channels current recorded at −20 mV from holding potential of −120 mV. Bottom, exemplary traces recorded in the presence of DMSO; start (black) or 11 min later (red). Scale bar; Y=1000 pA, X=10 ms. FIG. 17B. Exemplary traces of Nav1.5 channels current in the presence of DMSO (black) and 11 min after perfusion of 5 μM dronedarone, format as in FIG. 17A. FIG. 17C. Averaged diary plot of % remaining Nav1.5 peak current for respectively conditions. The current was normalized against stable baseline peak current prior to averaging. FIG. 17D. Dose response curve for dronedarone inhibition on Nav1.5 current.

Figures 18A, 18B, 18C, 18D:
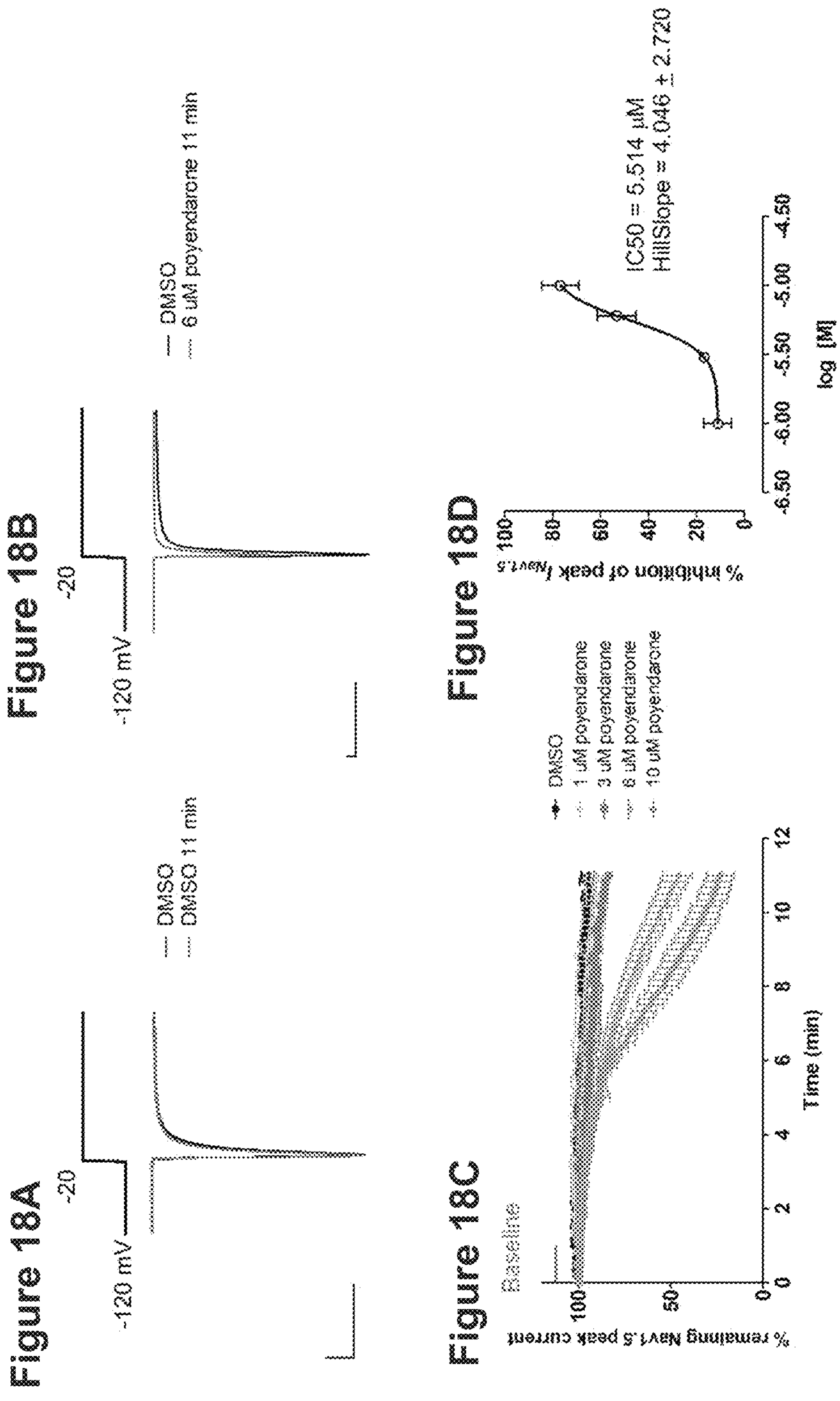
Figures 19A, 19B, 19C, 19D:
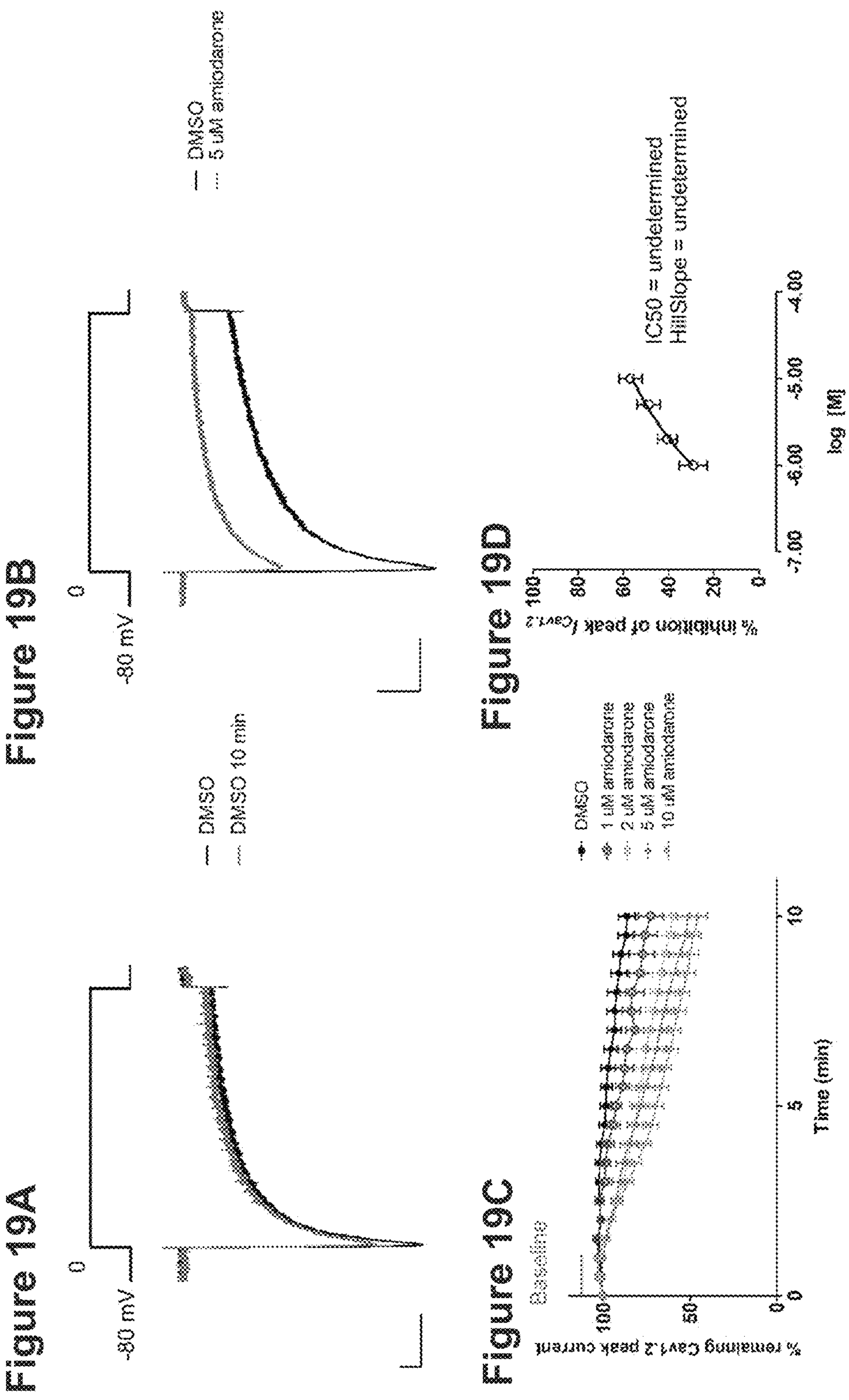

FIGS. 18A-18D. Show Inhibition of Nav1.5 peak current by poyendarone. FIG. 18A. Nav1.5 channels current recorded at −20 mV from holding potential of −120 mV. Bottom, exemplary traces recorded in the presence of DMSO; start (black) or 11 min later (red). Scale bar; Y=1000 pA, X=10 ms. FIG. 18B. Exemplary traces of Nav1.5 channels current in the presence of DMSO (black) and 11 min after perfusion of 6 μM poyendarone, format as in FIG. 18A. FIG. 18C. Averaged diary plot of % remaining Nav1.5 peak current for respectively conditions. The current was normalized against stable baseline peak current prior to averaging. FIG. 18D. Dose response curve for poyendarone inhibition on Nav1.5 current FIGS. 19A-19D. Show Inhibition of Cav1.2 peak current by amiodarone. FIG. 19A. Cav1.2 channels current recorded at 0 mV from holding potential of −80 mV. Bottom, exemplary traces recorded in the presence of DMSO; start (black) or 10 min later (red). Scale bar; Y=100 pA, X=100 ms. FIG. 19B. Exemplary traces of Cav1.2 channels current in the presence of DMSO (black) and after perfusion of 5 μM amiodarone, format as in FIG. 19A. FIG. 19C. Averaged diary plot of % remaining Cav1.2 peak current for respectively conditions. The current was normalized against stable baseline peak current prior to averaging. FIG. 19D. Dose response curve for amiodarone inhibition on Cav1.2 current.

Figure 20A:
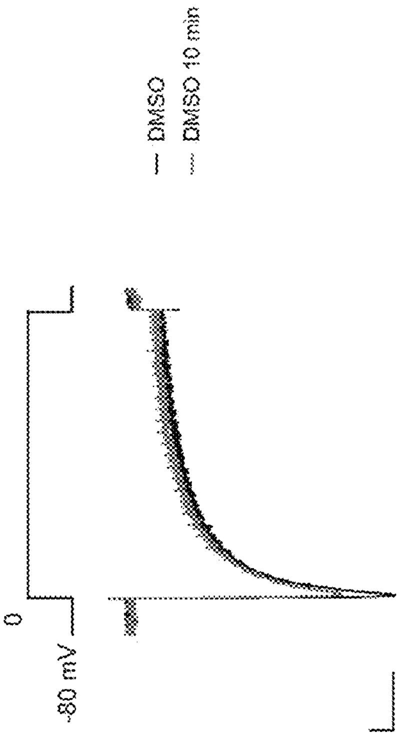
Figure 20B:
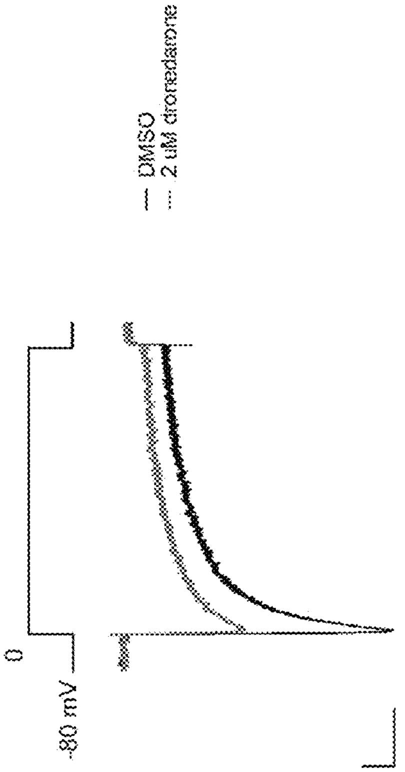
Figure 20C:
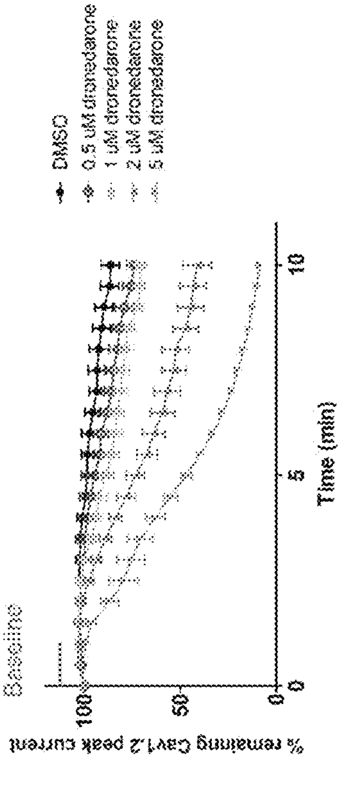
Figure 20D:
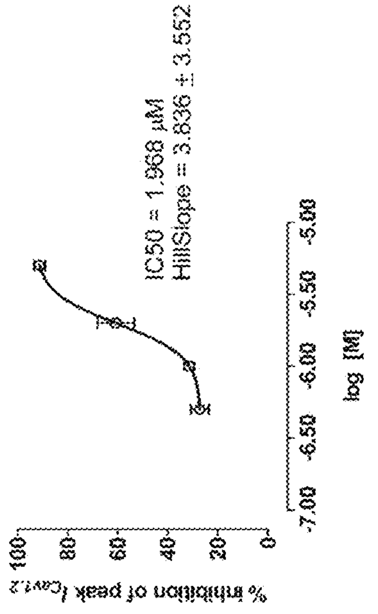

FIGS. 20A-20D. Show Inhibition of Cav1.2 peak current by dronedarone. FIG. 20A. Cav1.2 channels current recorded at 0 mV from holding potential of −80 mV. Bottom, exemplary traces recorded in the presence of DMSO; start (black) or 10 min later (red). Scale bar; Y=100 pA, X=100 ms. FIG. 20B. Exemplary traces of Cav1.2 channels current in the presence of DMSO (black) and after perfusion of 2 μM dronedarone, format as in FIG. 20A. FIG. 20C. Averaged diary plot of % remaining Cav1.2 peak current for respectively conditions. The current was normalized against stable baseline peak current prior to averaging. FIG. 20D. Dose response curve for dronedarone inhibition on Cav1.2 current.

Figures 21A, 21B, 21C, 21D:
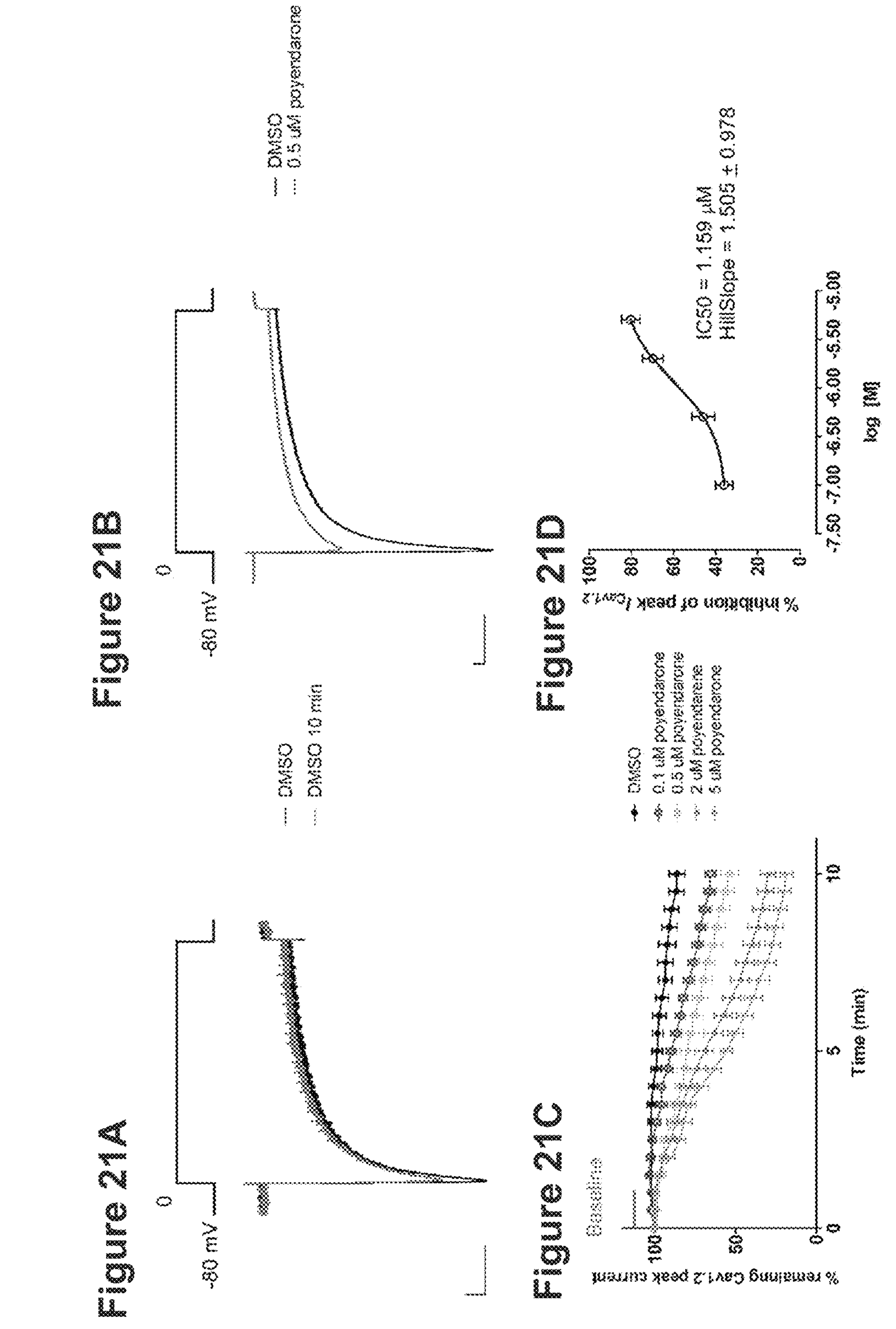

FIGS. 21A-21D. Show Inhibition of Cav1.2 peak current by poyendarone. FIG. 21A. Cav1.2 channels current recorded at 0 mV from holding potential of −80 mV. Bottom, exemplary traces recorded in the presence of DMSO; start (black) or 10 min later (red). Scale bar; Y=100 pA, X=100 ms. FIG. 21B. Exemplary traces of Cav1.2 channels current in the presence of DMSO (black) and after perfusion of 0.5 μM poyendarone, format as in FIG. 21A. FIG. 21C. Averaged diary plot of % remaining Cav1.2 peak current for respectively conditions. The current was normalized against stable baseline peak current prior to averaging. FIG. 21D. Dose response curve for poyendarone inhibition on Cav1.2 current.

Figures 22A, 22B, 22C:
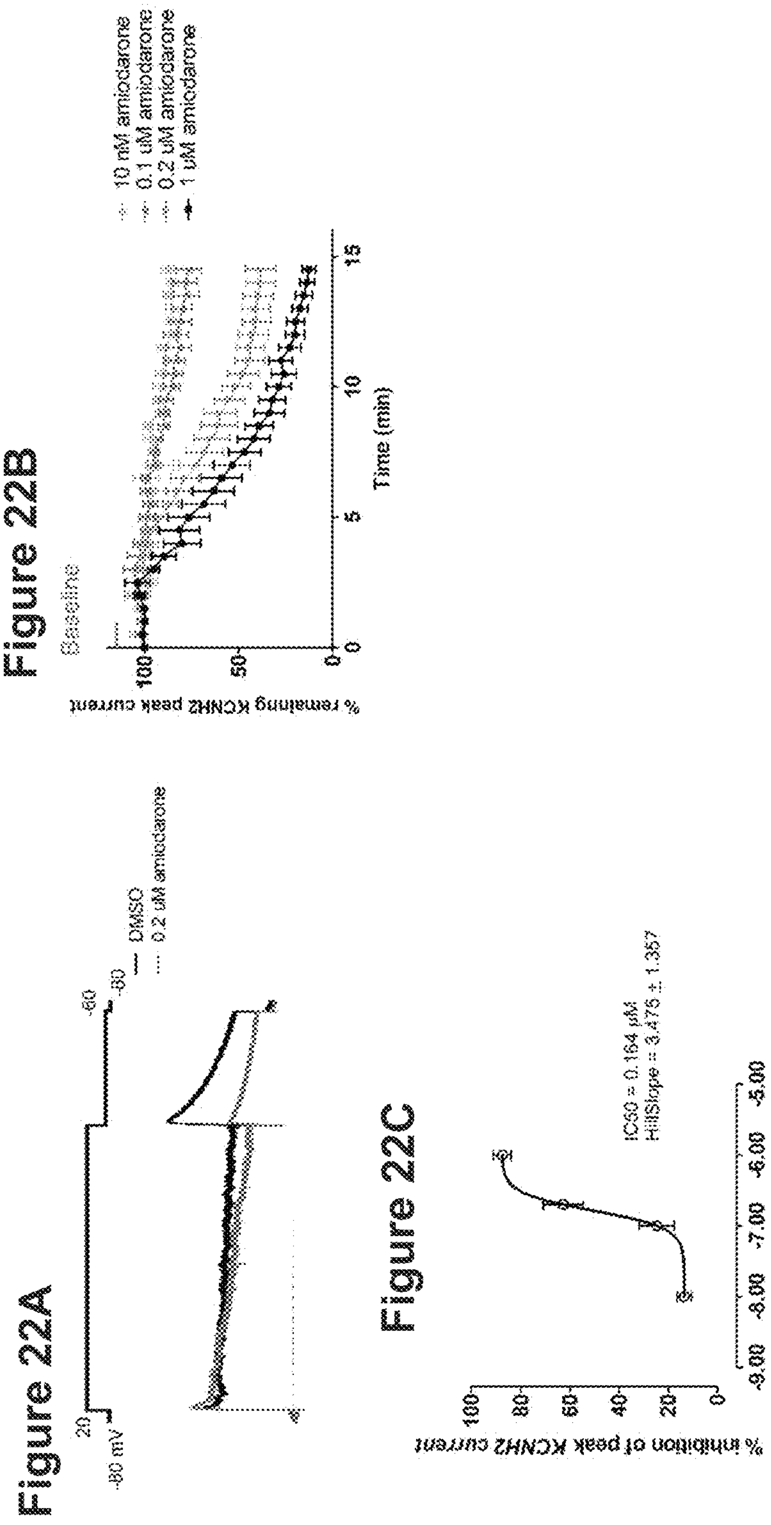

FIGS. 22A-22C. Show Inhibition of $K_v$11.1 tail current by amiodarone. FIG. 22A. $K_v$11.1 current was evoked from holding potential of −80 mV to 2.5 s pulses of 20 mV. The tail currents were subsequently recorded upon returning the voltage to −60 mV. Bottom, exemplary traces recorded in the presence of DMSO (black) or 0.2 μM amiodarone (red). Scale bar; Y=200 pA, X=500 ms. FIG. 22B. Averaged diary plot of % remaining $K_v$11.1 tail current for respectively conditions. The current was normalized against stable baseline peak tail current prior to averaging. FIG. 22C. Dose response curve for amiodarone inhibition on $K_v$11.1 current.

Figure 23A:
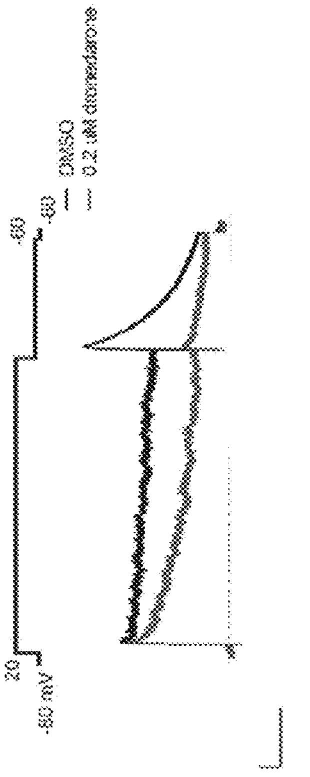
Figure 23B:
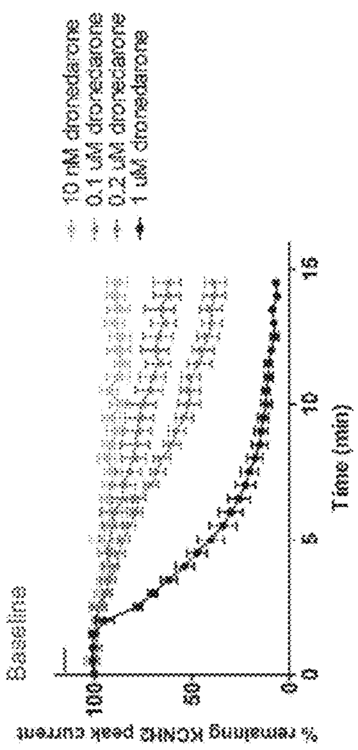
Figure 23C:
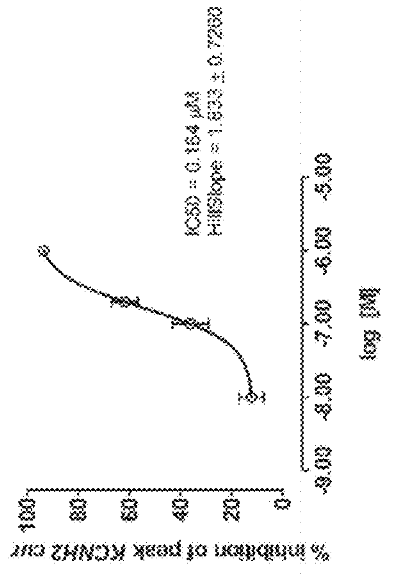

FIG. 23A-23C. Show Inhibition of $K_v$11.1 tail current by dronedarone. FIG. 23A. $K_v$11.1 current was evoked from holding potential of −80 mV to 2.5 s pulses of 20 mV. The tail currents were subsequently recorded upon returning the voltage to −60 mV. Bottom, exemplary traces recorded in the presence of DMSO (black) or 0.2 μM dronedarone (red). Scale bar; Y=200 pA, X=500 ms. FIG. 23B. Averaged diary plot of % remaining $K_v$11.1 tail current for respectively conditions. The current was normalized against stable baseline peak tail current prior to averaging. FIG. 23C. Dose response curve for dronedarone inhibition on $K_v$11.1 current.

Figure 24B:
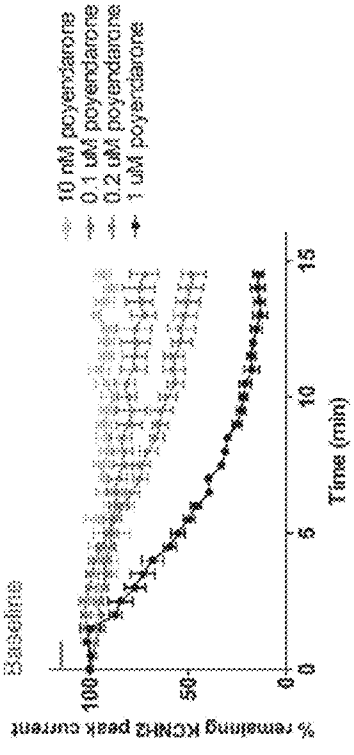
Figure 24A:
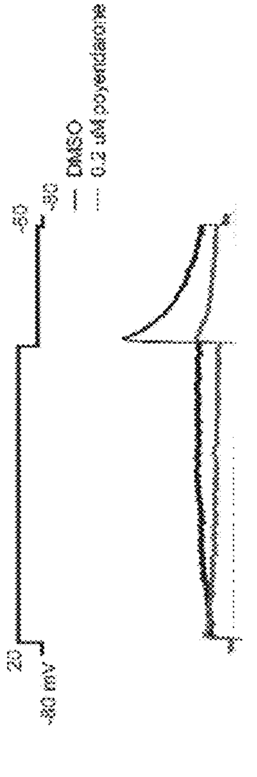
Figure 24C:
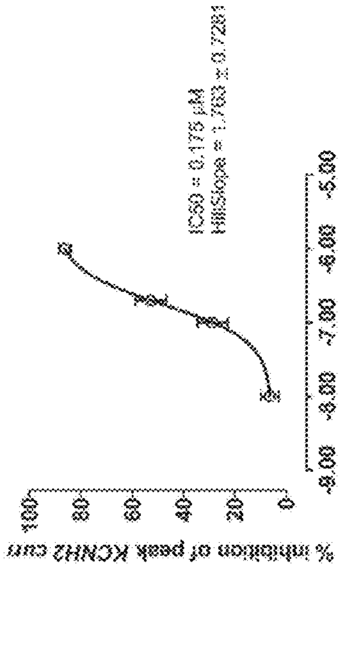

FIG. 24A-24C. Show Inhibition of $K_v$11.1 tail current by poyendarone. FIG. 24A. $K_v$11.1 current was evoked from holding potential of −80 mV to 2.5 s pulses of 20 mV. The tail currents were subsequently recorded upon returning the voltage to −60 mV. Bottom, exemplary traces recorded in the presence of DMSO (black) or 0.2 μM poyendarone (red). Scale bar; Y=200 pA, X=500 ms. FIG. 24B. Averaged diary plot of % remaining $K_v$11.1 tail current for respectively conditions. The current was normalized against stable baseline peak tail current prior to averaging. FIG. 24C. Dose response curve for poyendarone inhibition on $K_v$11.1 current.

Figure 25:
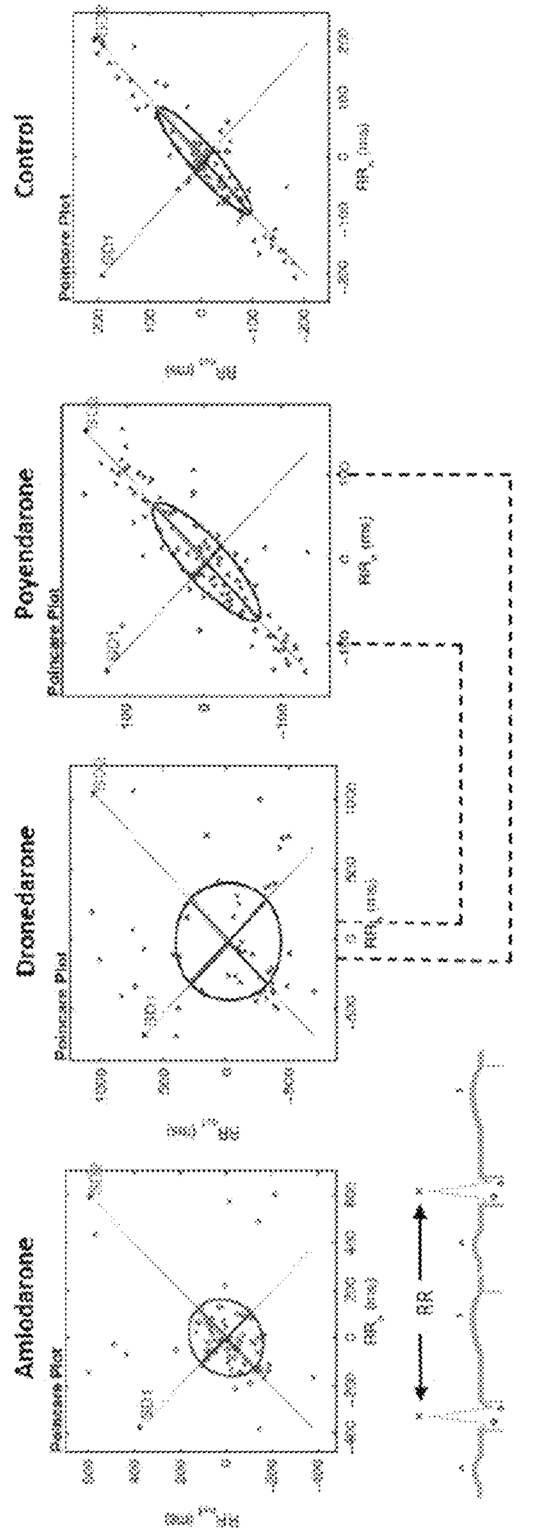

FIG. 25. Shows representative figures of Poincaré plot for control, 10 nM dronedarone, 10 nM amiodarone and 10 nM poyendarone. Each point refers to the inter-beat interval (IBI) between the preceding and succeeding beat. Inset: ECG showing R-R interval or inter-beat interval IBI. Scales of Poincaré plots of dronedarone and poyendarone are compared to reflect the lack of beat-to-beat variability (BBV) associated with the latter.

Figure 26A:
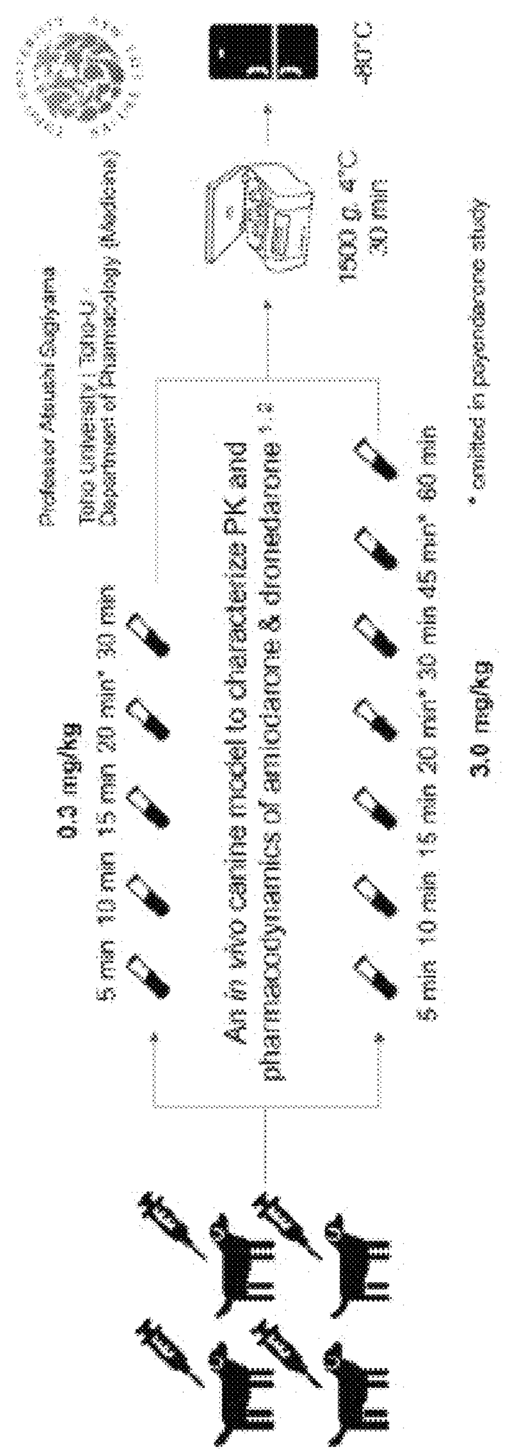
Figure 26B:
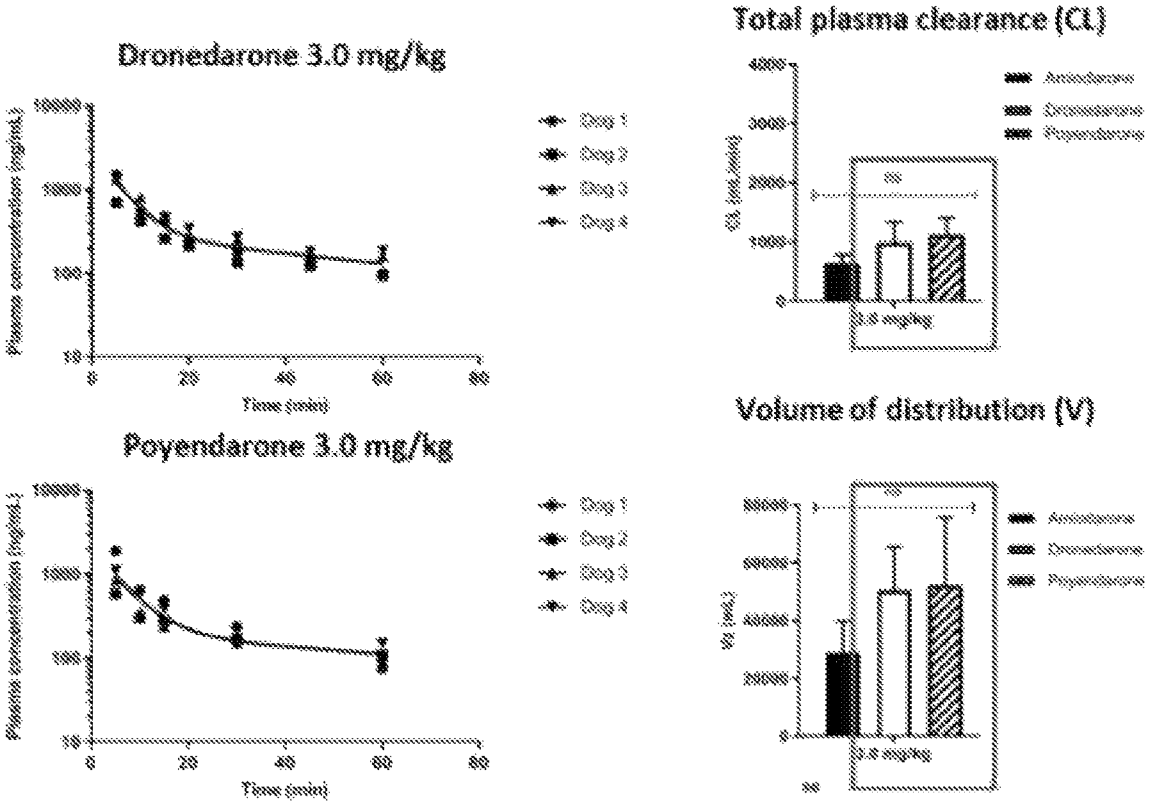

FIGS. 26A-26B. Show (FIG. 26A) brief schematic of in vivo dog experiments conducted at two doses of 0.3 mg/kg and 3.0 mg/kg of poyendarone. Plasma samples were analyzed using a validated LC/MS/MS method for poyendarone. (FIG. 26B) Poyendarone exhibits two-compartmental model similar to dronedarone where both plasma clearance (CL) and volume of distribution (V) values are comparable between the two compounds. This is aligned with our postulation as the major N-debutylation of poyendarone is conceptually not affected by deuteration.

FIGS. 27A-27F. Show in vitro metabolism of dronedarone and poyendarone respectively by (FIGS. 27A, B) CYP3A4, (FIGS. 27C, D) CYP3A5 and (FIGS. 27E, F) HLM.

FIGS. 28A-28J. Show simulated pharmacokinetic profiles of dronedarone (left column) and poyendarone (red dotted lines in right column) respectively, verified against clinical data for the following administrations: (FIGS. 28A, B) intravenous, (FIGS. 28C, D) single oral (fasted), (FIGS. 28E, F) single oral (fed), (FIGS. 28G, H) multiple oral (fasted), (FIGS. 281, J) multiple oral (fed). Black lines indicate predicted dronedarone concentrations over time while grey lines represent $95^{th}$ and $5^{th}$ percentile concentration-time profiles. Red triangles represent clinical data. Red dotted lines represent simulated poyendarone concentration-time profiles using the same clinical trial parameters as in the case of dronedarone. All studies were taken from the FDA review package of dronedarone.

FIGS. 29A-29D. Show verification of the multiple oral dosing administration for the dronedarone physiologically-based pharmacokinetic (PBPK) model with LIN2890 clinical trial data [27], (FIG. 29A) without MBI and (FIG. 29C) with MBI. Magnified portions of the graphs are presented in (FIG. 29B) and (FIG. 29D) respectively, with axis titles removed for readability. Red triangles denote clinical concentrations.

Figure 30:
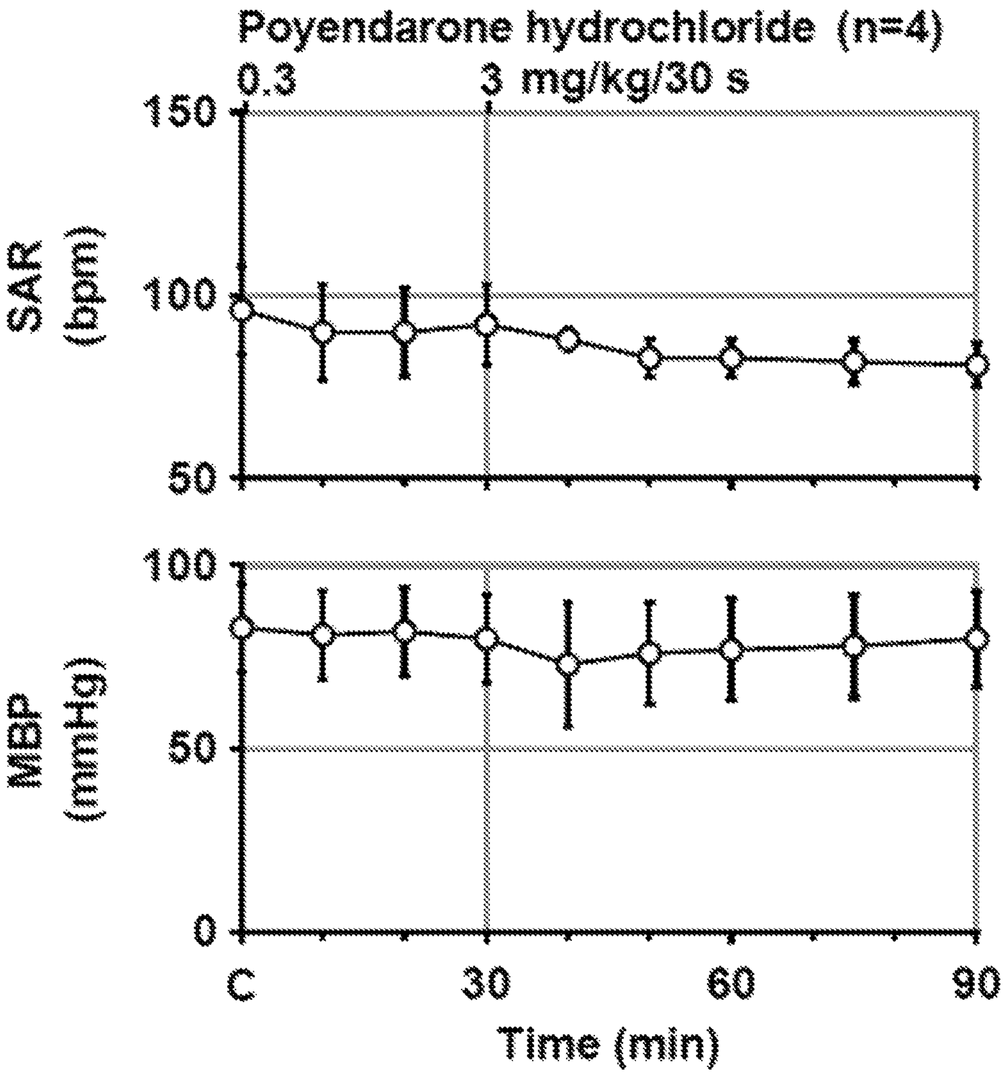

FIG. 30. Shows time courses of changes in the sinoatrial rate (SAR) and mean blood pressure (MBP). Data are presented as mean±S.E.M. (n=4).

Figure 31:
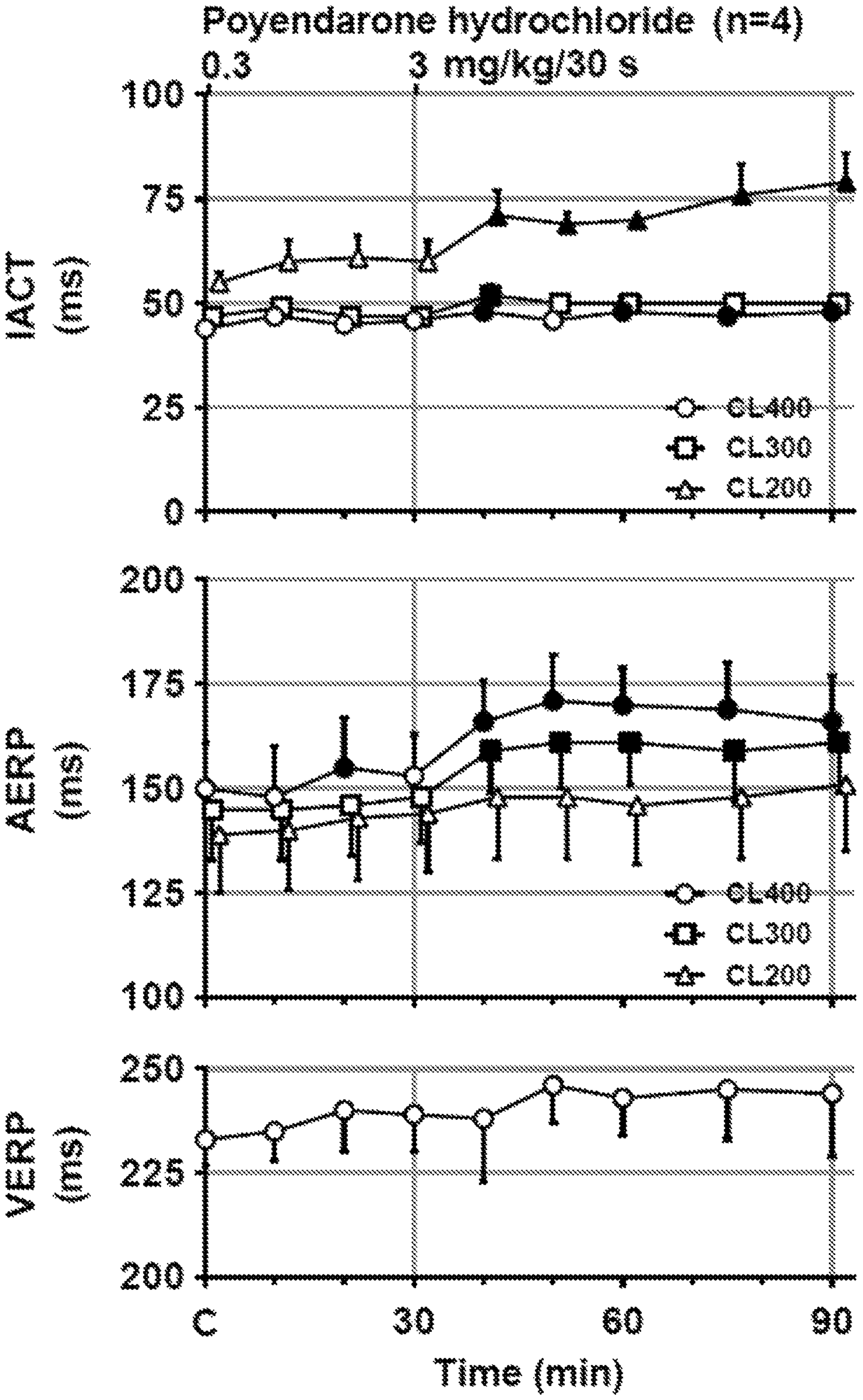

FIG. 31. Shows time courses of changes in the inter-atrial conduction time (IACT, top) at atrial pacing cycle lengths of 400 ms ($IACT_{(CL400)}$), 300 ms ($IACT_{(CL300)}$) and 200 ms ($IACT_{(CL200)}$); atrial effective refractory period (AERP, middle) at basic atrial pacing cycle lengths of 400 ms ($AERP_{(CL400)}$), 300 ms ($AERP_{(CL300)}$) and 200 ms ($AERP_{(CL200)}$); and ventricular effective refractory period (VERP, bottom) at a basic ventricular pacing cycle length of 400 ms ($VERP_{(CL400)}$). Data are presented as mean±S.E.M. (n=4). Closed symbols represent statistically significant differences from each control value (C) by $p<0.05$ FIG. 32. Shows typical tracings of the electrograms of right (RA) and left atrium (LA), electrocardiogram (ECG) and arterial blood pressure (BP) during and after the burst pacing at pre-drug basal control (Control, upper) and 20 min after the administration of 3 mg/kg of poyendarone hydrochloride (20 min after 3 mg/kg poyendarone hydrochloride, lower). Note that the duration of atrial fibrillation was shortened from 6.9 s to 1.8 s after the administration of poyendarone hydrochloride.

Figure 33:
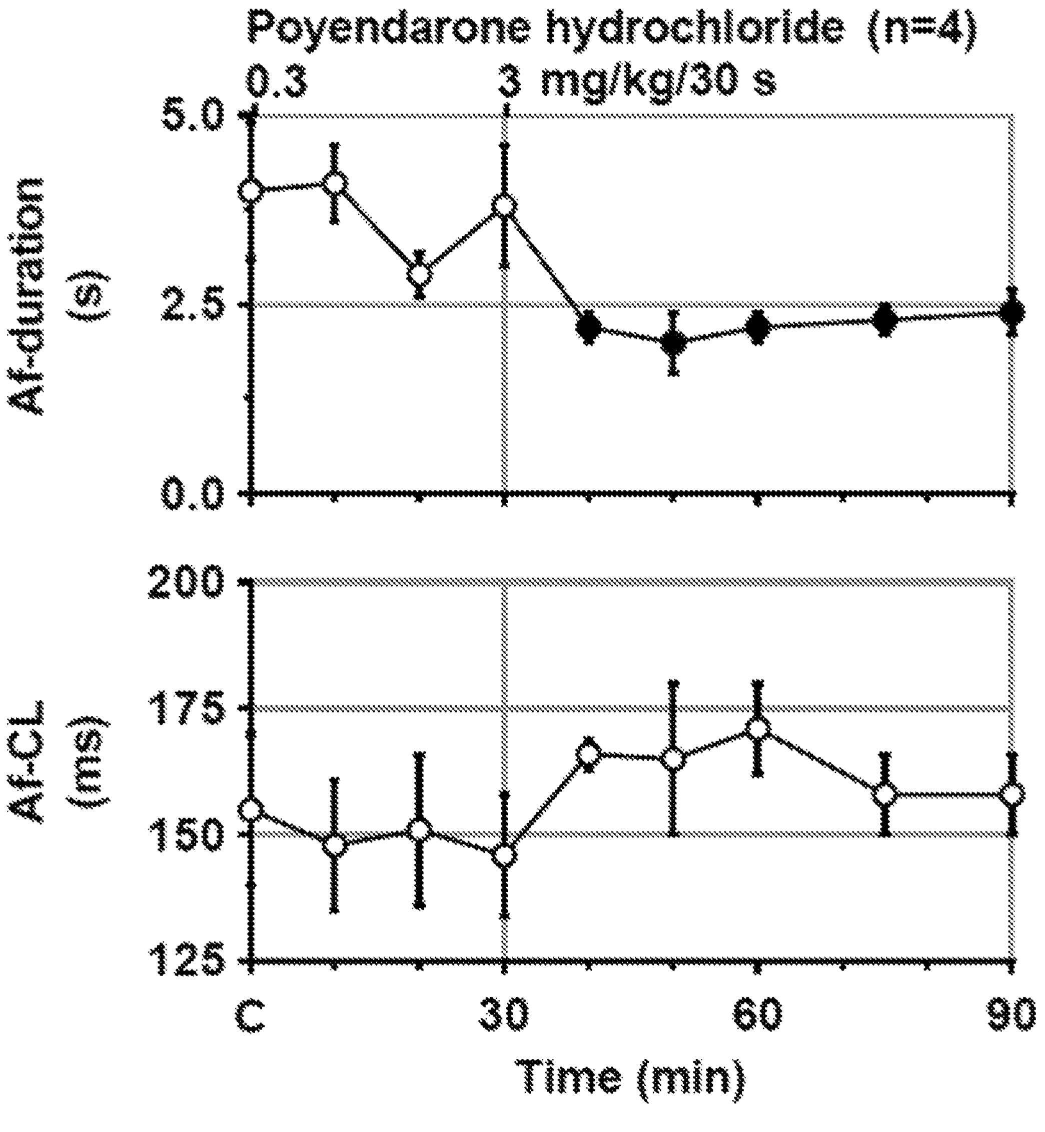

FIG. 33. Shows time courses of changes in the duration (Af-duration) and cycle length (Af-CL) of atrial fibrillation. Data are presented as mean±S.E.M. (n=4). Closed symbols represent statistically significant differences from each control value (C) by $p<0.05$.

Figure 34:
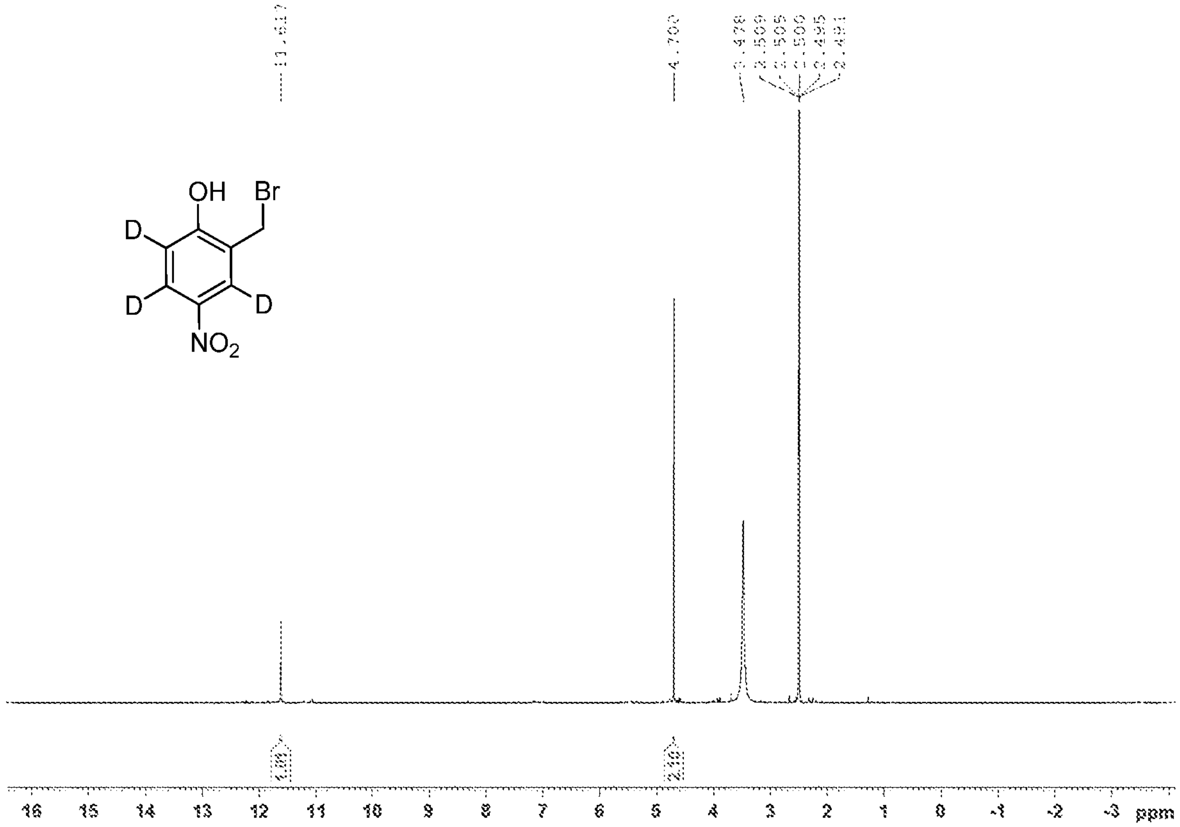

FIG. 34. Shows the $^1$H NMR spectra of 2-(bromomethyl)-4-nitrophenol(3,5,6-$d_3$) (D1) prepared according to the synthetic scheme shown schematically in FIG. 5.

Figure 35:
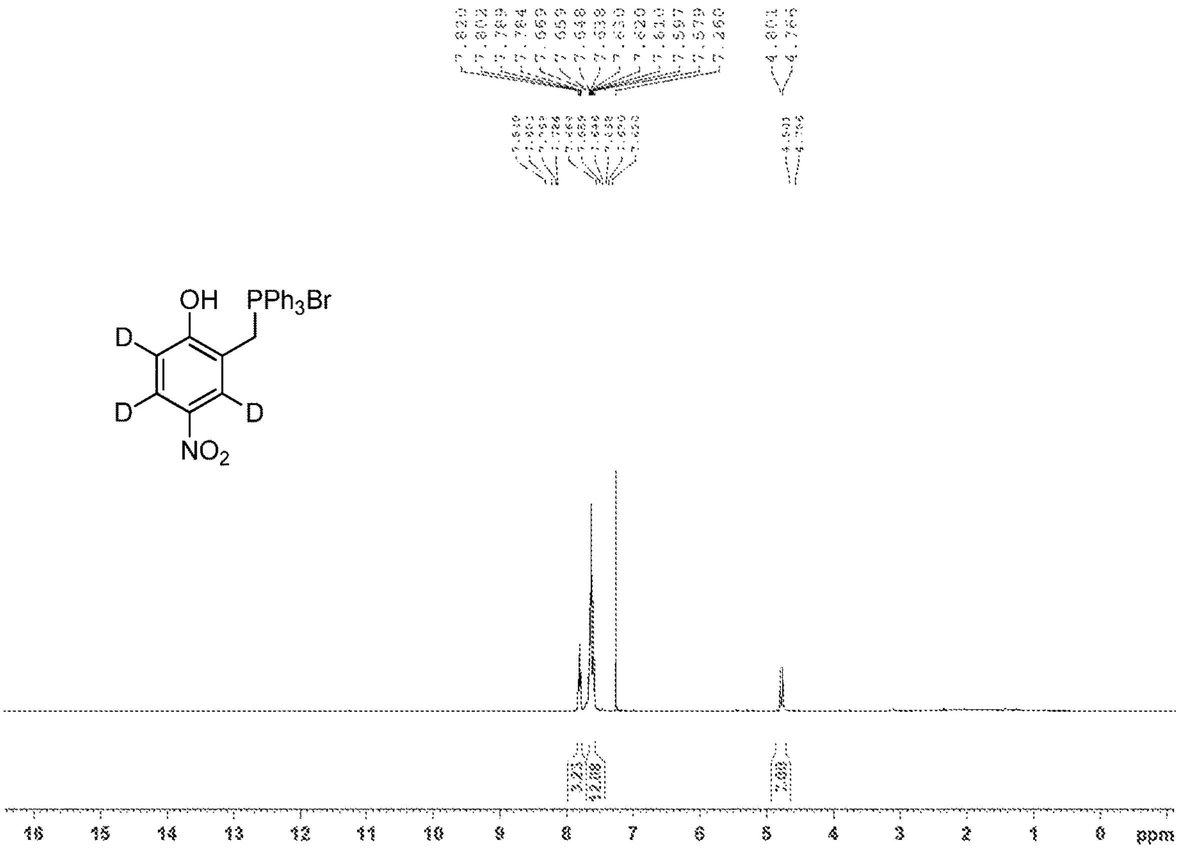

FIG. 35. Shows the $^1$H NMR spectra of 2-((bromotriphenylphosphoranyl)methyl)-4-nitrophenol(3,5,6-$d_3$) (D2) prepared according to the synthetic scheme shown schematically in FIG. 5.

Figure 36:
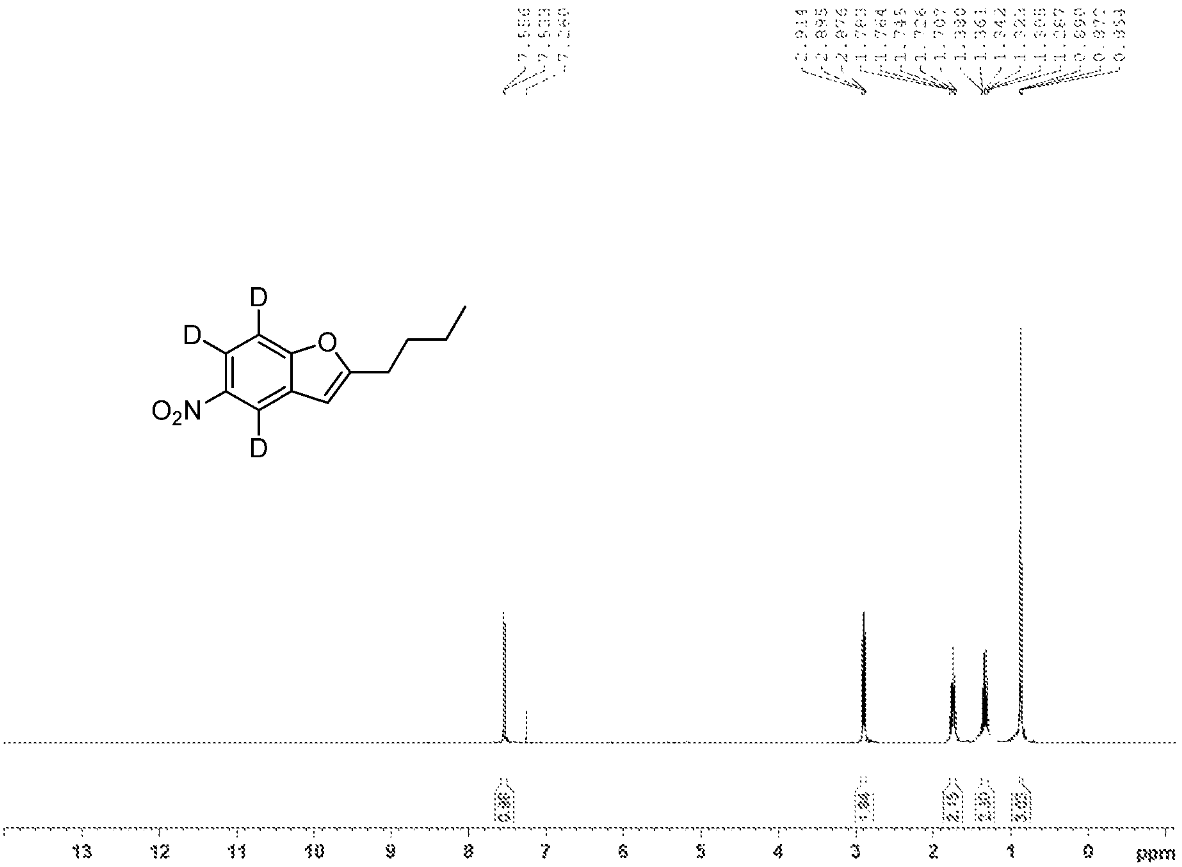

FIG. 36. Shows the $^1$H NMR spectra of 2-butyl-5-nitro-1-benzo(4,6,7-$d_3$)furan (D3) prepared according to the synthetic scheme shown schematically in FIG. 5.

Figure 37:
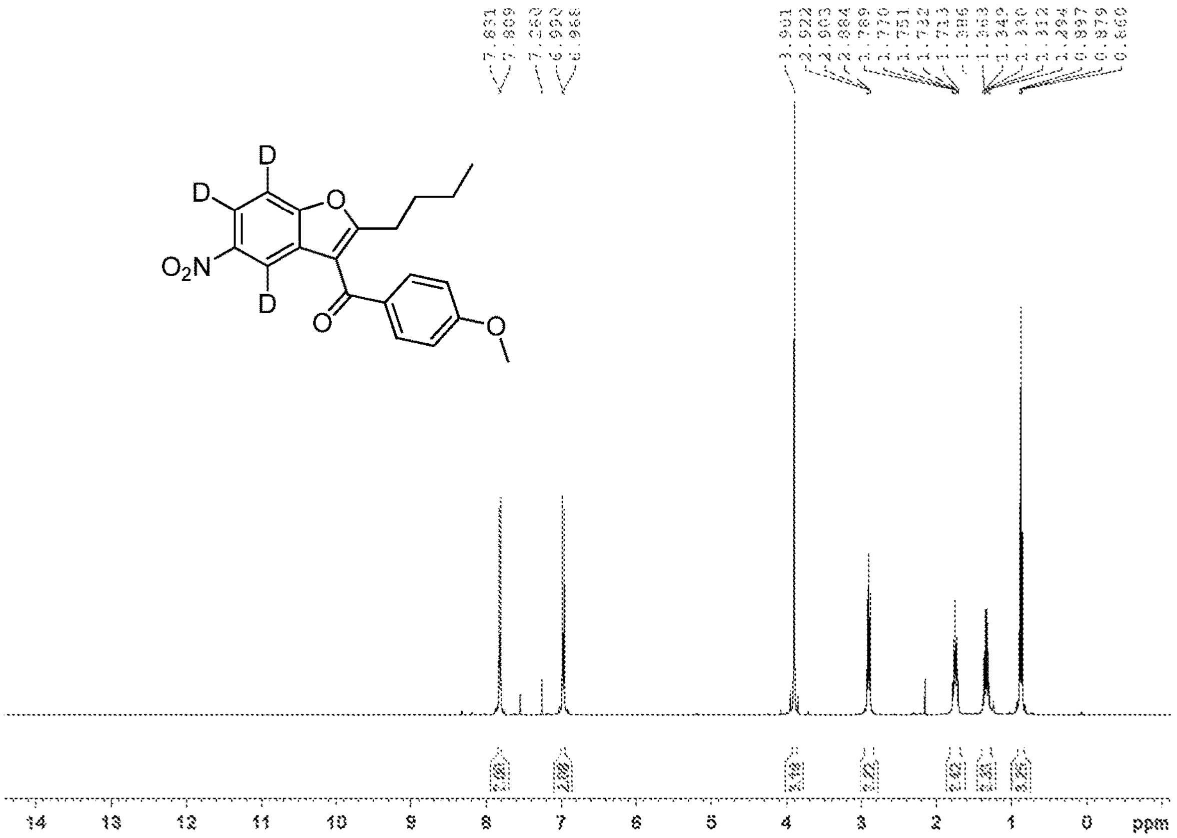

FIG. 37. Shows the $^1$H NMR spectra of (2-butyl-5-nitro-1-benzo(4,6,7-$d_3$)furan-3-yl)(4-methoxyphenyl)methanone (D4) prepared according to the synthetic scheme shown schematically in FIG. 5.

Figure 38:
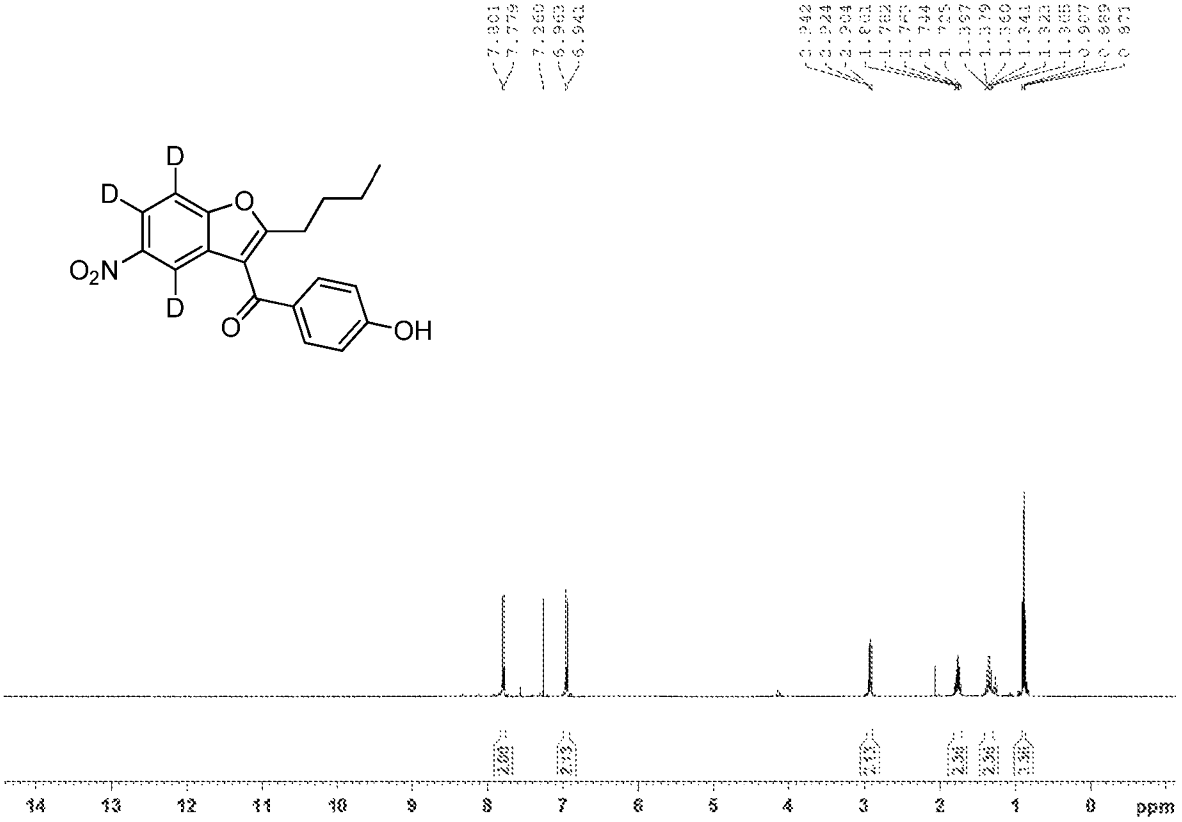

FIG. 38. Shows the $^1$H NMR spectra of (2-butyl-5-nitro-1-benzo(4,6,7-$d_3$)furan-3-yl)(4-hydroxyphenyl)methanone (D5) prepared according to the synthetic scheme shown schematically in FIG. 5.

Figure 39:
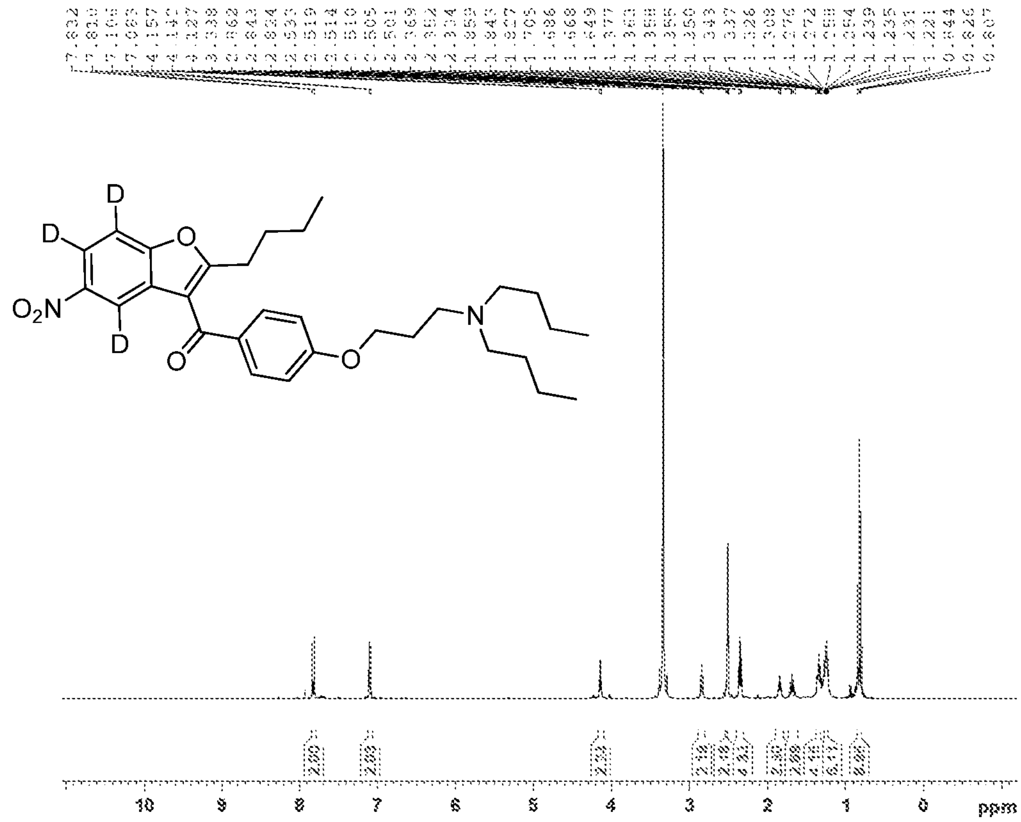

FIG. 39. Shows the $^1$H NMR spectra of (2-butyl-5-nitro-1-benzo(4,6,7-$d_3$)-furan-3-yl)(4-(3-(dibutylamino) propoxy) phenyl)methanone (D6) prepared according to the synthetic scheme shown schematically in FIG. 5.

Figure 40:
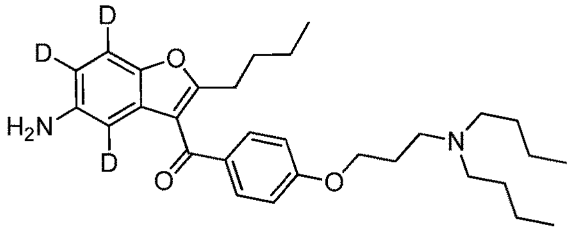
Figure 40:
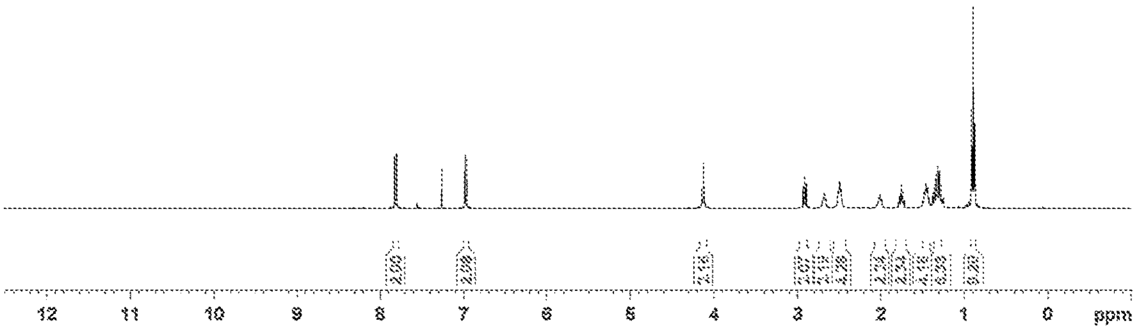

FIG. 40. Shows the $^1$H NMR spectra of (5-amino-2-butyl-1-benzo(4,6,7-$d_3$)-furan-3-yl)(4-(3-(dibutylamino) propoxy) phenyl)methanone (D7) prepared according to the synthetic scheme shown schematically in FIG. 5.

Figure 41:
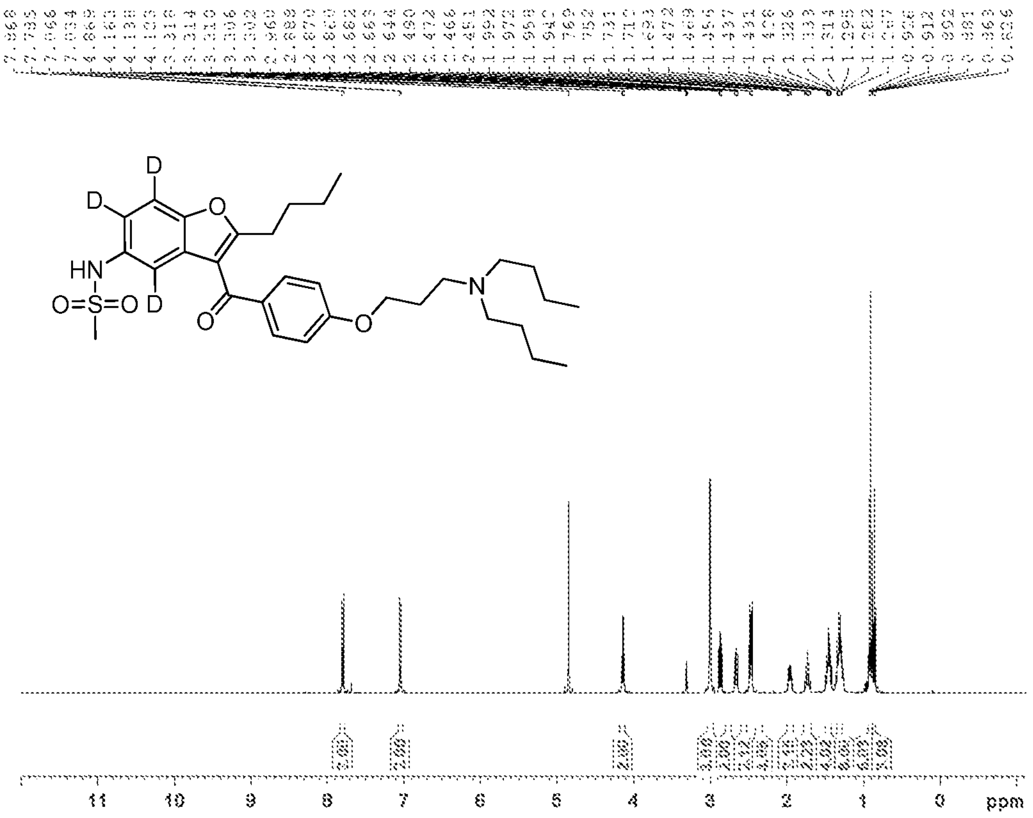

FIG. 41. Shows the $^1$H NMR spectra of Methanesulfonamide, N-(2-butyl-3-(4-(3-(dibutylamino)propoxy)benzoyl)-1-benzo(4,6,7-$d_3$)-furan-5-yl)hydrochloride (D8) prepared according to the synthetic scheme shown schematically in FIG. 5.

Figure 42:
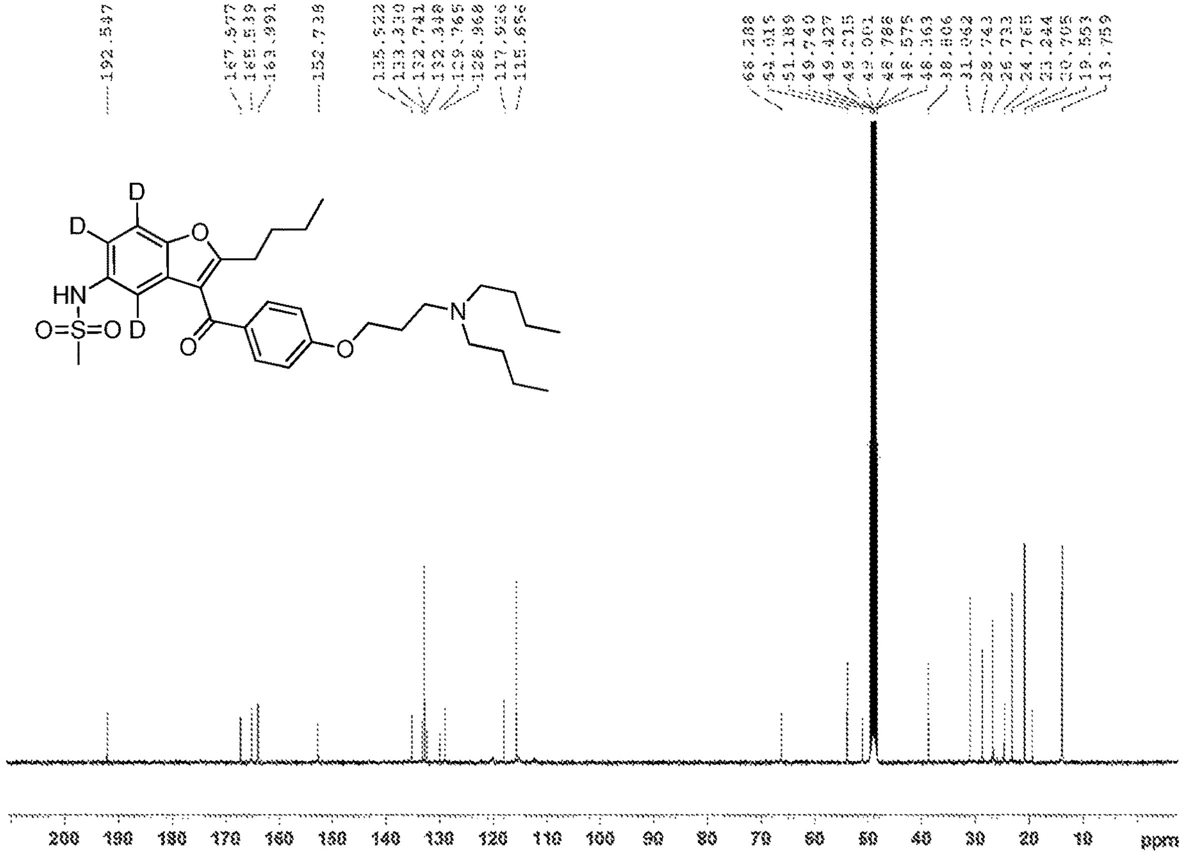

FIG. 42. Shows the $^{13}$C NMR spectra of Methanesulfonamide, N-(2-butyl-3-(4-(3-(dibutylamino)propoxy)benzoyl)-1-benzo(4,6,7-$d_3$)-furan-5-yl)hydrochloride (D8) prepared according to the synthetic scheme shown schematically in FIG. 5.

Figure 43:
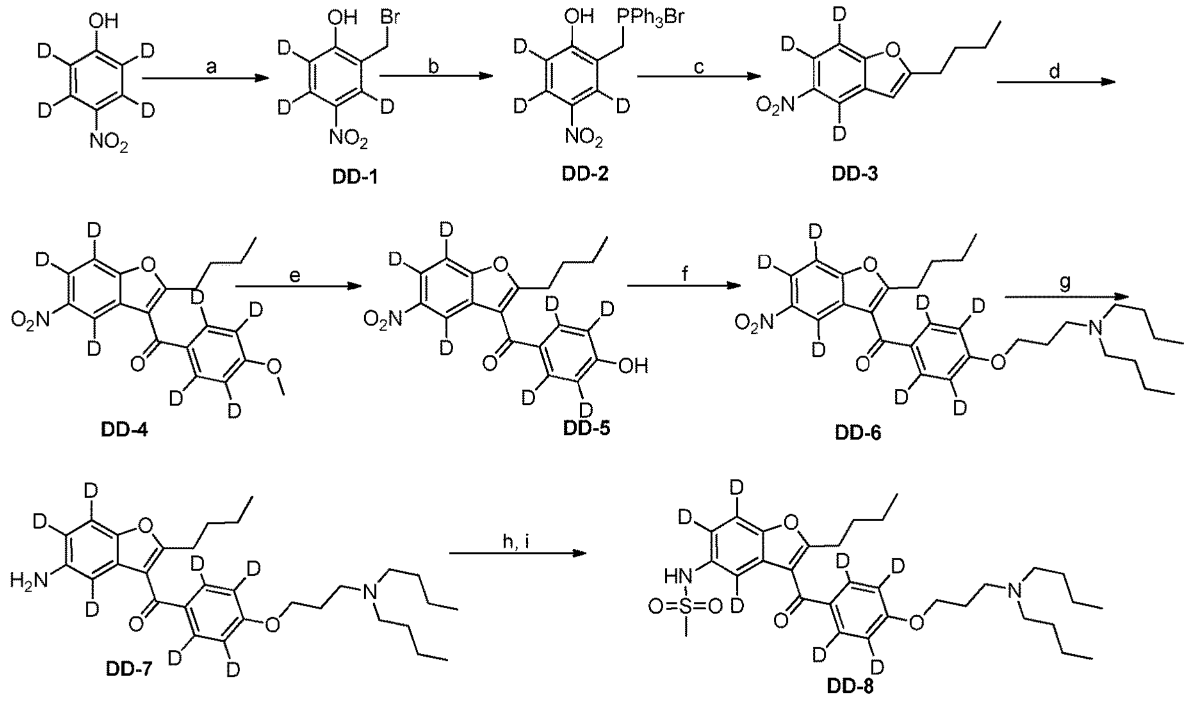

FIG. 43. Shows the synthesis of the deuterated dronedarone derivative 'Compound 3'. 'D' denotes the presence of the deuterium isotope. Reagents and conditions: (a) conc $H_2SO_4$, 48% HBr, 35% HCHO, 75° C., 6 h, DD1: 76.0%. (b) toluene, $PPh_3$, reflux, 1 h, DD2: 98.0%. (c) $CHCl_3$, pyridine, valeroyl chloride, reflux 2h; toluene, triethylamine, reflux, 3h, DD3: 75.0%. (d) dichloromethane, $C_6H_5COCl$(p-$OCH_3$), $SnCl_4$, rt, 24 h, DD4: 95.0%. (e) dichloromethane, $AlCl_3$, reflux, 24h, DD5: 98.0%. (f) acetone, anhyd.$K_2CO_3$, 1-chloro-3-di-n-butylaminopropane, reflux, overnight, DD6: 79.0%. (g) Fe, EtOH, $H_2O$, conc. HCl, 65° C., 3 h DD7: 82.0%. (h) dichloromethane, pyridine, $CH_3SO_2Cl$, 35° C., 3h (i) methanol, hydrochloric acid, 0° C., 3 h, DD-8: 80.0%.

Figure 44:
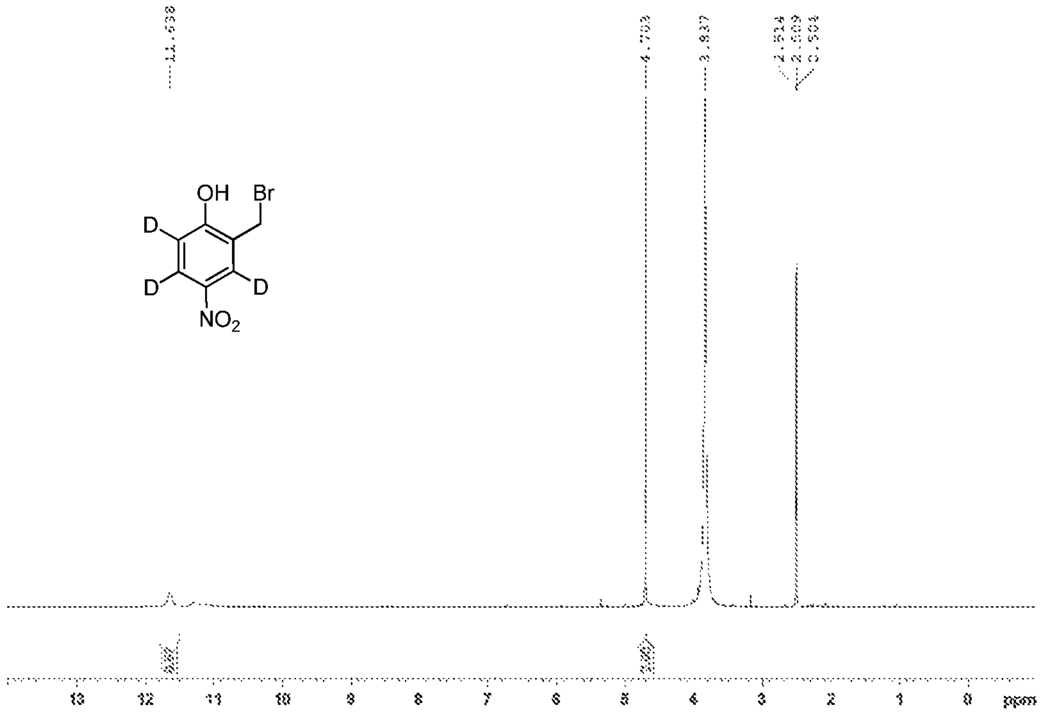

FIG. 44. Shows the $^1$H NMR spectra of 2-(bromomethyl)-4-nitrophenol (2,3,5,6-$d_4$) (DD1) prepared according to the synthetic scheme shown schematically in FIG. 43.

Figure 45:
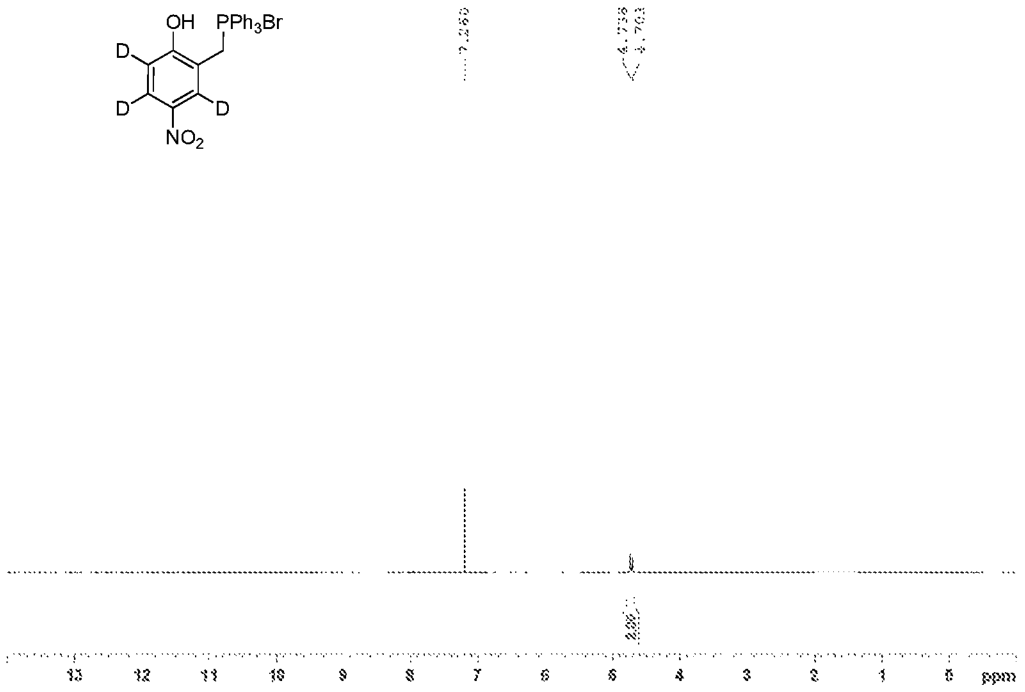

FIG. 45. Shows the $^1$H NMR spectra of 2-((bromotriphenylphosphoranyl)methyl)-4-nitrophenol (2,3,5,6-$d_4$) (DD2) prepared according to the synthetic scheme shown schematically in FIG. 43.

Figure 46:
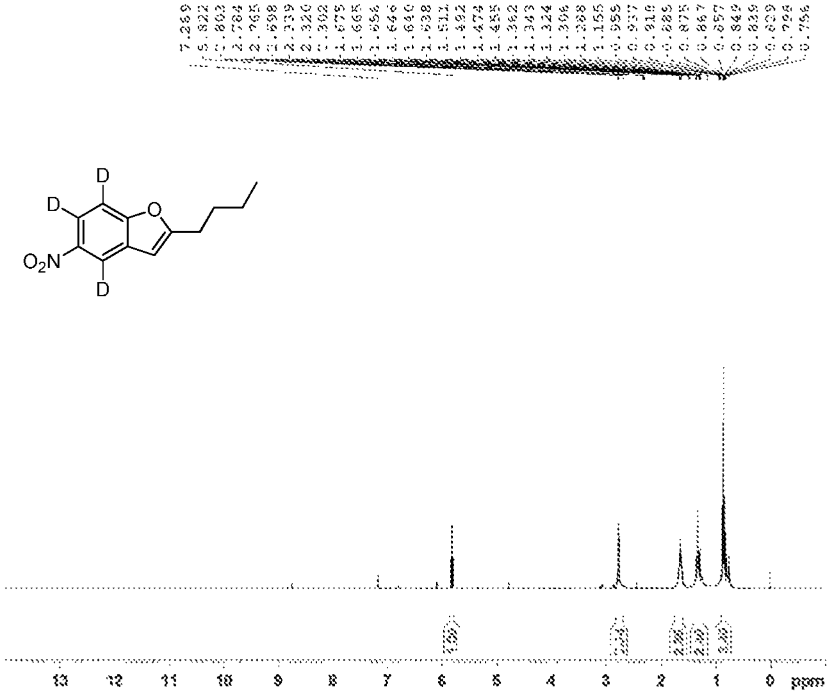

FIG. 46. Shows the $^1$H NMR spectra of 2-butyl-5-nitro-1-benzo (4,6,7-$d_3$) furan (DD3) prepared according to the synthetic scheme shown schematically in FIG. 43.

Figure 47:
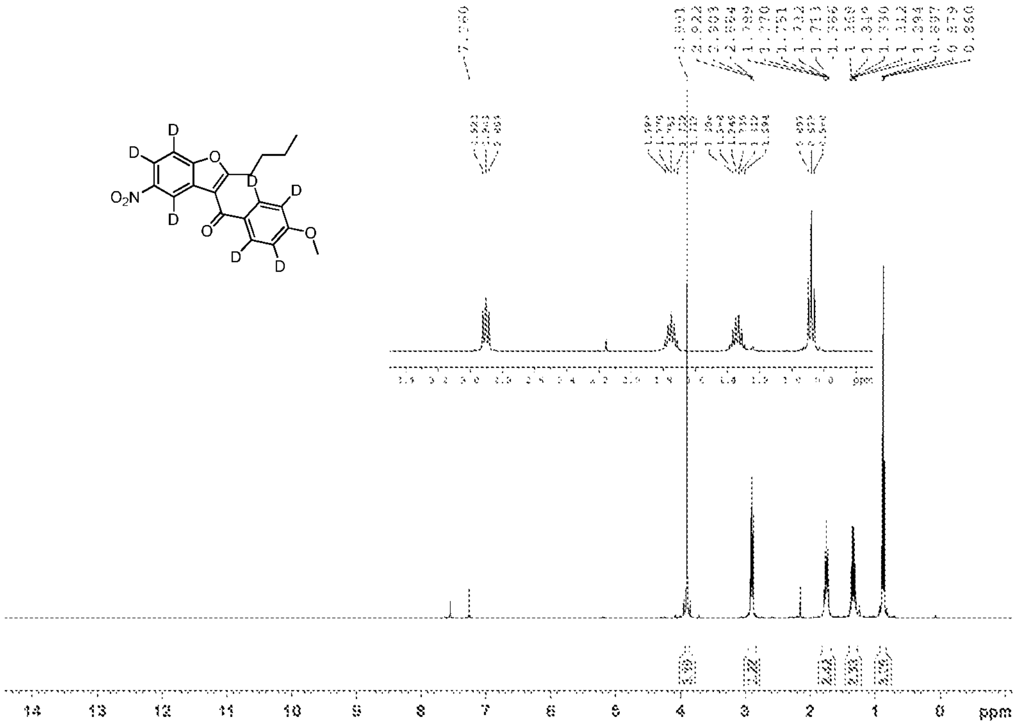

FIG. 47. Shows the $^1$H NMR spectra of (2-butyl-5-nitro-1-benzo(4,6,7-$d_3$)furan-3-yl)(4-methoxyphenyl (2,3,5,6-$d_4$))methanone (DD4) prepared according to the synthetic scheme shown schematically in FIG. 43.

Figure 48:
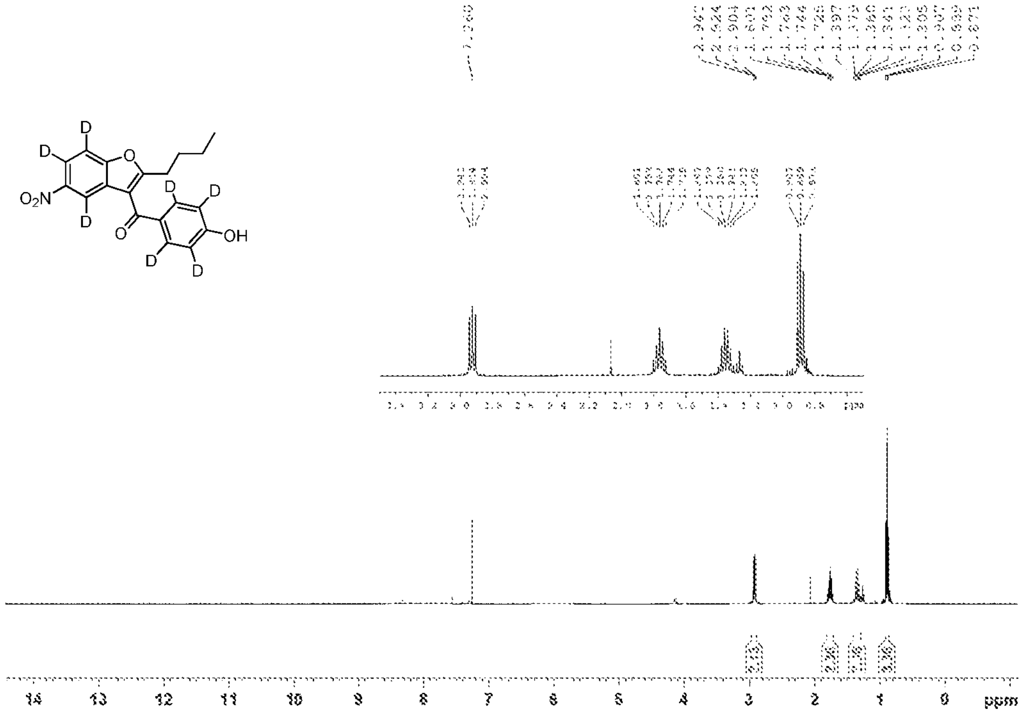

FIG. 48. Shows the $^1$H NMR spectra of (2-butyl-5-nitro-1-benzo(4,6,7-$d_3$) furan-3-yl)(4-hydroxyphenyl (2,3,5,6-$d_4$)) methanone (DD5) prepared according to the synthetic scheme shown schematically in FIG. 43.

Figure 49:
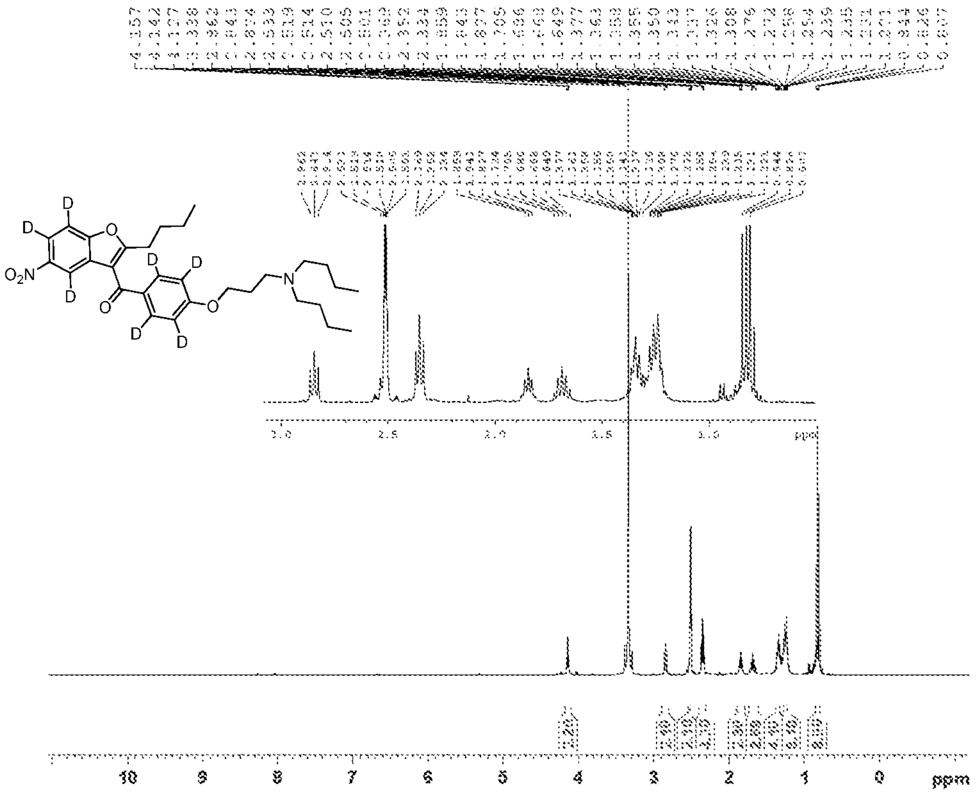

FIG. 49. Shows the $^1$H NMR spectra of (2-butyl-5-nitro-1-benzo(4,6,7-$d_3$)furan-3-yl)(4-(3-(dibutylamino) propoxy) phenyl (2,3,5,6-$d_4$))methanone (DD6) prepared according to the synthetic scheme shown schematically in FIG. 43.

Figure 50:
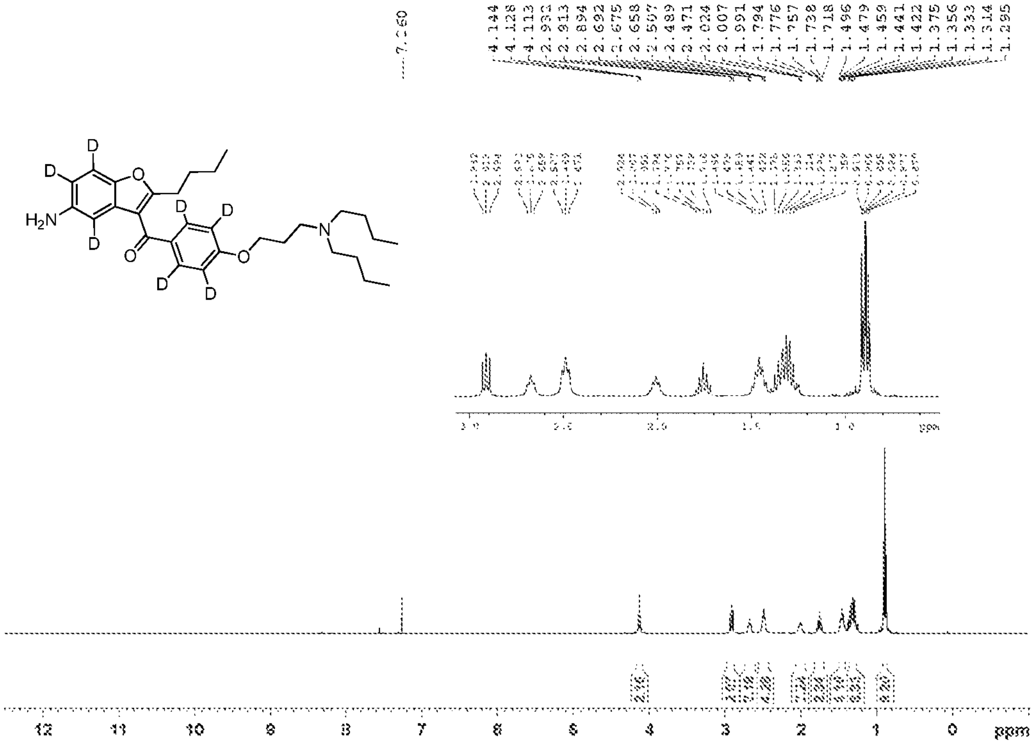

FIG. 50. Shows the $^1$H NMR spectra of (5-amino-2-butyl-1-benzo(4,6,7-$d_3$)furan-3-yl)(4-(3-(dibutylamino) propoxy) phenyl(2,3,5,6-$d_4$))methanone (DD7) prepared according to the synthetic scheme shown schematically in FIG. 43.

Figure 51:
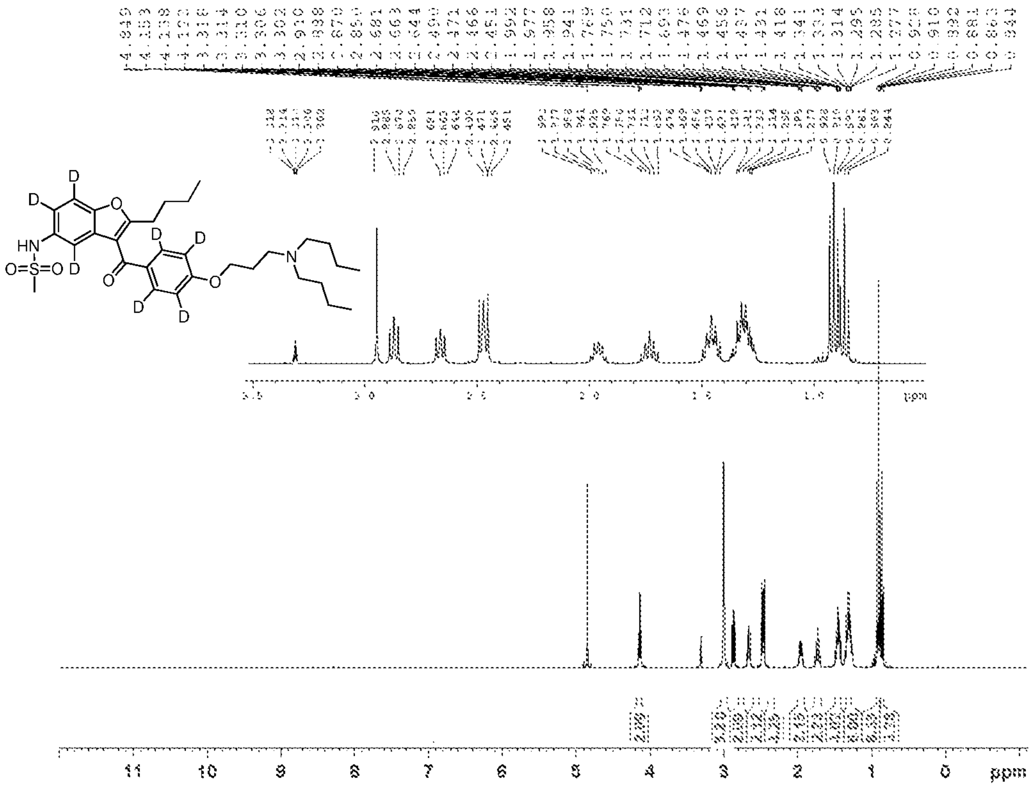

FIG. 51. Shows the $^1$H NMR spectra of Methanesulfonamide, N-(2-butyl-3-(4-(3-(dibutylamino) propoxy) benzoyl (2,3,5,6-$d_4$))-1-benzofuran-5-yl) (DD8) prepared according to the synthetic scheme shown schematically in FIG. 43.

Figure 52:
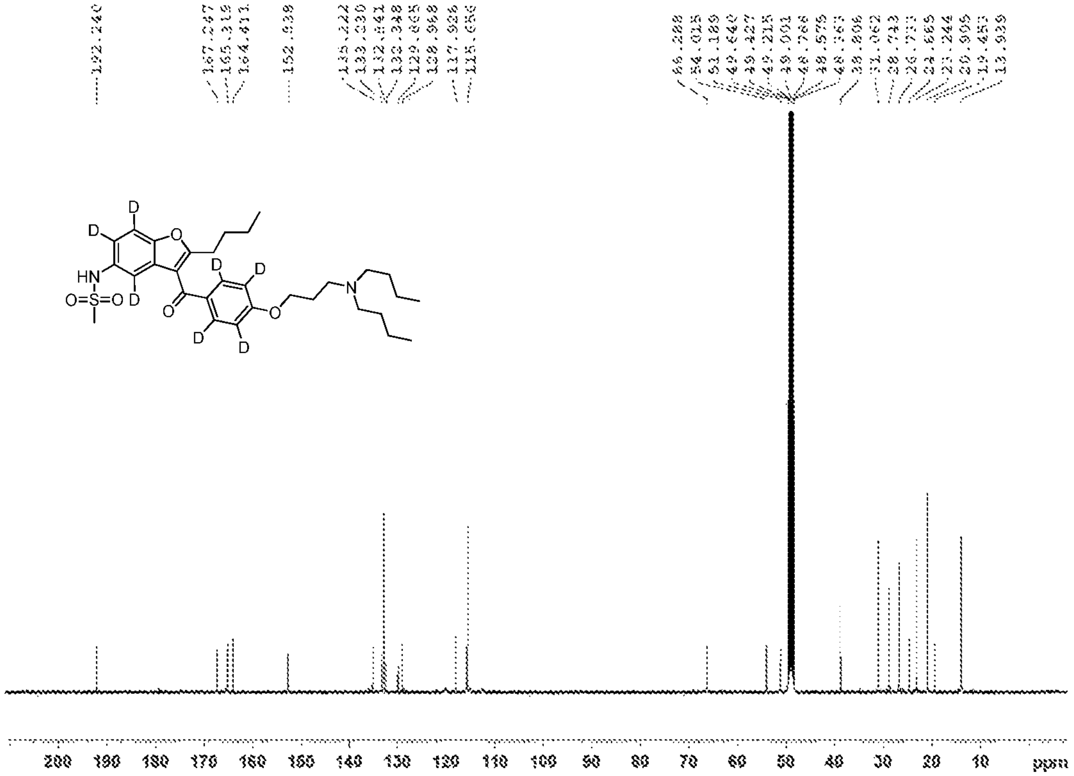

FIG. 52. Shows the $^{13}$C NMR spectra of Methanesulfonamide, N-(2-butyl-3-(4-(3-(dibutylamino) propoxy) benzoyl (2,3,5,6-$d_4$))-1-benzofuran-5-yl) (DD8) prepared according to the synthetic scheme shown schematically in FIG. 43.

Table 1. siRNA Target sequences and qPCR primer list.

Table 2. Compound-dependent MS parameters of O-desmethylastemizole and buspirone.

Table 3. MBI of CYP2J2-mediated metabolism of rivaroxaban.

Table 4. Forward and reverse sequences of primers for human CYP2J2, EPHX2 and GAPDH genes.

Table 5. Optimized LC-MS/MS conditions for the quantitation of dronedarone, poyendarone and NDEA (IS) in dog plasma. (A): Source-dependent parameters; (B): Compound-dependent parameters. Q1: mass of parent ion; Q3: mass of daughter ion; DP: declustering potential; EP: entrance potential; CE: collision energy; CXP: cell exit potential.

Table 6. Results of substrate depletion and time- and concentration-dependent inactivation.

Table 7. Parameters used for PBPK modelling.

Table 8. Calculated Log P (c Log P; calculated using ChemSketch), aqueous solubility (measured in universal buffer (pH 7.4) using MultiscreenHTS PCF Filter Plates34), effective permeability (measured using parallel artificial membrane permeability assay) and in-vitro metabolic half-life (T½; measured using recombinant CYP2J2, NADPH, 1 μM drug) of poyendarone versus dronedarone.

Table 9. Comparison of the effects of antiarrhythmic drugs on the atrial (ΔAERP) and ventricular (ΔVERP) effective refractory periods. Atrial selectivity is measured based on the ratio of ΔAERP to ΔVERP (ΔAERP/ΔVERP) where poyendarone=dronedarone>amiodarone>bepridil>dl-sotalol.

Table 10. Comparison of the effects of antiarrhythmic drugs on terminal repolarization periods (ΔTRP), early (ΔJ-Tpeakc) and late (ΔTpeak-Tend) repolarization periods. ΔTRP is indicative of risk of re-entrant ventricular arrhythmias where dronedarone>bepridil>dl-sotalol>amiodarone>poyendarone.

SEQUENCE LISTING

The Sequence Listing is submitted as an ASCII text filed in the form of the file name "Sequence.txt" (~3 kb), which was created on Dec. 23, 2021, and which is incorporated by reference herein.

Materials and Methods

All reagents and solvents were of general purpose or analytical grade and were purchased from Merck (previously Sigma-Aldrich), unless indicated otherwise. Reactions were routinely monitored by thin-layer chromatography (TLC) on silica gel plate (precoated 60 F254 Merck plate). Column chromatography was performed using silica gel 60 (Merck, 70-230 mesh). Compounds were dissolved in HPLC (high performance liquid chromatography) grade methanol for determination of mass to charge m/z on a ABSciex 2000, LC/MS/MS mass spectrometer (source of ionization: Electrospray ionization (ESI) probe). $^1$H NMR spectra was determined in the deuterated chloroform ($CDCl_3$) deuterated dimethylsufoxide (DMSO-$d_6$) and deuterated methanol (MeOH-$d_4$) solutions on a Bruker DPX ultrashield NMR (400 MHz) spectrometer, with chemical shifts quoted in parts per million (δ) downfield relative to tetramethylsilane (TMS) as internal standard, and J values (coupling constants) given in hertz. The following abbreviations were used: s, singlet; d, doublet; t, triplet; m, multiplet.

Details of the synthesis of the hydrochloride salt of poyendarone ('poyendarone HCl') are provided below.

Experimental Detail for the Synthesis of Poyendarone HCl as Shown Schematically in FIG. 5

Synthesis of 2-(bromomethyl)-4-nitrophenol(3,5,6-$d_3$) (D1). Conc. Sulfuric acid (0.121 ml) was added to a mixture of 4-nitro(2,3,5,6-$d_4$)phenol (1.25 g, 0.00873 M) and 48% HBr solution (15.8 ml) at room temperature, followed by 35% formalin solution (0.760 g, 0.0244 M, 2.8 eq). The reaction mixture was heated at 75° C. with stirring for 6 hrs. Following which the reaction mixture was poured slowly into ice water mixture and stirred for 1 hr. The obtained solid was filtered, washed with cold water and then dried under vacuum to obtain a beige solid. Toluene (50 ml) was added to the solid and the mixture was heated with stirring at 85° C. for 1 hr. The mixture was cooled to 5° C. and stirred for 1 hr at the same temperature. The resulting solid was filtered, washed with toluene and then dried under vacuum to get a white solid as product. Yield: 76.5%, $^1$H NMR (400 MHz, DMSO-$d_6$): δ 4.70 (s, 2H), 11.61 (s, 1H). The $^1$H NMR spectra of the synthesised product is shown in FIG. 34.

Synthesis of 2-((bromotriphenylphosphoranyl)methyl)-4-nitrophenol(3,5,6-$d_3$) (D2). To a solution of 1.5 g (0.00638 M) of 2-(bromomethyl)-4-nitrophenol(3,5,6-$d_3$) (D1) in toluene (10 ml) was added 1.67 g of triphenyl phosphine (0.00638 M) and the mixture was refluxed for 1 hr. After completion of the reaction, the mixture was cooled and the resulting precipitate was filtered. The filtrate was evaporated to dryness and stirred with toluene (10 ml) for 30 min and filtered to obtain a solid. Both solids were combined and dried under vacuum to obtain a white solid. Yield: 99.0%, $^1$H NMR (400 MHz, $CDCl_3$): δ 4.76-4.80 (d, J=14.0 Hz, 2H), 7.57-7.66 (m, 12H), 7.78-7.82 (m, 3H). The $^1$H NMR spectra of the synthesised product is shown in FIG. 35.

Synthesis of 2-butyl-5-nitro-1-benzo(4,6,7-$d_3$)furan (D3). To a solution of 1.65 g (0.00332 M) of 2-((bromotriphenylphosphoranyl)methyl)-4-nitrophenol(3,5,6-$d_3$) (D2) in 10 ml of $CHCl_3$ was added 0.522 g (0.0066 M, 2 eq) of pyridine. To the mixture was then slowly added 0.500 g (0.00405 M, 1.25 eq) of valeroyl chloride with stirring at room temperature. The mixture was refluxed for 2 hrs and then 25 ml of toluene was added and about half of the solvent was evaporated under reduced pressure. 1.0 g (0.00996M, 3 eq) of triethylamine was then added and refluxed for a further 3 hrs. The resulting reaction mixture was cooled and the triphenyl phosphine oxide formed was filtered, washed with ethyl acetate and the filtrate was concentrated under vacuum. The viscous residue formed was purified by column chromatography using Pet. Ether: EtOAc (95:5) to obtain a colorless residue. Yield: 73.5%, $^1$H NMR (400 MHz, $CDCl_3$): δ 0.85-0.89 (t, J=7.20 Hz, 3H), 1.28-1.38 (m, 2H), 1.70-1.78 (m, 2H), 2.87-2.91 (t, J=7.60 Hz, 2H), 7.53-7.55 (d, J=8.80 Hz, 1H). The $^1$H NMR spectra of the synthesised product is shown in FIG. 36.

Synthesis of (2-butyl-5-nitro-1-benzo(4,6,7-$d_3$)furan-3-yl)(4-methoxyphenyl)methanone (D4). To a solution of 2-butyl-5-nitro-1-benzo(4,6,7-$d_3$)furan (D3) (1.4 g, 0.00629 M) in 15 ml dichloromethane (7 ml) was added 4-methoxybenzoyl chloride (1.61 g, 0.00945 M, 1.5 eq) and tin(IV) chloride (4.1 g, 0.0157 M, 2.5 eq) slowly over 1 h at 0-5° C. and stirring was continued for 24 h at room temperature. The reaction mixture was cooled at 0-5° C. following which water (10 ml) was added slowly and the mixture was stirred for about 30 min. The aqueous layer was separated and extracted with dichloromethane (3×10 ml). The combined organic layer was evaporated under reduced pressure. The crude compound obtained was purified by column chromatography using Pet.Ether:EtOAc (85:15) to obtain a white solid as product. Yield: 93.5%, $^1$H NMR (400 MHz, $CDCl_3$): δ 0.86-0.89 (t, J=7.40 Hz, 3H), 1.29-1.38 (m, 2H), 1.71-1.78 (m, 2H), 2.88-2.92 (t, J=7.60 Hz, 2H), 3.90 (s, 3H), 6.96-6.99 (d, J=8.80 Hz, 2H), 7.80-7.83 (d, J=8.80 Hz, 2H). The $^1$H NMR spectra of the synthesised product is shown in FIG. 37.

Synthesis of (2-butyl-5-nitro-1-benzo(4,6,7-$d_3$)furan-3-yl)(4-hydroxyphenyl)methanone (D5). To a solution of 1.02 g (0.00286 M) of (2-butyl-5-nitro-1-benzo(4,6,7-$d_3$)furan-3-yl)(4-methoxyphenyl)methanone (D4) in dichloromethane (50 ml) was added $AlCl_3$ (2.29 g, 0.0172 M, 6 eq) slowly over 1 h with stirring at 0-5° C. The mixture was refluxed for 24 h and cooled to room temperature and then to 0-5° C. Water (10 ml) was added slowly and the mixture was stirred for about 30 min. The organic layer was separated and concentrated under vacuum to give a residue which was purified by column chromatography using Pet Ether: EtOAc (90:10) to obtain a yellowish oil. Yield: 98.0%, $^1$H NMR (400 MHz, $CDCl_3$): δ 0.87-0.90 (t, J=7.20 Hz, 3H), 1.30-1.39 (m, 2H), 1.72-1.80 (m, 2H), 2.90-2.94 (t, J=7.60 Hz, 2H), 6.94-6.96 (d, J=8.80 Hz, 2H), 7.77-7.80 (d, J=8.80 Hz, 2H). The $^1$H NMR spectra of the synthesised product is shown in FIG. 38.

Synthesis of (2-butyl-5-nitro-1-benzo(4,6,7-$d_3$)-furan-3-yl)(4-(3-(dibutylamino) propoxy) phenyl)methanone (D6). To a solution of 0.800 g (0.0023M) of (2-butyl-5-nitro-1-benzo(4,6,7-$d_3$)furan-3-yl)(4-hydroxyphenyl)methanone (D5) in 20 ml of acetone was added 3.23 g (0.0023M, 1 eq) of anhydrous $K_2CO_3$ and 4.79 g (0.0023 M, 1 eq) of 1-chloro-3-di-n-butylaminopropane at room temperature. The reaction mixture was refluxed at 60° C. overnight. The reaction mixture was cooled and evaporated under reduced pressure. To the resulting solid, water (20 ml) was added and stirred for 5 min and extracted with dichloromethane (3×20 ml). The organic layer was evaporated under reduced pressure to obtain a crude residue which was further purified by column chromatography using Pet Ether: EtOAc (70:30) to obtain a yellowish oily residue. Yield: 77.0%, 1H NMR (400 MHz, DMSO-$d_6$): δ 0.80-0.84 (m, 9H), 1.22-1.27 (m, 6H), 1.30-1.37 (m, 4H), 1.64-1.72 (m, 2H), 1.82-1.85 (t, J=6.40 Hz, 2H), 2.33-2.36 (t, J=7.00 Hz, 4H), 2.51-2.53 (m, 2H), 2.82-2.86 (t, J=7.60 Hz, 2H), 4.12-4.15 (t, J=6.00 Hz, 2H), 7.08-7.10 (d, J=8.80 Hz, 2H), 7.81-7.83 (d, J=8.80 Hz, 2H). The $^1$H NMR spectra of the synthesised product is shown in FIG. 39.

Synthesis of (5-amino-2-butyl-1-benzo(4,6,7-$d_3$)-furan-3-yl)(4-(3-(dibutylamino) propoxy) phenyl)methanone (D7). A mixture of 0.114 g (0.00022 M) of (2-butyl-5-nitro-1-benzo(4,6,7-$d_3$)furan-3-yl)(4 (3(dibutylamino)propoxy)phenyl) methanone (D6), 0.106 g (0.00133 M, 6 eq) of iron powder, 0.5 ml of ethanol and 0.25 ml of water was stirred at room temperature for 10 min. The reaction mixture was cooled to 15° C. and 0.5 ml of conc. HCl was added. The reaction mixture was stirred for 3 hrs at 65° C., cooled, poured into ice water mixture and stirred for 30 min. The aqueous layer was extracted with dichloromethane (3×5 ml). The pH of the organic layers was adjusted to 8-9 using aqueous ammonia solution. Both the organic and aqueous layers were separated. The aqueous layer was extracted with dichloromethane (3×5 ml) and both the organic layers were combined and dried with $Na_2SO_4$ and removed under reduced pressure to obtain a colorless oil. Yield: 80.3%, $^1$H NMR (400 MHz, $CDCl_3$): δ 0.87-0.91 (m, 9H), 1.25-1.37 (m, 6H), 1.42-1.49 (m, 4H), 1.71-1.79 (m, 2H), 1.99-2.02 (m, 2H), 2.47-2.50 (m, 4H), 2.65-2.69 (m, 2H), 2.89-2.93 (t, J=7.60 Hz, 2H), 4.11-4.14 (t, J=6.20 Hz, 2H), 6.96-6.98 (d, J=8.80 Hz, 2H), 7.80-7.82 (d, J=8.80 Hz, 2H). The $^1$H NMR spectra of the synthesised product is shown in FIG. 40.

Synthesis of Methanesulfonamide, N-(2-butyl-3-(4-(3-(dibutylamino) propoxy)benzoyl)-1-benzo(4,6,7-$d_3$)-furan-5-yl)hydrochloride (D8). To a warmed solution of 0.100 g (0.000207 M) of (5-amino-2-butyl-1-benzo(4,6,7-$d_3$)furan-3-yl)(4-(3 (dibutylamino)propoxy)phenyl) methanone (D7) in anhydrous dichloromethane (3 ml) was added 0.0197 g (0.000249 M, 1.2 eq) of pyridine and 0.028 g (0.000249 M, 1.2 eq) of methane sulfonylchloride slowly over 5 min at 35° C. The resulting mixture was stirred at the same temperature for 3 h and then cooled to room temperature. This mixture was then washed with 2×5 ml of water and 2×5 ml of 5% $NaHCO_3$ solution and 1×5 ml of water. The organic phase was separated and concentrated, which was further purified by column chromatography using Pet Ether: EtOAc (10:90) to obtain a brown oily residue in 80% yield. To this residue 5 ml of methanol was added and a solution of hydrochloric acid (0.100 ml) in 0.4 ml of methanol was added over 20 min. The reaction mixture was stirred for 3 h at 0° C. and the obtained solid was filtered and washed with methanol and dried to obtain the title compound as pale brown solid. ESI-MS (m/z) calculated for $C_{31}H_{41}D_3N_2O_5S$ $[M+H]^+$ 559.77. Yield: 79.0%, $^1$H NMR (400 MHz, MeOH-$d_4$): δ 0.83-0.88 (m, 3H), 0.89-0.93 (t, J=7.20 Hz, 6H), 1.27-1.33 (m, 6H), 1.43-1.47 (m, 4H), 1.69-1.77 (m, 2H), 1.94-1.99 (m, 2H), 2.45-2.49 (m, 4H), 2.64-2.68 (t, J=7.40 Hz, 2H), 2.86-2.89 (t, J=7.60 Hz, 2H), 2.96 (s, 3H), 4.12-4.16 (t, J=6.00 Hz, 2H), 7.03-7.06 (d, J=8.8 Hz, 2H), 7.78-7.87 (d, J=9.2 Hz, 2H), $^{13}$C NMR (400 MHz, MeOH-$d_4$): 13.7, 19.5, 20.7, 23.2, 24.7, 26.7, 28.7, 31.1, 38.8, 51.2, 54.0, 66.3, 115.6, 117.9, 128.9, 129.7, 132.3, 132.7, 133.3, 135.5, 152.7, 163.9, 165.5, 167.5, 192.5. The $^1$H and $^{13}$C NMR spectra of the synthesised product is shown in FIGS. 41 and 42, respectively.

Experimental Detail for the Synthesis of the Deuterated Dronedarone Derivative 'Compound 3' as Shown Schematically in FIG. 43

Synthesis of 2-(bromomethyl)-4-nitrophenol (2,3,5,6-$d_4$) (DD-1). Conc.

Sulfuric acid (0.121 ml) was added to a mixture of 4-nitrophenol (2,3,5,6-$d_4$) (1.25 g, 0.00873 M) and 48% HBr solution (15.8 ml) at room temperature, followed by 35% formalin solution (0.760 g, 0.0244 M, 2.8 eq). The reaction mixture was heated at 75° C. with stirring for 6 hrs. Following which the reaction mixture was poured slowly into ice water mixture and stirred for 1 hr. The obtained solid was filtered, washed with cold water and then dried under vacuum to obtain a beige solid. Toluene (50 ml) was added to the solid and the mixture was heated with stirring at 85° C. for 1 hr. The mixture was cooled to 5° C. and stirred for 1 hr at the same temperature. The resulting solid was filtered, washed with toluene and then dried under vacuum to get a white solid as product. Yield: 76.0%, $^1$H NMR (400 MHz, DMSO-$d_6$): δ 11.64 (s, 1H). The $^1$H NMR spectra of the synthesised product is shown in FIG. 44.

Synthesis of 2-((bromotriphenylphosphoranyl)methyl)-4-nitrophenol (2,3,5,6-$d_4$)(DD-2). To a solution of 1.5 g (0.00638 M) of 2-(bromomethyl)-4-nitrophenol (2,3,5,6-$d_4$) (DD-1) in toluene (10 ml) was added 1.67 g of triphenyl phosphine (0.00638 M) and the mixture was refluxed for 1 hr. After completion of the reaction, the mixture was cooled and the resulting precipitate was filtered. The filtrate was evaporated to dryness and stirred with toluene (10 ml) for 30 min and filtered to obtain a solid. Both solids were combined and dried under vacuum to obtain a white solid. Yield: 98.0%, $^1$H NMR (400 MHz, $CDCl_3$): δ 4.70-4.74 (d, J=14.0 Hz, 2H). The $^1$H NMR spectra of the synthesised product is shown in FIG. 45.

Synthesis of 2-butyl-5-nitro-1-benzo (4,6,7-$d_3$) furan (DD-3). To a solution of 1.65 g (0.00334 M) of 2-((bromotriphenylphosphoranyl)methyl)-4-nitrophenol (2,3,5,6-$d_4$) (DD-2) in 10 ml of $CHCl_3$ was added 0.522 g (0.00663 M, 2 eq) of pyridine. To the mixture was then slowly added 0.500 g (0.00417 M, 1.25 eq) of valeroyl chloride with stirring at room temperature. The mixture was refluxed for 2 hrs and then 25 ml of toluene was added and about half of the solvent was evaporated under reduced pressure. 1.0 g (0.01002M, 3 eq) of triethylamine was then added and refluxed for a further 3 hrs. The resulting reaction mixture was cooled and the triphenyl phosphine oxide formed was filtered, washed with ethyl acetate and the filtrate was concentrated under vacuum. The viscous residue formed was purified by column chromatography using Pet. Ether: EtOAc (95:5) to obtain a colorless residue. Yield: 75.0%, $^1$H NMR (400 MHz, $CDCl_3$): δ 0.75-0.95 (t, J=7.20 Hz, 3H), 1.15-1.36 (m, 2H), 1.45-1.67 (m, 2H), 2.30-2.80 (t, J=7.60 Hz, 2H), 5.82 (s, 1H). The $^1$H NMR spectra of the synthesised product is shown in FIG. 46.

Synthesis of (2-butyl-5-nitro-1-benzo(4,6,7-$d_3$)furan-3-yl)(4-methoxyphenyl (2,3,5,6-$d_4$))methanone (DD-4). To a solution of 2-butyl-5-nitro-1-benzo (4,6,7-$d_3$) furan (DD-3) (1.4 g, 0.00630M) in 15 ml dichloromethane (7 ml) was added 4-methoxybenzoyl ($d_4$) chloride (1.61 g, 0.00958 M, 1.5 eq) and tin(IV) chloride (4.1 g, 0.0157 M, 2.5 eq) slowly over 1 h at 0-5° C. and stirring was continued for 24 h at room temperature. The reaction mixture was cooled at 0-5° C. following which water (10 ml) was added slowly and the mixture was stirred for about 30 min. The aqueous layer was separated and extracted with dichloromethane (3×10 ml). The combined organic layer was evaporated under reduced pressure. The crude compound obtained was purified by column chromatography using Pet.Ether:EtOAc (85:15) to obtain a white solid as product. Yield: 95.0%, $^1$H NMR (400 MHz, $CDCl_3$): δ 0.86-0.89 (t, J=7.40 Hz, 3H), 1.29-1.38 (m, 2H), 1.71-1.79 (m, 2H), 2.88-2.92 (t, J=7.60 Hz, 2H), 3.90 (s, 3H). The $^1$H NMR spectra of the synthesised product is shown in FIG. 47.

Synthesis of (2-butyl-5-nitro-1-benzo(4,6,7-$d_3$) furan-3-yl)(4-hydroxyphenyl (2,3,5,6-$d_4$)) methanone (DD-5). To a solution of 1.02 g (0.000283 M) of (2-butyl-5-nitro-1-benzo (4,6,7-$d_3$)furan-3-yl)(4-methoxyphenyl (2,3,5,6-$d_4$) methanone (DD-4) in dichloromethane (50 ml) was added $AlCl_3$ (2.29 g, 0.0169 M, 6 eq) slowly over 1 h with stirring at 0-5° C. The mixture was refluxed for 24 h and cooled to room temperature and then to 0-5° C. Water (10 ml) was added slowly and the mixture was stirred for about 30 min. The organic layer was separated and concentrated under vacuum to give a residue which was purified by column chromatography using Pet Ether: EtOAc (90:10) to obtain a yellowish oil. Yield: 98.0%, $^1$H NMR (400 MHz, $CDCl_3$): δ 0.87-0.90 (t, J=7.20 Hz, 3H), 1.30-1.39 (m, 2H), 1.72-1.80 (m, 2H), 2.90-2.94 (t, J=7.60 Hz, 2H). The $^1$H NMR spectra of the synthesised product is shown in FIG. 48.

Synthesis of (2-butyl-5-nitro-1-benzo(4,6,7-$d_3$)furan-3-yl)(4-(3-(dibutylamino) propoxy) phenyl (2,3,5,6-$d_4$)) methanone (DD-6). To a solution of 0.800 g (0.00231 M) of (2-butyl-5-nitro-1-benzo(4,6,7-$d_3$)furan-3-yl)(4-hydroxyphenyl(2,3,5,6-$d_4$)) methanone (DD-5) in 20 ml of acetone was added 3.23 g (0.00231 M, 1 eq) of anhydrous $K_2CO_3$ and 4.79 g (0.00231 M, 1 eq) of 1-chloro-3-di-n-butylaminopropane at room temperature. The reaction mixture was refluxed at 60° C. overnight. The reaction mixture was cooled and evaporated under reduced pressure. To the resulting solid, water (20 ml) was added and stirred for 5 min and extracted with dichloromethane (3×20 ml). The organic layer was evaporated under reduced pressure to obtain a crude residue which was further purified by column chromatography using Pet Ether: EtOAc (70:30) to obtain a yellowish oily residue. Yield: 79.0%, $^1$H NMR (400 MHz, DMSO-$d_6$): δ 0.81-0.84 (m, 9H), 1.22-1.27 (m, 6H), 1.30-1.37 (m, 4H), 1.64-1.70 (m, 2H), 1.83-1.86 (t, J=6.40 Hz, 2H), 2.33-2.37 (t, J=7.00 Hz, 4H), 2.50-2.53 (m, 2H), 2.82-2.86 (t, J=7.60 Hz, 2H), 4.12-4.16 (t, J=6.00 Hz, 2H). The $^1$H NMR spectra of the synthesised product is shown in FIG. 49.

Synthesis of (5-amino-2-butyl-1-benzo(4,6,7-$d_3$)furan-3-yl)(4-(3-(dibutylamino) propoxy) phenyl(2,3,5,6-$d_4$))methanone (DD-7). A mixture of 0.114 g (0.00023 M) of (2-butyl-5-nitro-1-benzo(4,6,7-$d_3$)furan-3-yl)(4-(3-(dibutylamino) propoxy) phenyl (2,3,5,6-$d_4$))methanone (DD-6) 0.106 g (0.00138 M, 6 eq) of iron powder, 0.5 ml of ethanol and 0.25 ml of water was stirred at room temperature for 10 min. The reaction mixture was cooled to 15° C. and 0.5 ml of conc. HCl was added. The reaction mixture was stirred for 3 hrs at 65° C., cooled, poured into ice water mixture and stirred for 30 min. The aqueous layer was extracted with dichloromethane (3×5 ml). The pH of the organic layers was adjusted to 8-9 using aqueous ammonia solution. Both the organic and aqueous layers were separated. The aqueous layer was extracted with dichloromethane (3×5 ml) and both the organic layers were combined and dried with $Na_2SO_4$ and removed under reduced pressure to obtain a colorless oil. Yield: 82.0%, $^1$H NMR (400 MHz, $CDCl_3$): δ 0.87-0.91 (m. 9H), 1.26-1.37 (m, 6H), 1.42-1.49 (m, 4H), 1.71-1.79 (m, 2H), 1.99-2.02 (m, 2H), 2.47-2.51 (m, 4H), 2.66-2.69 (m, 2H), 2.89-2.93 (t, J=7.60 Hz, 2H), 4.11-4.14 (t, J=6.20 Hz, 2H). The $^1$H NMR spectra of the synthesised product is shown in FIG. 50.

Synthesis of Methanesulfonamide, N-(2-butyl-3-(4-(3-(dibutylamino) propoxy) benzoyl (2,3,5,6-$d_4$))-1-benzofuran-5-yl)(DD-8). To a warmed solution of 0.100 g (0.000206 M) of (5-amino-2-butyl-1-benzo(4,6,7-$d_3$)furan-3-yl)(4-(3-(dibutylamino) propoxy) phenyl(2,3,5,6-$d_4$)) methanone (DD-7) in anhydrous dichloromethane (3 ml) was added 0.0197 g (0.000247 M, 1.2 eq) of pyridine and 0.028 g (0.000247 M, 1.2 eq) of methane sulfonylchloride slowly over 5 min at 35° C. The resulting mixture was stirred at the same temperature for 3 h and then cooled to room temperature. This mixture was then washed with 2×5 ml of water and 2×5 ml of 5% $NaHCO_3$ solution and 1×5 ml of water. The organic phase was separated and concentrated, which was further purified by column chromatography using Pet Ether: EtOAc (10:90) to obtain a brown oily residue in 80% yield. To this residue 5 ml of methanol was added and a solution of hydrochloric acid (0.100 ml) in 0.4 ml of methanol was added over 20 min. The reaction mixture was stirred for 3 h at 0° C. and the obtained solid was filtered and washed with methanol and dried to obtain the title compound as pale brown solid. ESI-MS (m/z) calculated for $C_{31}H_{37}D_7N_2O_5S$ $[M+H]^+$ 563.8. Yield: 80.0%, $^1$H NMR (400 MHz, MeOH-$d_4$): δ 0.84-0.88 (m, 3H), 0.89-0.93 (t, J=7.20 Hz, 6H), 1.27-1.34 (m, 6H), 1.42-1.49 (m, 4H), 1.69-1.76 (m, 2H), 1.92-1.99 (m, 2H), 2.45-2.49 (m, 4H), 2.64-2.68 (t, J=7.40 Hz, 2H), 2.85-2.88 (t, J=7.60 Hz, 2H), 2.91 (s, 3H), 4.12-4.15 (t, J=6.00 Hz, 2H). $^{13}$C NMR (400 MHz, MeOH-$d_4$): 13.9, 19.4, 20.9, 23.2, 24.6, 26.7, 28.7, 31.0, 38.8, 51.1, 54.0, 66.2, 115.6, 117.9, 128.9, 129.8, 132.3, 132.8, 133.2, 135.2, 152.8, 164.4, 165.3, 167.2, 192.2. The $^{1}$H and $^{13}$C NMR spectra of the synthesised product is shown in FIGS. 51 and 52, respectively.

In Vitro Assessment of CYP2J2 Expression on Cardiac Beat to Beat Intervals (A) Cell Culture. The human ES cell line (H7 ESCs) with a knocked in, constitutively expressed Genetically Encoded Calcium Indicator (GECI) GCaMP6s was maintained on matrigel coated plates in StemMACS™ iPS-Brew XF (Miltenyi Biotec) cell culture medium, and passaged in clumps using Collagenase IV (1 mg/mL) enzymatic treatment. For differentiation, ESCs were passaged in single cells using Accutase® (Nacalai Tesque) cell detachment solution, and subjected to the previously established small molecule based GiWi cardiomyocyte differentiation protocol. At Day 7, the media was replaced with RPMI1640 (HyClone) supplemented with B27 with insulin (B27+) (Miltenyi Biotec) for maturation and refreshed every 2 days. At Day 21, the glucose level in the media was slowly reduced to 0% by Day 28 to facilitate the metabolic selection of more matured cardiomyocytes that rely on β-oxidation. The cardiomyocytes (H7 CMs) were used for siRNA transfections on day 28.

(B) siRNA knockdown of CYP2J2. A set of four self-delivery modified Accell™-siRNAs (Table 1) and delivery media (Cat #B-005000) were obtained from Dharmacon™. Transfection was carried out on adherent cells in accordance to the supplier's protocol. Briefly, individual wells of Day 28 H7 CMs were treated with 1 μM of an individual siRNA or 0.25 μM of all four siRNAs (Pooled condition) in Accell™ siRNA Delivery Media for 72 h. The delivery media was replaced with low glucose B27+ media for 24 h before video analysis and RNA harvesting for qPCR analysis.

(C) RNA isolation. For each treatment, ~$5\times10^6$ cells were harvested and lysed in 500 μL of TRIzol reagent (Invitrogen). The samples were allowed to stand for 5 min at room temperature, after which 180 μL of chloroform (Kanto Chemical, Japan) was added, followed centrifugation at 12,000×g for 15 min at 4° C. for phase separation. Next, the aqueous phase was transferred to a fresh tube with equal volumes of isopropanol and GlycoBlue™ Coprecipitant (Invitrogen, U.S.A.) blue dye. The samples were incubated at room temperature for 20 min. The samples were pelleted through centrifugation at 12,000×g for 15 min at 4° C. The RNA pellet was washed with 100% ethanol, air-dried before reconstituting it in nuclease-free water (Ambion, U.S.A.).

(D) Quantitative PCR. RNA samples (250 ng) were reverse transcribed to obtain cDNA using High-Capacity cDNA Reverse Transcription Kit (Applied Biosystems, U.S.A.). qPCR was performed using the FAST SYBR™ Green Mix (Applied Biosystems, U.S.A.) master mix for qPCR on 5 ng of cDNA. $\Delta\Delta C_T$-based relative quantification method was adopted for qPCR analysis using the QuantStudio 5 384-well Block Real-Time PCR system (Applied Biosystems, U.S.A.). The threshold cycle was determined to be ≥35. Data is presented as fold-change where CT values were normalised to β-ACTIN. Data presented are representative of two independent experiments with error bars indicative of the standard deviation (SD) unless otherwise stated.

Results are shown in FIG. 6.

(E) Fluorescent $Ca^{2+}$ imaging and video analysis of GCaMP6s H7 CMs. Calcium transients of H7 CMs post treatment were imaged using a Nikon® ECLIPSE Ti-S fluorescent microscope and recorded using an Andor Zyla 4.2 sCMOS camera at 15 fps. Video data was analysed using Nikon®'s NIS-Elements AR and processed using RStudio v1.2.1335 to identify fluorescent peaks corresponding to single cardiac contractions and compute relevant data to obtain beat to beat intervals and variations.

Results are shown in FIG. 7 and FIG. 8.

(F) Statistical analysis. GraphPad Prism 7 software was used to plot the data points and carry out statistical analysis. Knockdown efficiency of siRNA treatment was assessed using Student's t-test. Comparison of beat to beat variation between treatment groups was assessed using the nonparametric Mann-Whitney U test. Statistical significance is set as $p<0.05$.

Results are shown in FIG. 9.

In Vitro Time-, Concentration-, and NADPH-Dependent Inactivation of CYP2J2 by Dronedarone and Poyendarone (A) Reagents. High-performance liquid chromatography (HPLC)-grade acetonitrile (ACN) was purchased from Tedia Company Inc. (Fairfield, OH). Dronedarone hydrochloride, astemizole and buspirone hydrochloride were purchased from Sigma-Aldrich (St. Louis, MO); human recombinant CYP2J2 Supersomes™ (rCYP2J2) and a NADPH regenerating system consisting of NADPH A (NADP+ and glucose 6-phosphate) and B (glucose-6-phosphate dehydrogenase) were purchased from BD Gentest (Woburn, MA). Poyendarone hydrochloride was synthesized in-house according to the synthesis detailed herein. Water was obtained using a Milli-Q® water purification system (Millipore, Billerica, MA). All other reagents were of analytical grade.

(B) Time-, Concentration-, and NADPH-Dependent Inactivation of CYP2J2 by Dronedarone and Poyendarone using Astemizole as Probe Substrate. Primary incubation mixtures (100 μL) comprising varying concentrations of dronedarone (0-1.0 μM) or poyendarone (0-10.0 μM), 20 pmol/mL rCYP2J2, 100 mM potassium phosphate buffer (pH 7.4) and NADPH B were warmed at 37° C. for 3 to 5 min. The enzymatic reaction was initiated by adding NADPH A. At different pre-incubation time points (0, 3, 8, 15, 22, 30, 45 min), 10 μL aliquots of the primary incubation mixture were transferred to a pre-warmed 90 μL secondary incubation mixture comprising the buffer, astemizole (15 μM) and NADPH regenerating system to give a 10-fold dilution. Then the secondary incubation mixtures were further incubated for 15 min at 37° C. before 70 μL aliquots were removed and quenched using ice-cold ACN containing 0.1 μM buspirone hydrochloride (internal standard). The samples were centrifuged at 2755 g at 4° C. for 30 min, and the supernatants were used for the determination of O-desmethylastemizole by liquid chromatography tandem mass spectrometry (LC/MS/MS) analysis. For a negative control, NADPH A was replaced with 100 mM potassium phosphate buffer. The LC/MS/MS system consisted of an Agilent 1290 Infinity ultra-high pressure liquid chromatography (UHPLC) system (Agilent Technologies Inc., Santa Clara, CA) interfaced with the AB SCIEX QTRAP® 5500 tandem mass spectrometry (MS/MS) system (AB SCIEX, Framingham, MA). The LC/MS/MS system was controlled by Analyst 1.4.2 software (Applied Biosystems) which performed all chromatographic peak integration. The ACQUITY UPLC BEH C18 column, 1.7 μM, 2.1×50 mm (Waters, Milford, MA), was used to achieve chromatographic separation. The temperatures of the column and samples were maintained at 45° C. and 4° C. respectively. The mobile phases used were 0.2% acetic acid in 5 mM ammonium acetate in water (solvent A) and 0.2% acetic acid in ACN (solvent B). They were delivered at a flow rate of 0.6 mL/min. The elution conditions were optimized as follows: linear gradient 30 to 95% B (0-1.60 min), isocratic at 95% B (1.61-1.99 min), and isocratic at 30% B (2.00-2.50 min).). Multiple reaction monitoring (MRM) transitions of mass-to-charge (m/z) ratios from 445 to 121 and 386 to 122 were carried out in the positive electrospray ionization (ESI) mode to detect O-desmethylastemizole and buspirone respectively. The MS source conditions were: curtain gas, 25 psi; collision gas, medium; ionspray voltage, 5500 V; temperature, 550° C.; ion source gas 1, 50 psi; and ion source gas 2, 55 psi. The compound-dependent mass spectrometry (MS) parameters of O-desmethylastemizole and buspirone are summarized in Table 2.

(C) Calculation of Kinetic Parameters. To calculate the inactivation kinetic parameters, the mean of the peak area ratios of the triplicates were normalized to 0 min with respect to pre-incubation time. The percentage probe activity remaining was calculated and the natural logarithmic activity was plotted against pre-incubation time. The data was fitted to linear regression and the slope of the graphs determines the observed rate of inactivation ($K_{obs}$). The kinetic parameters $K_I$ and $k_{inact}$ and the potency of inactivation, $k_{inact}/K_I$ were calculated using Equation 1 and non-linear least squares regression method using GraphPad Prism 6.01 (San Diego, CA), wherein $k_{inact}$ represents the maximum inactivation rate constant; $K_I$ is the concentration of inhibitor at the half-maximum of inactivation rate constant and [I] is the in vitro inactivator concentration.

$$K_{obs} = \frac{k_{inact} \times [I]}{K_I + [I]} \quad (1)$$

Results are shown in FIG. 10.

(D) Time- and Concentration-Dependent Inactivation of CYP2J2 by Dronedarone, Poyendarone and Additional Deuterated Dronedarone Analogues using the Clinically Relevant Probe Substrate Rivaroxaban as Probe Substrate. The inactivation of human recombinant CYP2J2, by dronedarone, poyendarone, compound 2 and compound 3 was investigated using rivaroxaban as the probe substrate. Incubations were conducted in triplicates in 96-well plates. Primary incubation mixtures comprising various concentrations of inhibitor (0-20 μM) were pre-incubated at 37° C. for 3 min with CYP450 enzymes (20 pmol/mL) and NADPH B in potassium phosphate buffer (100 mM, pH 7.4). To initiate the enzymatic reaction, 5 μL NADPH A was added to the primary incubation. The final primary incubation mixture volume was 100 μL and contained <1% v/v organic solvent. At different pre-incubation time points (3, 8, 15, 22, 30, and 45 min) after the addition of NADPH A, 5 μL aliquots of the primary incubation were transferred to 95 μL of the secondary incubation containing 50 μM rivaroxaban, the NADPH A and B, and potassium phosphate buffer (100 mM, pH 7.4) to yield a 20-fold dilution. The secondary incubation mixtures were incubated at 37° C. for 30 min with CYP2J2, before 80 μL aliquots were removed and quenched with an equal volume of ice-cold ACN containing 4 μM dexamethasone as IS. The samples were then centrifuged at 3220 g at 4° C. for 30 min before transferring the supernatant to a 96-well plate for liquid chromatography-tandem mass spectrometry (LC-MS/MS) analysis. The main rivaroxaban metabolite, morpholinone hydroxylated metabolite, was quantified using LC-MS/MS analysis.

(E) Calculation of Inactivation Kinetic Parameters ($K_I$ and $k_{inact}$)

The mean of triplicate peak area ratios for each concentration and pre-incubation time was normalized to that of 0 μM with the same pre-incubation time. The amount of rivaroxaban metabolite formed during the secondary incubation, a measure of the probe substrate activity remaining, was computed and the natural logarithm of this measure was plotted against inactivation pre-incubation time for each inactivator concentration. For each concentration, the data was then fitted to a linear regression model, through which $k_{obs}$ (apparent inactivation rate constant) was obtained as the negative gradient of the linear regression. A plot of $k_{obs}$ against inactivator concentration ([I]) allowed the fitting of inactivation kinetic parameters ($K_I$ and $k_{inact}$, explained below) to nonlinear least-squares regression based on equation 1 using GraphPad Prism 8:

$$k_{obs} = \frac{k_{inact} \times [I]}{K_I + [I]} \quad (1)$$

In equation 1, $k_{inact}$=maximum inactivation rate constant at infinite inactivator concentration (in $min^{-1}$); $K_I$=concentration of inactivator at the half-maximal rate constant of inactivation (in μM); [1]=in vitro inactivator concentration (in μM). MBI potency ($k_{inact}/K_I$ ratio, μM−1·min−1) against human recombinant CYP2J2 is determined for each compound. The higher the $k_{inact}/K_I$ ratio, the greater the MBI potency.

Results are shown in FIG. 11 and FIG. 12, and summarised in Table 3

In Vitro Expression of Human CYP2J2 and sEH mRNA in HiPSC-CM and In Vitro Inhibition of Human CYP2J2 in hiPSC-CM by Amiodarone, Dronedarone and Poyendarone (A) Reagents. High-performance liquid chromatography (HPLC)-grade ACN and dimethyl sulphoxide (DMSO) was purchased from Tedia Company Inc. (Fairfield, OH). Dronedarone hydrochloride, amiodarone hydrochloride, astemizole and buspirone hydrochloride were purchased from Sigma-Aldrich (St. Louis, MO). Milli-Q® water purification system acquired from EMD Millipore (Billerica, MA). Poyendarone hydrochloride was synthesized in-house according to the synthesis detailed herein. All other reagents were of analytical grade. Stock solutions of dronedarone, poyendarone, astemizole and buspirone were prepared in DMSO stored at −20° C.

(B) Cell Line and Culture. Human foreskin fibroblasts were reprogrammed to form human induced pluripotent stem cells (hiPSC) using viral-free method. hiPSC cell lines were differentiated to cardiomyocytes (hiPSC-CM) as reported previously[1].

(C) Total RNA Extraction and Quantitative Gene Expression. Total RNA was isolated from 30 day old hiPSC-CM using RNeasy Kit (Qiagen GmbH, Hilden, Germany), a kit for RNA isolation. Isolated RNA was quantified using NanoDrop™ 2000 UV-Vis spectrophotometer (Thermo Fischer, Waltham, MA). 1 μg of total RNA was converted to cDNA by Superscript III first-strand synthesis kit (Invitrogen). cDNA template was used for PCR using Quantifast Kit (Qiagen GmbH, Hilden, Germany) with SYBR Green dye as DNA binding agent. PCR was performed using Biorad (Applied Biosciences) thermocycler with the following conditions: 2 min at 55° C., 5 min at 95° C. followed by 40 cycles of 10s at 95° C. and 30s at 60° C. for extension. No template controls were run to check for primer dimers. Relative quantification was carried out using ΔCt method with GAPDH as an endogenous control. The PCR products were mixed with 6× loading dye (Thermo Fischer, Waltham, MA) and loaded on 3% agarose gel prepared in 1×TAE buffer (Vivantis, Subang Jaya, Malaysia) with 1×GelRed™ nucleic acid stain (Biotium, Fremont, CA). GeneRuler Ultra Low Range DNA ladder (Thermo fisher) was used as a molecular weight marker. The resolved cDNA samples were analyzed using Gel Doc™ EZ (Bio rad, Hercules, CA) gel imaging system accompanied by Image Lab™ (Bio Rad, Hercules, CA) image processing software. In human cardiomyocytes, CYP2J2 and sEH are encoded by CYP2J2 and EPHX2 genes. GAPDH was used as an endogenous control. The forward and reverse primer sequences of CYP2J2, EPHX2 and GAPDH are summarized in Table 4.

(D) Inhibition of CYP2J2-mediated Astemizole Metabolism. HiPSC-CM were seeded at a density 100,000 cell/well in a 12-well plate and differentiated for 30 days. After differentiation, hiPSC-CM were co-incubated with dronedarone, amiodarone or poyendarone (2 μM) and astemizole (1 μM) in EB2 media for 24 h at 37° C. in a humidified atmosphere of 5% $CO_2$. The cells were then washed with 1×PBS twice and dislodged using Accutase® cell detachment solution. The cells were then pelleted at 2000 g for 10 min at 4° C. The supernatant was discarded and the pellets were resuspended in 100 μL of ice-cold ACN with 0.1 μM buspirone as an internal standard. The cells were sonicated for 15 min on ice to bring about complete cell lysis. The lysate was centrifuged at 10,000×g for 15 min at 4° C. The supernatant was collected and analyzed using LC/MS/MS.

(E) Measurement of Residual CYP2J2 Enzyme Activity by LC/MS/MS. The LC/MS/MS system consisted of an Agilent 1290 Infinity ultra-high pressure liquid chromatography (UPLC) system (Agilent Technologies Inc., Santa Clara, CA) interfaced with the AB SCIEX QTRAP® 5500 tandem mass spectrometry (MS/MS) system (AB SCIEX, Framingham, MA). The LC/MS/MS system was controlled by Analyst 1.4.2 software (Applied Biosystems) which performed all chromatographic peak integration. The ACQUITY UPLC BEH C18 column, 1.7 μM, 2.1×50 mm (Waters, Milford, MA), was used to achieve chromatographic separation. The temperatures of the column and samples were maintained at 45° C. and 4° C. respectively. The mobile phases were 0.2% acetic acid in 5 mM ammonium acetate (solvent A) and 0.2% acetic acid in ACN (solvent B). They were delivered at a flow rate of 0.6 mL/min. The elution conditions were optimized as follows: linear gradient 30 to 70% B (0-1.60 min), isocratic at 70% B (1.61-1.99 min), and isocratic at 30% B (2.00-2.50 min). MRM transitions of m/z ratios were carried out in the positive ESI mode to detect O-desmethylastemizole and buspirone (internal standard). The compound-dependent MS parameters are summarized in Table 2.

(F) Data Analysis. Comparisons were made between amiodarone, dronedarone and poyendarone using two-way ANOVA followed by Tukey's post-hoc tests. The values were presented as mean±S.D using GraphPad Prism. Statistical significance was confirmed when *p<0.05, p<0.01, *p<0.001, #p<0.0001.

Results are shown in FIG. 13.

Cytotoxicity Measurement of Poyendarone and Dronedarone (A) Reagents. Dronedarone hydrochloride and all-trans retinoic acid (ATRA) were purchased from Sigma-Aldrich (St. Louis, MO). Poyendarone hydrochloride was synthesised in-house. 14,15-EET was purchased from Cayman Chemical (Ann Arbor, MI). Water was obtained using a Milli-Q® water purification system (Millipore, Billerica, MA). All other reagents were of analytical grade.

(B) H9c2 cell culture. H9c2 cell line was purchased from American Tissue Type Collection (ATCC) (Manassas, VA). The cells were cultured in low-glucose DMEM growth media (Cat No: 31600, Thermo Fisher Scientific, Waltham, MA) supplemented with 1.5 g/L sodium bicarbonate, 25 mM HEPES, 10% fetal bovine serum (FBS) (GE Healthcare, Singapore), 100 units/mL penicillin, 100 μg/mL streptomycin and 250 ng/mL amphotericin B in 75-$cm^2$ tissue-culture flasks at 37° C. in a humidified atmosphere of 5% $CO_2$. Cells were fed every 2-3 days and sub-cultured once 70-80% confluency was achieved to prevent the loss of differentiation potential. For differentiation, H9c2 cells were seeded at a density of 100,000 cells/well in 12-well plates. The cells were maintained for 1 day in low-glucose high-serum growth media to allow for cell attachment. Subsequently, cells were differentiated using 1 μM ATRA.

(C) Concurrent cytotoxicity and reduction of intracellular ATP. H9c2 cells were seeded in a white chimney plate and differentiated. The media was changed to DMEM with 10 mM galactose, 2 mM glutamine (6 mM final), 5 mM HEPES, 1 mM sodium pyruvate, 100 U/mL penicillin, 100 μg/mL streptomycin, 0.25 pg/mL amphotericin B, 1% FBS, 1× insulin-transferrin-selenium and 1 μM ATRA for 48 h to overcome the Crabtree effect. Cells were treated with dronedarone or poyendarone (0-30 μM) in serum-free galactose media for 6 h. The cytotoxicity and intracellular ATP content were measured concurrently using Mitochondrial ToxGlo™ kit (Promega, Madison, WI), an assay for mitochondrial dysfunction, using manufacturer's protocol. Mitochondrial ToxGlo™, an assay for mitochondrial dysfunction, measures the cell viability using fluorogenic peptide bis-alanine-alanine-phenylalanine-R110 (bis-AAF-R110). Bis-AAF-R110 is a selective peptide that measures protease activity in dead cells since it is impermeable to live cells. Here, the fluorescence derived from metabolized bis-AAF-R110 was measured at different concentrations of the test compounds and compared to control. As the concentration of cytotoxic compound increases, the number of dead cells increases, leading to a higher fluorescence signal. ATP is measured by adding the ATP Detection Reagent, resulting in cell lysis and generation of a luminescent signal proportional to the amount of ATP present. Differentiated H9c2 cells were pre-treated with 14,15-EET at varying concentrations (0-1 μM) for 2 h in serum-free galactose media. The media was aspirated and the cells were treated with dronedarone, and the cytotoxicity and intracellular ATP were measured as described.

(D) Measurement of mitochondrial membrane potential ($\Delta\psi_m$). Dissipation of $\Delta\psi_m$ by each test compound was measured using mitochondrial permeable dye, tetramethylrhodamine methyl ester perchlorate (TMRM) (Thermo Fisher Scientific, Waltham, MA). H9c2 cells were seeded at a density of 20,000 cells per well in a 96 well plate. The cells were treated with either dronedarone for 1 h in serum-free low-glucose medium. The media was discarded and the cells washed with 1×PBS twice. TMRM dye (200 nM) was dissolved in serum free media and the plate was incubated for 30 min at 37° C. The media was aspirated, the cells were washed with PBS and fluorescence was measured at 557 nm excitation and 570 nm emission wavelengths. TMRM concentration and cell density were optimized. Differentiated H9c2 cells were pre-treated with 14,15-EET at varying concentrations (0-1 μM) for 2 h. The media was aspirated and then the cells were treated with dronedarone and the dissipation of $\Delta\psi_m$ by AADs was measured as described.

Results are shown in FIG. 14.

Measurement of Extracellular Field Potential Durations (FPD) of HiPSC-CM Induced by Amiodarone, Dronedarone and Poyendarone (A) Electrophysiological Measurements. Electrophysiological perturbations of hiPSC-CM were measured using multi electrode array (MEA) recording system (Multichannel Systems, Reutlingen, Germany). HiPSC-CM were treated with amiodarone, dronedarone or amiodarone (0-10 μM) dosed in 2 mL media and extracellular field potentials durations (FPD) were measured as described previously[2]. FPD measurements were normalized (corrected FPD [cFPD]) to the beating rate of the contracting areas with the Bazzet correction formula: cFPD=FPD/√(RR interval) as described previously[3]. One-phase decay algorithm was used to plot corrected FPD curves.

Results are shown in FIG. 15.

(B) Cell culture and transfection (Nav1.5 current). HEK293FT cells were cultured in DMEM medium supplemented with 10% fetal bovine serum and 1% penicillin and streptomycin and maintained in 5% $CO_2$ incubator at 37° C. For transfection, cells will be seeded on the petri dishes containing cover slips and grown overnight. Subsequently, 3.0 pg of WT or mutant hNav1.5 channels plasmid and 1.5 pg of 31 plasmid were co-transfected into the cells by Lipofectamine™ 2000 (Invitrogen) transfection reagent. The transfected cells were grown for 24 h in 5% $CO_2$ incubator at 37° C. before patch clamp analysis, split and seeded on poly-D coated cover slip 24 h prior to patch clamp analysis.

(C) Whole-cell patch-clamp recordings and data analysis. To record Nav1.5 current, the internal solution (pipette solution) contained (in mM) 130 CsF, 5 NaCl, 5 EGTA, 10 HEPES, 2 $MgCl_2$, 2 TEA-Cl pH 7.2 (adjusted with CsOH). The external solution contained (in mM): 135 NaCl, 4.2 CsCl, 1.2 $MgCl_2$, 1.8 $CaCl_2$), 10 HEPES and glucose, adjusted to pH 7.4 with NaOH. Whole cell currents were obtained under voltage clamp with an Axopatch200B or Multiclamp 200B amplifier (Molecular Device), low-pass filtered at 5 to 6 kHz and the series resistance was typically <5 MΩ after >70% compensation. The P/4 protocol was used to subtract online the leak and capacitive transients. Dose response curve was fitted with log(inhibitor) vs response variable slope equation Y=Bottom+(Top−Bottom)/(1+10^((Log IC50−X)*HillSlope))

Results are shown in FIG. 16, FIG. 17 and FIG. 18.

(D) Cell culture and transfection (Cav1.2 current). HEK293FT cells were cultured in DMEM medium supplemented with 10% fetal bovine serum and 1% penicillin and streptomycin and maintained in 5% $CO_2$ incubator at 37° C. For transfection, cells will be seeded on the petri dishes containing cover slips and grown overnight. Subsequently, 1.7 pg of human Cav1.2_1a8a cardiac variant and 1.25 pg of human β2 and α2δ1 subunit by Lipofectamine™ 2000 (Invitrogen) transfection reagent. The transfected cells were grown for 24 h in 5% $CO_2$ incubator at 37° C. before patch clamp analysis, split and seeded on poly-D coated cover slip 24 h prior to patch clamp analysis.

(E) Whole-cell patch-clamp recordings and data analysis. To record Cav1.2 current the internal solution (patch-pipette solution) contained the following (in mM): 138 Cs-$MeSO_3$, 5 CsCl, 5.0 EGTA, 10 HEPES, 1 $MgCl_2$, 2 mg/ml Mg-ATP, pH 7.3 (adjusted with CsOH), 290 mOsm with glucose. The external solution contained the following (in mM): 10 HEPES, 140 tetraethylammonium methanesulfonate, 5 $CaCl_2$) (pH adjusted to 7.4 with CsOH and osmolality to 290-310 with glucose). Pipettes of resistance 1.5-2 MΩ were used. Whole cell currents were obtained under voltage clamp with an Axopatch200B or Multiclamp 200B amplifier (Molecular Device), low-pass filtered at 1 kHz and the series resistance was typically <5 MΩ after >70% compensation. The P/4 protocol was used to subtract online the leak and capacitive transients. Dose response curve was fitted with log(inhibitor) vs response variable slope equation Y=Bottom+(Top−Bottom)/(1+10^((Log IC50−X)*HillSlope))

Results are shown in FIG. 19, FIG. 20 and FIG. 21.

(F) Cell culture and transfection ($K_v$11.1 current). HEK293FT cells were cultured in DMEM medium supplemented with 10% fetal bovine serum and 1% penicillin and streptomycin and maintained in 5% $CO_2$ incubator at 37° C. For transfection, cells will be seeded on the petri dishes and grown overnight. Subsequently, 2 μg of WT or mutant $K_v$11.1 channels plasmid and 1 μg of KCNE1 plasmid were co-transfected into the cells by Lipofectamine™ 2000 transfection reagent. The transfected cells were incubated for 24 h in 5% $CO_2$ incubator at 37° C. 48 h post transfection, the cell were split and seeded on poly-D lysine cover slip one day before recording.

(G) Whole-cell patch-clamp recordings and data analysis. To record $K_v$11.1 current, the internal solution (pipette solution) contained (in mM) 130 K-gluconate, 10 KCl, 5 EGTA, 10 HEPES, 1 $MgCl_2$, 0.5 $Na_3GTP$, 4 Mg-ATP, Na-phoshocreatine pH 7.4 (adjusted with KOH). The external solution contained (in mM): 125 NaCl, 2.5 KCl, 25 Na-gluconate, 1.0 $MgCl_2$, 1.8 $CaCl_2$, 10 HEPES and 11.1 glucose, adjusted to pH 7.4 with NaOH. Whole cell currents were obtained under voltage clamp with an Axopatch200B or multiclamp 200B amplifier (Molecular Device), low-pass filtered at 1 kHz and the series resistance was typically <5 MΩ after >70% compensation. The P/4 protocol was used to subtract online the leak and capacitive transients The $K_v$11.1 current was evoked from holding potential of −80 mV to 2.5 s pulses of 20 mV. The tail currents were subsequently recorded upon returning the voltage to −60 mV. Dose response curve was fitted with log(inhibitor) vs response variable slope equation Y=Bottom+(Top−Bottom)/(1+10^((Log IC50−X)*HillSlope))

Results are shown in FIG. 22, FIG. 23 and FIG. 24.

In Vitro Measurement of Beat-to-Beat Variability (BBV) in HiPSC-CM Induced by Amiodarone, Dronedarone and Poyendarone (A) Measurement of BBV. The BBV calculations were done using Kubios HRV2.2 (Department of Applied Physics, University of Eastern Finland, Kuopio, Finland)[4]. BBV is visualised as scatterplots known as Poincaré plots. In these plots, each time interval between two successive beats [inter-beat interval ($RR_n$)] is plotted against the subsequent interval ($RR_{n+1}$). Poincaré plot descriptors SD1 and SD2 define the extent of variability. SD1 represents a measure for short-term variability, whereas SD2 describes long-term variability[5].

Results are shown in FIG. 25.

In Vivo Pharmacokinetic Studies of Dronedarone and Poyendarone in Dogs (A) Reagents. High-performance liquid chromatography (HPLC)-grade acetonitrile (ACN) was purchased from Tedia Company Inc. (Fairfield, OH). Dronedarone hydrochloride was purchased from Sigma-Aldrich (St. Louis, MO). N-desethylamiodarone (NDEA) hydrochloride was purchased from Cayman Chemical (Ann Arbor, MI). Poyendarone hydrochloride was synthesized in-house according to the synthesis detailed herein. Water was obtained using a Milli-Q® water purification system (Millipore, Billerica, MA). Dimethyl Sulfoxide (DMSO) was purchased from VWR Life science (Pennsylvania, USA).

(B) Plasma samples. For each compound (dronedarone or poyendarone), plasma samples were obtained from 4 male dogs weighing approximately 10 kg, from Kitayama Labes Co., Ltd (Nagano, Japan). All experiments were approved by the Animal Research Committee for Animal Experimentation of Toho University (No. 12-52-151) and performed in accordance with the Guidelines for the Care and Use of Laboratory Animals of Toho University. Plasma samples were obtained at 5, 10, 15, 20, 30, 45 and 60 min for intravenous (IV) bolus doses 3.0 mg/kg of dronedarone or poyendarone. Plasma samples were stored at −80° C. and thawed in ice before use.

(C) Sample preparation. Ice cold NDEA internal standard (IS) solution was used for protein precipitation at a plasma: IS ratio of 1:3. The mixture was vortex-mixed for 1 min, followed by centrifugation at 14,000 g at 4° C. for 15 min. The supernatant was then transferred into a vial for LC/MS/MS analysis.

(D) Instruments. The LC/MS/MS system consisted of Infinity ultra-high-pressure liquid chromatography (UHPLC) system (Agilent Technologies Inc., Santa Clara, CA) with the AB SCIEX QTRAP® 5500 tandem mass spectrometry (MS/MS) system (AB SCIEX, Framingham, MA). MultiQuant software version 1.4.0.18067 (Applied Biosystems) was used to perform all chromatographic peak integration.

(E) LC/MS/MS condition. Chromatographic separation was performed using ACQUITY UPLC BEH C18 column, 1.7 μm, 2.1×50 mm (Waters, Milford, MA), with a gradient elution programme. The mobile phases were 0.2% acetic acid in 5 mM ammonium acetate in water (A) and 0.2% acetic acid in ACN (B). The elution conditions were linear gradient 30-95% B (0-1.60 min), isocratic at 95% B (1.61-1.99 min), and isocratic at 30% B (2.00-2.50 min) [21]. Multiple reaction monitoring (MRM) transitions were optimized for NDEA (internal standard, IS), dronedarone and poyendarone. Other MS conditions are listed in Table 5.

(F) Deriving pharmacokinetic parameters using non-compartmental analysis (NCA). Individual pharmacokinetic parameters were estimated using NCA for IV bolus data (Model 201), using WinNonlin® (Pharsight, USA) software. Area under curve from time 0 min to the time of last observation (AUC) and AUC extrapolated to infinity (AUCinf) were calculated using log trapezoidal rule. Data points included in the calculation of Lambda Z (Az) were first determined by WinNonlin® software, and then visually assessed and modified accordingly. Other parameters calculated include apparent total plasma clearance (CL), apparent volume of distribution based on terminal phase ($V_z$), apparent elimination half-life ($T_{1/2}$), apparent volume at steady state ($V_{ss}$), mean residence time (MRT) and MRT extrapolated to infinity (MRTinf). $V_{ss}$ is the apparent volume of distribution when plasma concentration across all compartments has achieved steady state condition. Each drug was then fitted into compartmental models using WinNonlin® software to visualize the individual disposition models.

(G) Statistical analysis. Pharmacokinetic parameters were log-transformed, and distribution of the log-transformed data was assumed to be normally distributed. For one-way ANOVA, the null hypothesis was that there is no difference in each of the mean pharmacokinetic parameter estimates (CL and $V_z$) between dronedarone and poyendarone. All statistical tests were conducted using IBM SPSS Statistics for Windows, Version 25.0 (IBM Corp, Armonk, NY).

Results are shown in FIG. 26.

Comparison of Poyendarone and Dronedarone In Vivo Pharmocokinetics (A) Chemicals. High-performance liquid chromatography-grade acetonitrile (ACN) was purchased from Tedia Company Inc. (Fairfield, OH). Dronedarone hydrochloride and dexamethasone were acquired from Sigma-Aldrich (St. Louis, MO). Poyendarone hydrochloride was synthesized in-house. Pooled human liver microsomes (HLM), recombinant human CYP450 Supersomes® and a reduced nicotinamide adenine dinucleotide phosphate (NADPH) regenerating system consisting of NADPH A ($NADP^+$ and glucose-6-phosphate) and B (glucose-6-phosphate dehydrogenase) were obtained from BD Gentest (Woburn, MA). Water was obtained using a Milli-Q® water purification system (Millipore, Billerica, MA). All other reagents were of analytical grade.

(B) Metabolic stability study. The metabolic stability experiments were performed to derive intrinsic clearance ($CL_{int}$) values via the substrate depletion method. 1 μM dronedarone or poyendarone were pre-incubated with CYP3A4 (10 pmol/mL), CYP3A5 (10 pmol/mL) or HLM (0.5 mg/mL) in potassium phosphate buffer (100 mM, pH 7.4) and NADPH B at 37° C. for 5 min. NADPH A was subsequently added to initiate the reaction. The final incubation mixture had a total volume of 100 μL and contained <1% v/v organic solvent. The reaction mixtures were incubated at 37° C. with gentle agitation. At the respective time points (0-60 min), 80 μL of the reaction mixture was quenched using an equal volume of ice-cold ACN with 1 μM tamoxifen as internal standard (IS). The samples were then centrifuged at 3220 g at 4° C. for 30 min before transferring the supernatant to a 96-well plate for liquid chromatography-tandem mass spectrometry (LC-MS/MS) analysis.

Results are shown in FIG. 27.

(C) Calculation of $CL_{int}$ values. The mean of triplicate peak area ratios for each compound was normalized to that of the same compound at the 0 min time point to obtain the percentage of substrate remaining at each time point. This was plotted against incubation time for each compound and the data was then fitted to a one-phase decay model using GraphPad Prism software (version 8.02; GraphPad Inc., San Diego, CA) to obtain an estimation for the elimination rate constant (k). $CL_{int}$ was then calculated based on equation 3:

$$CL_{int} = k \times \frac{V}{P} \tag{3}$$

In equation 3, k=elimination rate constant ($min^{-1}$); V=volume of incubation mixture (mL); P=amount of protein in mixture (mg).

Results are shown in Table 6.

(D) Time- and concentration-dependent inactivation of CYP3A4 and CYP3A5. The inactivation of human recombinant CYP3A4 and CYP3A5 by dronedarone and poyendarone was investigated using rivaroxaban as the probe substrate. Incubations were conducted in triplicates in 96-well plates. Primary incubation mixtures comprising various concentrations of inhibitor (0-20 μM) were pre-incubated at 37° C. for 3 min with CYP3A4 or CYP3A5 (20 pmol/mL) and NADPH B in potassium phosphate buffer (100 mM, pH 7.4). To initiate the enzymatic reaction, 5 μL NADPH A was added to the primary incubation. The final primary incubation mixture volume was 100 μL and contained <1% v/v organic solvent. At different pre-incubation time points (3, 8, 15, 22, 30, and 45 min) after the addition of NADPH A, 5 μL aliquots of the primary incubation were transferred to 95 μL of the secondary incubation containing 50 μM rivaroxaban, the NADPH A and B, and potassium phosphate buffer (100 mM, pH 7.4) to yield a 20-fold dilution. The secondary incubation mixtures were incubated at 37° C. for 2 h with CYP3A4 or CYP3A5 before 80 μL aliquots were removed and quenched with an equal volume of ice-cold ACN containing 4 μM dexamethasone as IS. The samples were then centrifuged at 3220 g at 4° C. for 30 min before transferring the supernatant to a 96-well plate for liquid chromatography-tandem mass spectrometry (LC-MS/MS) analysis. The main rivaroxaban metabolite, morpholinone hydroxylated metabolite, was quantified using LC-MS/MS analysis.

(E) Calculation of inactivation kinetic parameters ($K_I$ and $k_{inact}$). The mean of triplicate peak area ratios for each inhibitor concentration and pre-incubation time was normalized to that of 0 μM inhibitor with the same pre-incubation time. The amount of rivaroxaban metabolite formed during the secondary incubation, a measure of the probe substrate activity remaining, was computed and the natural logarithm of this measure was plotted against inactivation pre-incubation time for each inactivator concentration. For each concentration, the data was then fitted to a linear regression model, through which $k_{obs}$ (apparent inactivation rate constant) was obtained as the negative gradient of the linear regression. A plot of $k_{obs}$ against inactivator concentration ([I]) allowed the fitting of inactivation kinetic parameters ($K_I$ and $k_{inact}$, explained below) to nonlinear least-squares regression based on equation 4 using GraphPad Prism 8:

$$k_{obs} = \frac{k_{inact} \times [I]}{K_I + [I]} \quad (4)$$

In equation 4, $k_{inact}$=maximum potential inactivation rate constant at infinite inactivator concentration ($min^{-1}$); $K_I$=half-maximal rate constant of inactivation (μM); [I]=in vitro inactivator concentration (μM).

Results are shown in Table 6.

(F) Development of PBPK models. Simcyp™ simulator (version 19.0.96.0; Sheffield, UK) was used to construct PBPK models of dronedarone and poyendarone. Key drug-dependent parameters implemented in Simcyp™ simulator as sourced from literature are listed in Table 7 below. The construction of PBPK models of dronedarone was undertaken using a middle-out approach combining data from in vitro experiments and observed clinical parameters.

Results are shown in FIG. 28.

(G) Verification of PBPK models. Using the Simcyp™ simulator, the $CL_{int}$ and $f_{u,mic}$ values were scaled via 2 scaling factors (milligrams of protein per gram of liver, MPPGL; as well as mean liver weight) to obtain the unbound hepatic intrinsic clearance $CL_{u,int,H}$. The well-stirred model of hepatic clearance was applied to calculate hepatic blood clearance, $CL_{b,H}$, which was subsequently converted to plasma clearance via the blood-to-plasma concentration ratio (B/P) as well as fraction metabolized ($f_m$).

The virtual population adopted was Sim-Healthy Volunteers, except the maximum age was changed to 67 to match that of selective clinical trials used to validate simulations. A simulated plasma concentration-time profile for each dosing regimen (e.g. intravenous, single oral dosing, multiple oral dosing) was generated and compared against clinical data obtained via digitization of published average plasma-concentration time data using WebPlotDigitizer (version 4.2). The acceptability of the predicted PK parameters were, where possible, compared against ranges of acceptability generated using the method outlined by Abduljalil et al[9]. Where success criteria could not be computed, the standard 0.5- to 2-fold ratio was used.

Results are shown in FIG. 29.

Measurement of c Log P, Aqueous Solubility, Effective Permeability and In Vitro Metabolic Half-Life of Dronedarone and Poyendarone (A) Assays. The calculated Log P (c Log P) of dronedarone and poyendarone was calculated computationally using ChemSketch. The aqueous solubility of each compound was measured in universal buffer (pH 7.4) using $Multiscreen_{HTS}$ PCF Filter Plates. The effective permeability of each compound was measured using the parallel artificial membrane permeability assay (PAMPA). Finally, the in-vitro metabolic half-lives ($T_{1/2}$) of 1 μM dronedarone and 1 μM poyendarone were measured using recombinant human CYP2J2.

Results are shown in Table 8.

Comparison of the Effects of Antiarrhythmic Drugs on the Atrial (AERP) and Ventricular (VERP) Refractory Periods and Comparison of the Effects of Antiarrhythmic Drugs on the Early (J-Tpeakc) and Late (Tpeak-Tend) Repolarization Periods (A) Materials and methods. For each drug (dronedarone, amiodarone and poyendarone), the experiments were performed in female dogs weighing approximately 10 kg (n=4). Animals were obtained through Kitayama Labes Co., Ltd. (Nagano, Japan). All experiments were approved by the Toho University Animal Care and User Committee (No. 18-51-395) and performed according to the Guideline for the Care and Use of Laboratory Animals of Toho University.

(B) General anesthesia and surgical preparation. The dogs were initially anesthetized with thiopental sodium (30 mg/kg, i.v.). After intubation with a cuffed endotracheal tube, anesthesia was maintained by inhalation of halothane (1% v/v) vaporized in oxygen with a volume-limited ventilator (SN-480-3; Shinano Manufacturing Co., Ltd., Tokyo, Japan). Tidal volume and respiratory rate were set at 20 mL/kg and 15 breaths/min, respectively. Six clinically available catheter-sheath sets (FAST-CATH™ 406119; St. Jude Medical Daig Division, Inc., MN, USA) were used; two were inserted into the right and left femoral arteries toward abdominal aorta, respectively, two were done into the right femoral vein, and the other two were done into the left femoral vein toward inferior vena cava. To prevent blood clotting, heparin calcium (100 IU/kg) was intravenously administered through a flush line of the catheter sheath placed at the right femoral vein.

(C) Cardiohemodynamic variables. A pig-tail catheter was placed at the left ventricle through the right femoral artery to measure the left ventricular pressure, whereas aortic pressure was measured at a space between inside of the catheter sheath and outside of the pig-tail catheter through a flush line. Left ventricular pressure at a time point of peak of R wave on ECG was defined as left ventricular end-diastolic pressure. The maximum upstroke velocity of the left ventricular pressure ($LVdP/dt_{max}$) and the left ventricular end-diastolic pressure were obtained during sinus rhythm to estimate the contractility and the preload to the left ventricle, respectively. A thermodilution catheter (TC-504NH; Nihon Kohden, Co., Tokyo, Japan) was positioned at the right side of the heart through the right femoral vein.

The cardiac output was measured by using a standard thermodilution method with a cardiac output computer (MFC-1100, Nihon Kohden, Co.). The total peripheral vascular resistance was calculated with the basic equation: total peripheral vascular resistance=mean blood pressure/cardiac output.

(D) Electrophysiological variables. The lead II electrocardiogram was obtained from the limb electrodes. The P-wave duration, PR interval, QRS width and QT interval were measured, and QT interval was corrected with Van de Water's formula: QTc=QT−0.087×(RR−1,000) with RR given in ms. The J-$T_{peak}$ and $T_{peak}$-$T_{end}$ were measured as follows. When the end of T-wave was obscure, we used the monophasic action potential (MAP) signal as a guide to estimate the end. The J-$T_{peak}$ was corrected for the heart rate with a coefficient as previously described (J-$T_{peakC}$=J-$T_{peak}$/$RR^{0.58}$ with RR given in seconds). Correction was not performed on the $T_{peak}$-$T_{end}$, since previous QT/QTc studies have shown that the $T_{peak}$-$T_{end}$ exhibited minimal heart rate dependency at the resting heart rate.

A standard 6-French, quad-polar electrodes catheter (Cordis-Webster Inc., Baldwin Park, CA, USA) was positioned at the non-coronary cusp of the aortic valve through the left femoral artery to obtain the His bundle electrogram. Another 6-French, quad-polar electrode catheter (Cordis-Webster Inc.) was positioned at the sinus nodal areas of the right atrium through the right femoral vein to electrically pace and to record the local electrogram. A bi-directional steerable MAP recording/pacing combination catheter (1675P; EP Technologies, Inc., CA, USA) was positioned at the endocardium of the interventricular septum in the right ventricle through the left femoral vein to obtain MAP signals. The signals were amplified with a DC preamplifier (model 300; EP Technologies, Inc.). The duration of the MAP signals was measured as an interval, along a horizontal line corresponding to the diastolic baseline, from the MAP upstroke to the desired repolarization level. The interval (ms) at 90% repolarization was defined as $MAP_{90}$.

The heart was electrically driven with a cardiac stimulator (SEC-3102; Nihon Kohden Co., Ltd.) via the pacing electrodes of the combination catheter placed in the right ventricle or the electrodes of the catheter placed at the right atrium. The stimulation pulses were rectangular in shape, 1-2 V (about twice the threshold voltage) and 1 ms duration. The $MAP_{90}$ of the ventricle was measured during sinus rhythm ($MAP_{90(sinus)}$) and at a pacing cycle length of 400 ms ($MAP_{90(CL400)}$) and 300 ms ($MAP_{90(CL300)}$). The atrial effective refractory period (AERP) and ventricular effective refractory period (VERP) were assessed with the programmed electrical stimulation. The pacing protocol consisted of 5 beats of basal stimuli in a cycle length of 400 ms followed by an extra stimulus of various coupling intervals. Starting in the late diastole, the coupling interval was shortened in 5-ms decrements until the additional stimulus could no longer elicit a response. The AERP and VERP were defined as the shortest coupling interval that could produce a response. The duration of the terminal repolarization period of the ventricle, reflecting phase-3 repolarization time of the action potential, was calculated by the difference between the $MAP_{90(CL400)}$ and VERP (terminal repolarization period=$MAP_{90(CL400)}$−VERP) at the same site to estimate the extent of electrical vulnerability of the ventricular muscle.

(E) Experimental protocol. The aortic pressure, left ventricular pressure, electrocardiogram, right atrial electrogram, His bundle electrogram and MAP signals were monitored with a polygraph system (RM-6000, Nihon Kohden, Co.) and analyzed by using a real-time fully automatic data analysis system (Win VAS 3 for Windows ver. 1.1R24v; Physio-Tech, Tokyo, Japan). Three recordings of consecutive complexes were used to calculate the mean for the electrocardiogram indices, MAP duration as well as atrio-His (AH) and His-ventricular (HV) intervals. The cardiovascular variables were assessed in the following order. The electrocardiogram, atrial and His bundle electrograms, aortic pressure, left ventricular pressure and MAP signals were recorded under sinus rhythm. Then, the cardiac output was measured 3 times. Next, MAP signals were recorded during the ventricular pacing at a cycle length of 400 and 300 ms. Finally, VERP and AERP were measured. All parameters described above were usually obtained within 2 min at each time point.

After the basal assessment, poyendarone hydrochloride in a low dose of 0.3 mg/kg was intravenously infused through the catheter sheath placed at the left femoral vein over 30 s, and each variable was assessed at 5, 10, 15, 20 and 30 min after the start of administration (n=4). Then, poyendarone hydrochloride in a high dose of 3 mg/kg was infused in the same manner, and each variable was observed at 5, 10, 15, 20, 30, 45 and 60 min after the start of administration. We selected the current doses of poyendarone hydrochloride to directly compare its electropharmacological effects to those of dronedarone hydrochloride[6].

Results are shown in Tables 9 and 10.

Atrial Electropharmacological Properties of Poyendarone as an Anti-Atrial Fibrillatory Drug in Paroxysmal AF Canine Model (A) Animals. Experiments were performed using female beagle dogs weighing approximately 10 kg (n=4). Animals were obtained through Kitayama Labes Co., Ltd. (Nagano, Japan). All experiments were approved by the Toho University Animal Care and User Committee (No. 19-52-395) and performed according to the Guideline for the Care and Use of Laboratory Animals of Toho University.

(B) Production of the chronic atrioventricular block dog. The catheter ablation technique of atrioventricular node was employed as previously described[11,14]. The dogs were anesthetized with pentobarbital sodium (30 mg/kg, i.v.). After intubation with a cuffed endotracheal tube, the respiration was controlled with room air using a volume-limited ventilator (SN-480-3; Shinano Manufacturing Co., Ltd., Tokyo, Japan). Tidal volume and respiratory rate were set at 20 mL/kg and 15 breaths/min, respectively. Heparin calcium (100 IU/kg, i.v.) was administered to prevent blood clotting. The surface lead II electrocardiogram was continuously monitored. A quad-polar electrodes catheter with a large tip of 4 mm (D7-DL-252; Cordis-Webster Inc., CA, USA) was inserted through the catheter sheath (FAST-CATH™ 406119; St. Jude Medical Daig Division, Inc., Minnetonka, MN, USA) placed at the right femoral vein and positioned across the tricuspid valve under the guide of bipolar electrogram from the distal electrode pair. The optimal site for the atrioventricular node ablation; namely, the compact atrioventricular node, was determined on the basis of the intra-cardiac electrogram, of which a very small His deflection was recorded and atrial/ventricular voltage ratio was >2. The power source for the atrioventricular nodal ablation was obtained from an electrosurgical generator (MS-1500; Senko Medical Instrument Manufacturing Co., Ltd., Tokyo, Japan), which delivers continuous unmodulated radiofrequency energy at a frequency of 500 kHz. After determining the proper location, the radiofrequency energy of 20 W was delivered for 10 s from the tip electrode to an indifferent patch electrode positioned on the animal's back, which was continued then for 30 s if junctional ectopic complexes were induced. The endpoint of this procedure was the development of the complete atrioventricular block with an onset of stable idioventricular escaped rhythm. All surgical procedures described above were performed under the sterile condition. Proper care was taken for the animals until the electropharmacological and anti-atrial fibrillatory effects of poyendarone were studied[11,14].

(C) Surgical preparation of the paroxysmal atrial fibrillation model. The paroxysmal atrial fibrillation model was prepared as previously reported[12,13]. More than 3 months after the induction of atrioventricular block, the dogs (n=4) were anesthetized with pentobarbital sodium (30 mg/kg, i.v.). After intubation with a cuffed endotracheal tube, the dogs were artificially ventilated with 0.5-1.5% isoflurane in oxygen using a volume-limited ventilator (SN-480-3; Shinano Manufacturing Co., Ltd.). Tidal volume and respiratory rate were set at 20 mL/kg and 15 breaths/min, respectively. The surface lead II electrocardiogram was obtained from the limb electrodes. Four clinically available catheter-sheath (FAST-CATH™; St. Jude Medical Daig Division, Inc.) were used; two were inserted into the right femoral vein, and the other two were done into the left femoral vein toward inferior vena cava. An indwelling needle (Surflo® 18G; Terumo Corporation, Tokyo, Japan) was placed at the right femoral artery, through which the arterial blood pressure was measured.

Three sets of standard 6-French quad-polar electrodes catheter (Cordis-Webster Inc.) were used. First one was positioned at the high right atrium through the right femoral vein to electrically pace the sinus nodal area and to simultaneously obtain the right atrial electrogram. Second one was positioned in the esophagus via os to record to the left atrial electrogram. Third one was positioned at the inter-atrial septum of the right atrium through the left femoral vein to electrically induce paroxysmal atrial fibrillation as described below. The optimal sites of each catheter were determined by the temporal relationship between the bipolar atrial electrograms from the distal electrodes pair and P wave of the electrocardiogram. A standard 4-French quad-polar electrodes catheter (401993; St. Jude Medical Daig Division, Inc.) was positioned at the endocardium of the right ventricle through the right femoral vein to electrically drive the right ventricle.

(D) Measurement of electrophysiological variables. The heart was electrically driven with the cardiac stimulator (SEC-3102; Nihon Kohden Corporation) through the pacing electrodes of the catheters placed at the sinus nodal area or at the right ventricle. The stimulation pulses were set rectangular in shape, consisting of 2-2.5 V amplitude (about twice the threshold voltage) and 1 ms duration. The inter-atrial conduction time (IACT) was defined as the difference in the temporal locations between the right and left atrial electrograms, which was measured at a pacing cycle length of 400 ms ($IACT_{(CL400)}$), 300 ms ($IACT_{(CL300)}$) and 200 ms ($IACT_{(CL200)}$). The atrial (AERP) and ventricular effective refractory period (VERP) were assessed with programed electrical stimulation on the sinus nodal area and the right ventricle, respectively. The pacing protocol consisted of 5 beats of basal stimuli in cycle lengths of 400 ms ($AERP_{(CL400)}$), 300 ms ($AERP_{(CL300)}$) and 200 ms ($AERP_{(CL200)}$) for AERP, and 400 ms ($VERP_{(CL400)}$) for VERP followed by an extra stimulus of various coupling intervals. The coupling interval was shortened in 5 ms decrements until the additional stimulus could no longer elicit a response. AERP and VERP were defined as the shortest coupling interval that can evoke stimulus-response.

(E) Induction of paroxysmal atrial fibrillation. The inter-atrial septum was electrically paced at a cycle length of 60 ms (1,000 bpm) for 10 s (=burst pacing) through the distal electrodes pair of the catheter using a stimulator (SEN-7203; Nihon Kohden Corporation) with the isolation unit (SS-201J; Nihon Kohden Corporation) [2,3]. The stimulation pulses for inducing atrial fibrillation were set rectangular in shape, consisting of 60 V amplitude and 10 ms duration. Atrial fibrillation was defined as a period of rapid irregular atrial rhythm resulting in an irregular baseline on the electrocardiogram. The duration of atrial fibrillation was measured from its induction to termination in the right atrial electrogram, whereas the cycle length of atrial fibrillation was determined using the left atrial electrogram.

(F) Experimental protocol. The right and left atrial electrograms, electrocardiogram and arterial blood pressure were monitored with a polygraph system (RM-6000; Nihon Kohden Corporation), and analysed with real-time fully automatic data analysis system (WinVAS3 ver. 1.1R24; Physio-Tech Co., Ltd., Tokyo, Japan). Each measurement of the ACT variables adopted the mean of three recordings of consecutive complex. The electropharmacological variables were assessed in the following order. First, the right and left atrial electrograms, electrocardiogram and arterial blood pressure were recorded under the spontaneous sinus rhythm. Second, the sinus nodal area was electrically paced at cycle lengths of 400, 300 and 200 ms to measure the ACT. Third, the AERP was assessed at basic pacing cycle lengths of 400, 300 and 200 ms, and the VERP was measured at a basic pacing cycle length of 400 ms. Fourth, paroxysmal atrial fibrillation was induced by the burst pacing protocol, which was repeated 10 times at each time point. When the atrial fibrillation converted to atrial flutter or was maintained for >30 s, it was terminated by the rapid atrial pacing and its duration was regarded as 30 s.

After the basal assessment, poyendarone hydrochloride in a low dose of 0.3 mg/kg was intravenously infused through the catheter sheath placed at the left femoral vein over 30 s, and each variable was assessed at 10, 20 and 30 min after the start of administration (n=4). Then, poyendarone hydrochloride in a high dose of 3 mg/kg was infused in the same manner, and each variable was observed at 10, 20, 30, 45 and 60 min after the start of administration.

(G) Poyendarone hydrochloride and drugs. Poyendarone hydrochloride was dissolved with 100% ethanol in a concentration of 20 mg/mL to prepare 0.3 mg/15 μL/kg and 3 mg/150 μL/kg injections. The other drugs used were pentobarbital sodium (Tokyo Chemical Industry Co., Ltd., Tokyo, Japan), isoflurane (ISOFLURANE Inhalation Solution, Pfizer Japan Inc., Tokyo, Japan) and heparin calcium (Caprocin®, Sawai Pharmaceutical Co., Ltd., Osaka, Japan).

(H) Statistical analysis. Data are presented as mean±S.E.M. Differences within a parameter were evaluated with one-way, repeated-measures analysis of variance (ANOVA) followed by Contrasts as a post hoc-test for mean values comparison. A p value $<0.05$ was considered to be significant.

Results are shown in FIG. 30, FIG. 31, FIG. 32 and FIG. 33.

Results

Amiodarone (FIG. 1A) is associated with severe lung and thyroid toxicities. This is primarily due to the presence of iodine atoms on the molecule, lipophilicity and extensive tissue accumulation. Dronedarone (FIG. 1B), is a non-iodinated analogue of amiodarone that has lower tissue accumulation due to the addition of a methanesulphonamide group and so is devoid of the afore systemic toxicities.

However it worsens heart failure and increases mortality in patients with permanent AF and NYHA Class III and IV heart failure. Due to these fatal side effects, USFDA has issued a black-box warning for its cardiac adverse effects.

Unfortunately, the clinical development of another amiodarone analogue, celivarone, has been discontinued due to poor efficacy.

Arachidonic acid (AA) is an endogenous w-6 polyunsaturated fatty acid and serves as a precursor for a number of biologically important lipids such as prostaglandins and thromboxanes. AA is metabolized primarily by cyclooxygenases, lipoxygenases and CYP450 enzymes. Extrahepatic CYP2J2 is an epoxygenase predominantly expressed in the human heart and metabolizes AA to four regioisomeric, cardioprotective epoxyeicosatrienoic acids (EETs) (FIG. 2). EETs are instrumental in maintaining cardiac homeostasis due to their vasodilatory, anti-inflammatory, anti-apoptotic and ion channel regulatory activities. EETs undergo further metabolism to less potent dihydroxyeicosatrienoic acids (DHETs) by soluble epoxide hydrolase (sEH) (FIG. 2). Alterations in cardiac CYP2J2 and subsequent perturbations of AA metabolism are responsible for the initiation, sustenance and worsening of cardiac hypertrophy. As cardiac failure is usually preceded by a hypertrophic response, perturbations of EETs potentially accelerate deterioration of cardiac hypertrophy towards heart failure. Conversely, cardiac specific overexpression of CYP2J2 mitigates a number of pathological conditions such as arrhythmic susceptibility in cardiac hypertrophy, endoplasmic reticulum stress in heart failure and doxorubicin-induced cardiotoxicity owing to increased production of EETs. Interestingly, CYP2J2 overexpression alleviates the QT prolongation caused by pan-epoxygenase inhibitor, MS-PPOH. This further emphasizes the role of EETs as ion channel regulators. Hence perturbations in the cardiac AA metabolic pathway manifests in dysregulated cardiac homeostasis.

We have previously reported that amiodarone and dronedarone inhibit human cardiac CYP2J2 via mechanism-based inactivation (MBI) and reversible inhibition[7]. We have elucidated that the MBI of CYP2J2 is arbitrated by quinone-oxime metabolite (FIG. 3). To mitigate MBI of CYP2J2, site-directed deuteration of dronedarone was undertaken. Deuteration is a chemical process where at least one hydrogen atom in the molecule is substituted by deuterium. Since deuterium has greater atomic mass, carbon-deuterium(C-D) bond cleavage energy is relatively higher (341.4 kJ/mol) than that of carbon-hydrogen (C—H) bond (338.4 kJ/mol).

Our deuteration experiments were undertaken to produce a product that:

1. reduces MBI potency of CYP2J2 and reduces AA metabolic perturbation.
2. preserves the pharmacokinetic and pharmacodynamic properties of dronedarone and ameliorates its ventricular proarrhythmic property and associated cardiac failure exacerbation.

As a result of our work we have developed a product that comprises site-directed deuteration of dronedarone at positions 4, 6 and 7 of the benzofuran ring (i.e. poyendarone, FIG. 4).

Poyendarone Yields Similar Physicochemical Properties, Effective Permeability and Metabolic Half-Life as its Non-Deuterated Analogue Dronedarone Except for the replacement of hydrogen with deuterium atoms at positions 4, 6 and 7 on benzofuran ring, poyendarone (FIG. 4) and dronedarone (FIG. 1B) are structurally identical. Expectedly, deuteration does not alter the lipophilicity (c Log P), aqueous solubility and effective permeability of poyendarone as compared to dronedarone (Table 8). This implies that both drugs possibly fall within the same class of the Biopharmaceutical Classification System (BCS) defined by USFDA. Additionally, the metabolic half-life ($T_{1/2}$) of poyendarone is comparable to dronedarone. This implies that poyendarone preserves the metabolic stability of dronedarone. Collectively, our findings show the potential preservation of the favourable pharmacokinetic properties of dronedarone by poyendarone.

Down-regulation of CYP2J2 Increases Cardiac Beat-to-Beat Intervals, Confirming That CYP2J2 Inhibition Underpins the Proarrhythmic Effect of Dronedarone Four different siRNAs (Table 1) were used to knockdown human CYP2J2 in human cardiomyocytes (H7 CMs), and all siRNAs knocked down CYP2J2 significantly with siRNA1 being the most effective (FIG. 6).

The knocking down of cardiac CYP2J2 using the four siRNAs increased the beat to beat intervals in individual clusters of cardiomyocytes (FIG. 7). Based on the beat occurrence graph, the beating of the control cardiomyocytes was observed to be regular (FIG. 8). However, upon knocking-down of CYP2J2, the beating of the cardiomyocytes was clearly irregular. When the data points associated with the siRNAs were combined, the increase in the beat to beat intervals was statistically significant (FIG. 9). In summary, these results underscore the pivotal role of CYP2J2 in maintaining cardiac rhythm control and confirms that CYP2J2 inhibition underpins the proarrhythmic effect of dronedarone.

Mechanism-Based inactivation (MBI) of Recombinant Human CYP2J2: Poyendarone <<Dronedarone We previously reported dronedarone and amiodarone as potent mechanism-based inactivators of CYP2J2. As is readily apparent to the skilled artisan, the MBI potency of a drug against an enzyme is substrate-dependent. Our preliminary studies using astemizole as a probe substrate confirmed poyendarone is 62-fold less potent in MBI of CYP2J2 compared to dronedarone (FIG. 10) where their MBI potencies measured as kinact/KI ratios are 0.008 and 0.5 $min^{-1}$ $\mu M^{-1}$ respectively. This finding corroborates our postulation that deuterated quinone-oxime is less reactive. Furthermore, poyendarone is 9-fold less potent than amiodarone (data not shown).

Figures 11A, 11B, 11C, 11D:
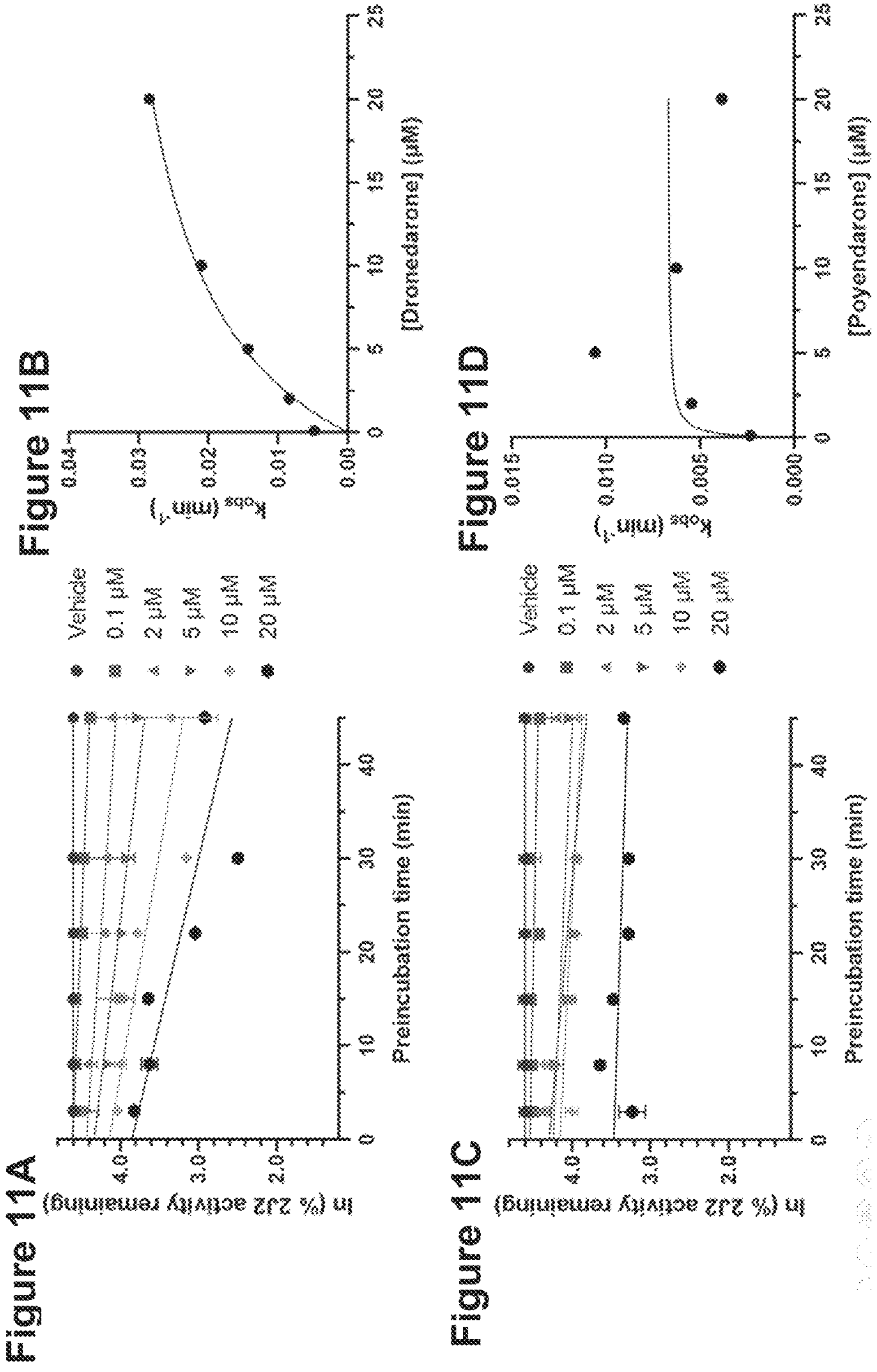
Figure 12A:
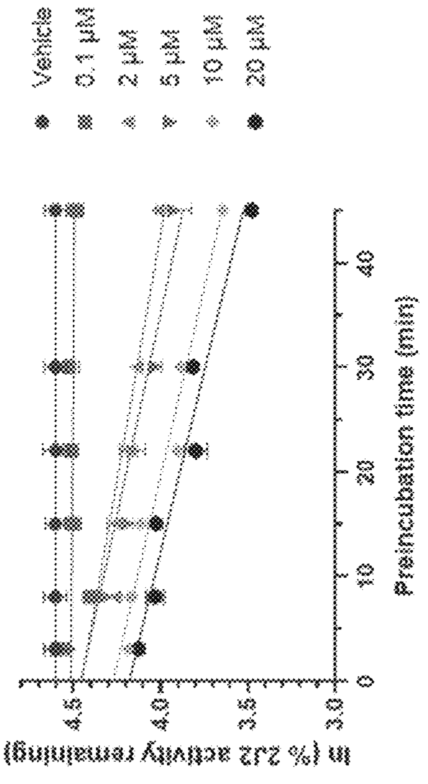
Figure 12B:
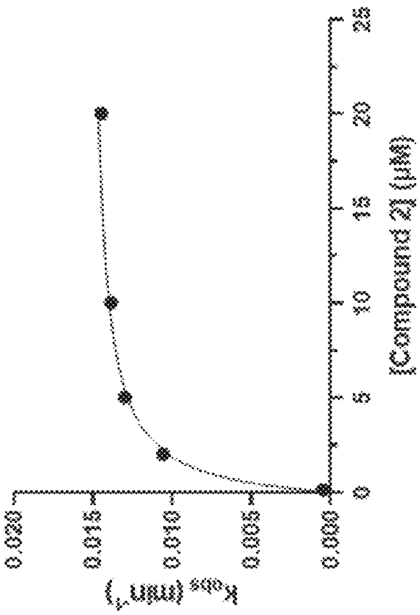
Figure 12C:
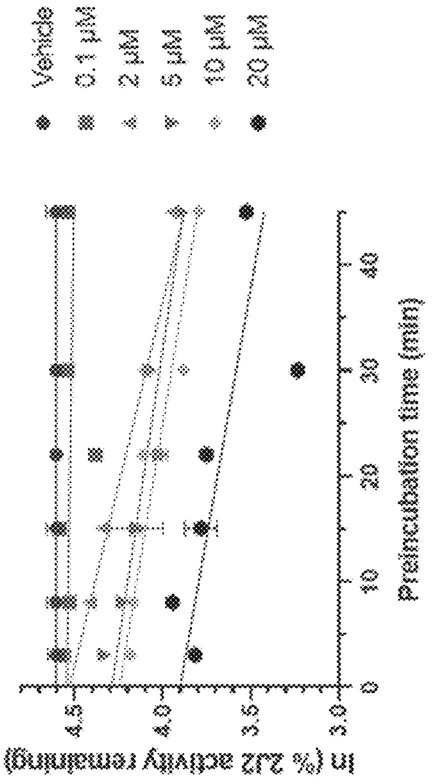
Figure 12D:
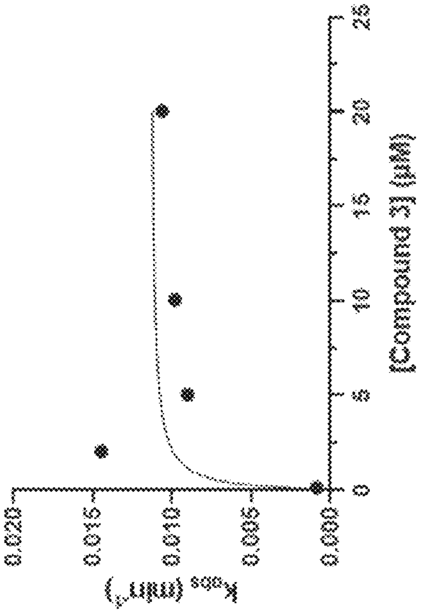

To further validate the MBI potencies of poyendarone, dronedarone and two other deuterated analogues of dronedarone, the clinically relevant rivaroxaban was adopted as a probe substrate. Consistent with the preliminary astemizole-specific MBI data noted above (evidencing an appreciably poor MBI potency of poyendarone), no rivaroxaban-specific MBI could be measured for poyendarone. Specifically, the MBI potencies of poyendarone, dronedarone, compound 1 and compound 2 are summarised in Table 3. Notably. only dronedarone demonstrated inactivation of CYP2J2 (FIG. 11A, 11B) while poyendarone does not cause MBI of CYP2J2 (FIG. 11C, 11D). Compound 2 inactivated CYP2J2 in a time- and concentration-dependent manner (FIG. 12A, 12B), but not Compound 3 (FIG. 12C, 12D). These MBI data obtained using differentially deuterated analogues of dronedarone prove that deuteration of the benzofuran ring is critical for mitigating the MBI of CYP2J2.

Inhibition of CYP2J2 in hiPSC-CM: Poyendarone<<Dronedarone

The hiPSC-cardiomyocytes (hiPSC-CM) are electrophysiologically similar to adult human cardiomyocytes. The spontaneous beating capacity renders hiPSC-CM a desired model to investigate antiarrhythmic activity of established and novel compounds. Additionally, hiPSC-CM are a suitable model to explore the torsadogenic risk of drugs. Here, we investigated if CYP2J2 is expressed in hiPSC-CM and whether our test drugs inhibit CYP2J2 in hiPSC-CM.

To our knowledge, we are the first group to demonstrate CYP2J2 and sEH expression in hiPSC-CM (FIG. 13A). This finding corroborates the established knowledge that CYP2J2 is highly expressed in primary human cardiomyocytes as well as cardiac tissue. Hence, hiPSC-CM are metabolically relevant tools for investigating CYP2J2 biology in vitro. Using them we demonstrated CYP2J2 is indeed active and potently inhibited by dronedarone (98% inhibition) but not amiodarone (FIG. 13B). Lack of inhibition of CYP2J2 by amiodarone is consistent with a previous report[8] using primary human cardiomyocytes. Importantly, the inhibition of CYP2J2 is significantly lower due to poyendarone (50% inhibition) (FIG. 13B).

Poyendarone is Significantly Less Cytotoxic to Cardiomyocytes than Dronedarone

In the absence of pre-treatment using EETs, there was approximately 150-200% increase in the protease activity indicating significant cell death when H9c2 cells were treated with dronedarone (FIG. 14A). In the presence of pre-treatment of H9c2 cells with 14,15-EET, the bis-AAF-R110 fluorescence signal decreased in a concentration-dependent manner, confirming the mitigation of cytotoxicity by the EETs. Similarly, 14,15-EET mitigated the decrease in intracellular ATP levels in a concentration-dependent manner.

Dissipation of $\Delta\psi_m$ was measured using TMRM fluorescent dye. Dronedarone showed potent dissipation of the $\Delta\psi_m$ ($IC_{50}$=0.5 μM). Here, H9c2 cells were pre-treated with 14,15-EET followed by treatment with dronedarone at 5 μM. A concentration-dependent mitigation of $\Delta\psi_m$ dissipation was observed for pre-treatment with 14,15-EET (FIG. 14A).

After exposure of H9c2 cells to dronedarone for 6 h, there was a concentration-dependent increase in the florescence signal, confirming the cytotoxicity of dronedarone against H9c2 cells ($EC_{50}$=1.21 μM) (FIG. 14B). Simultaneously, there was a concentration-dependent decrease in the intracellular ATP levels induced by dronedarone ($IC_{50}$=3.10 μM) (FIG. 14B). Poyendarone is significantly less cytotoxic against H9c2 cells ($EC_{50}$=27.63 μM). Consequently, poyendarone does not reduce ATP levels in H9c2 cells as potently as dronedarone ($IC_{50}$=41.52 μM). Accordingly, at therapeutic plasma concentration (sub-μM) and based on its experimental potencies, poyendarone is expected not to cause cytotoxicity of cardiomyocytes.

Poyendarone Exhibits Ion Channel Blockade Activities Similar to Dronedarone and Amiodarone in hiPSC-CM HiPSC-CM have unique advantage of indefinite propagation and spontaneously beating in culture due to the expression of all the major cardiac ion channels, gap junction proteins and ion exchangers. Thus a wide number of drugs can be tested for their ion channel inhibitory properties. Unlike the conventional patch-clamp methodology (FIG. 15A), in this study we have used MEA system (FIG. 15B) to measure the 'global' effect of drugs on the extracellular field potential duration (FPD) reflective of the cardiac action potentials. The advantage of MEA is profiling of group of cells instead of a single cell thus avoiding bias. Notably, poyendarone demonstrates a similar concentration-dependent effect on extracellular field potential duration (FPD) using multielectrode array (MEA) assay of electrophysiologically-relevant hiPSC-CMs (FIG. 15B, FIG. 15C).

In addition, it is shown that poyendarone, dronedarone and amiodarone possess similar inhibitory potency of human cardiac Nav1.5 (FIGS. 16, 17 and 18), Cav1.2 (FIGS. 19, 20 and 21) and $K_v11.1$ (FIGS. 22, 23 and 24) based on patch-clamp experiments. These evidences confirm the anti-AF pharmacology of poyendarone.

Poyendarone has Lower Proarrhythmic Risk Compared to Dronedarone in hiPSC-CM

It is known that Class III antiarrhythmics, whilst effective for the treatment of atrial arrhythmias, can paradoxically increase the risk of life-threatening ventricular arrhythmias. Hence it is important to distinguish between the proarrhythmic and antiarrhythmic effects of potassium channel blockers. Traditionally, hERG inhibition and QT prolongation are used as markers for drug-induced proarrhythmia. Specifically, QT prolongation accompanied by instability can predict drug-induced proarrhythmia while QT prolongation in the absence of instability is antiarrythmic. Instability can be assessed in hiPSC-CM by measuring the beat-to-beat variability (BBV). BBV can be visualized graphically using Poincaré plot. The Poincaré plot is a chart in which each R-R interval or inter-beat interval (IBI) is plotted against its predecessor and displays the correlation between consecutive intervals in a graphic manner (FIG. 25). IBIs in control and poyendarone cluster around the centroid of the ellipse and align to the longitudinal axis defined as cigar-shaped plot (FIG. 25). This is indicative of least variability among the beats. However, the IBIs do not cluster at the centroid of the ellipse and diffuse across the plot in case of dronedarone (FIG. 25).

Poyendarone has Similar In Vivo Plasma Pharmacokinetics as Dronedarone

Similar disposition profiles and primary pharmacokinetics parameters (clearance and volume of distribution) were observed between poyendarone and dronedarone dosed at 3.0 mg/kg. No acute toxicity nor fatality was observed in vivo (FIG. 26).

Poyendarone has Similar Simulated In Vivo Human Pharmacokinetics as Dronedarone

To enhance PK understanding of poyendarone, a PBPK model was constructed. Deriving accurate $CL_{int}$ and $k_{inact}/K_I$ values for input into each PBPK model mechanistically accounts for the elimination and time-dependency of the predicted plasma concentration-time profile of each drug. Additionally, generating these in vitro human data further ensures that the predicted profiles are as generalizable as possible toward different populations of interest.

Figure 27A:
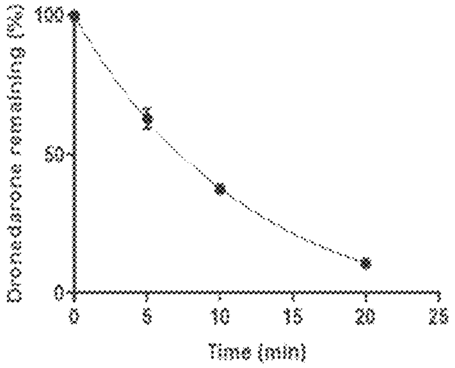
Figure 27B:
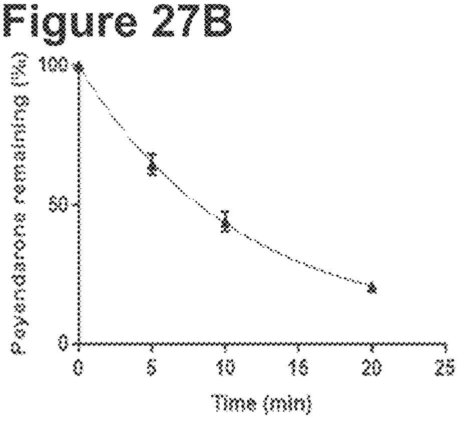
Figure 27C:
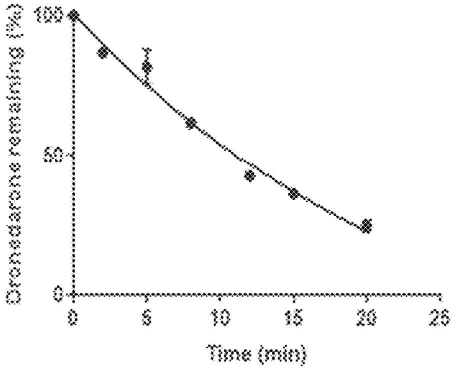
Figure 27D:
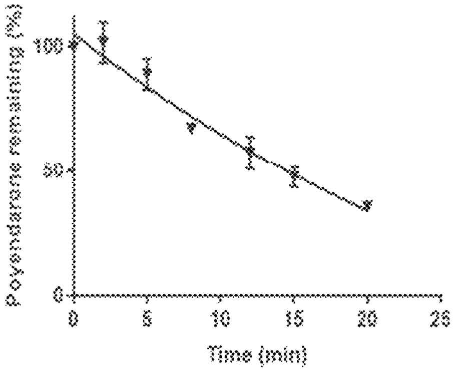
Figure 27E:
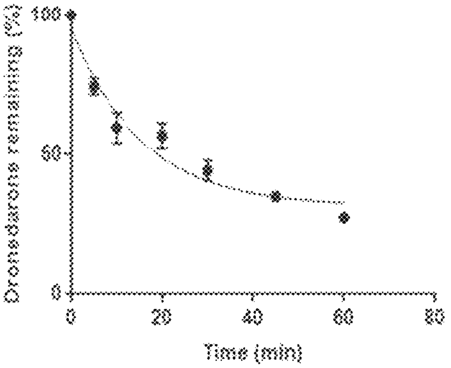
Figure 27F:
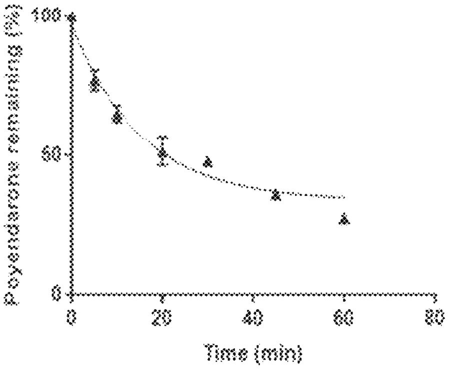
Figures 28A, 28B, 28C, 28D, 28E, 28F, 28G, 28H, 28I, 28J:
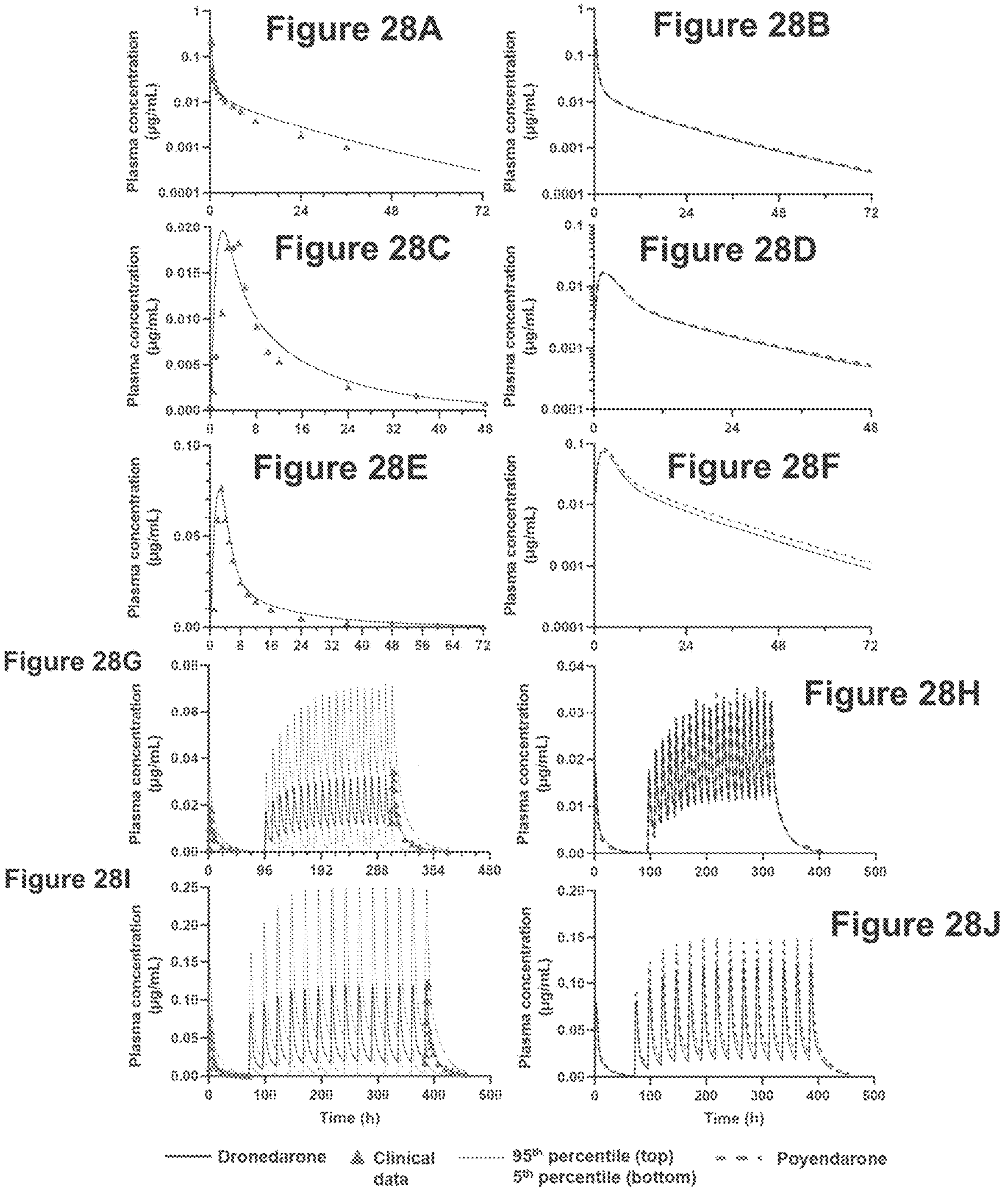

Metabolic stability study. The percentage of substrate remaining in the CYP3A4, CYP3A5 or HLM reaction mixture decreased monoexponentially as the incubation time progressed over time. The $T_{1/2}$ and k for dronedarone were 16.73 min and 0.04144 $min^{-1}$ by CYP3A4, 17.37 min and 0.03989 $min^{-1}$ by CYP3A5, and 10.75 min and 0.06446 $min^{-1}$ by HLM (FIG. 27A, 27C, 27E respectively). The $T_{1/2}$ and k for poyendarone were 7.551 min and 0.0918 $min^{-1}$ by CYP3A4, 25.14 min and 0.02757 $min^{-1}$ by CYP3A5, and 10.71 min and 0.06472 $min^{-1}$ by HLM (FIG. 27B, 27D, 27 respectively). Across all enzyme systems, the $CL_{int}$ values obtained for dronedarone were similar to that of poyendarone (Table 6). The experimental $CL_{int}$ values of poyendarone (CYP3A4: 9.18 μL/min/pmol; CYP3A5: 2.757 μL/min/pmol) were expectedly similar to that of dronedarone (CYP3A4: 8.288 μL/min/pmol; CYP3A5: 3.989 μL/min/pmol), since the sites of deuteration are distant from the main site of metabolism in dronedarone (the N-butyl chains). In addition, the experimental $CL_{int}$ values of dronedarone are similar to the values reported by Hong et al. using a similar experimental set-up (CYP3A4: 6.442 μL/min/pmol; CYP3A5: 2.604 μL/min/pmol)[10], corroborating their validity to be used for PBPK modelling.

Time- and concentration-dependent inactivation of CYP3A4, CYP3A5, CYP2J2. Dronedarone and poyendarone inactivated CYP3A4 and CYP3A5 in a time- and concentration-dependent manner with rivaroxaban as the probe substrate (Table 6). The concentration-dependency of inactivation can be seen in the saturation kinetics of $k_{obs}$ calculated from various concentration levels of inactivator, where a maximum rate of inactivation was approached as inactivator concentration increased. Dronedarone and poyendarone had similar $k_{inact}/K_I$ values for CYP3A5, but that of poyendarone was higher than that of dronedarone for CYP3A4 (2.4-fold difference) (Table 6).

Figures 29A, 29B, 29C, 29D:
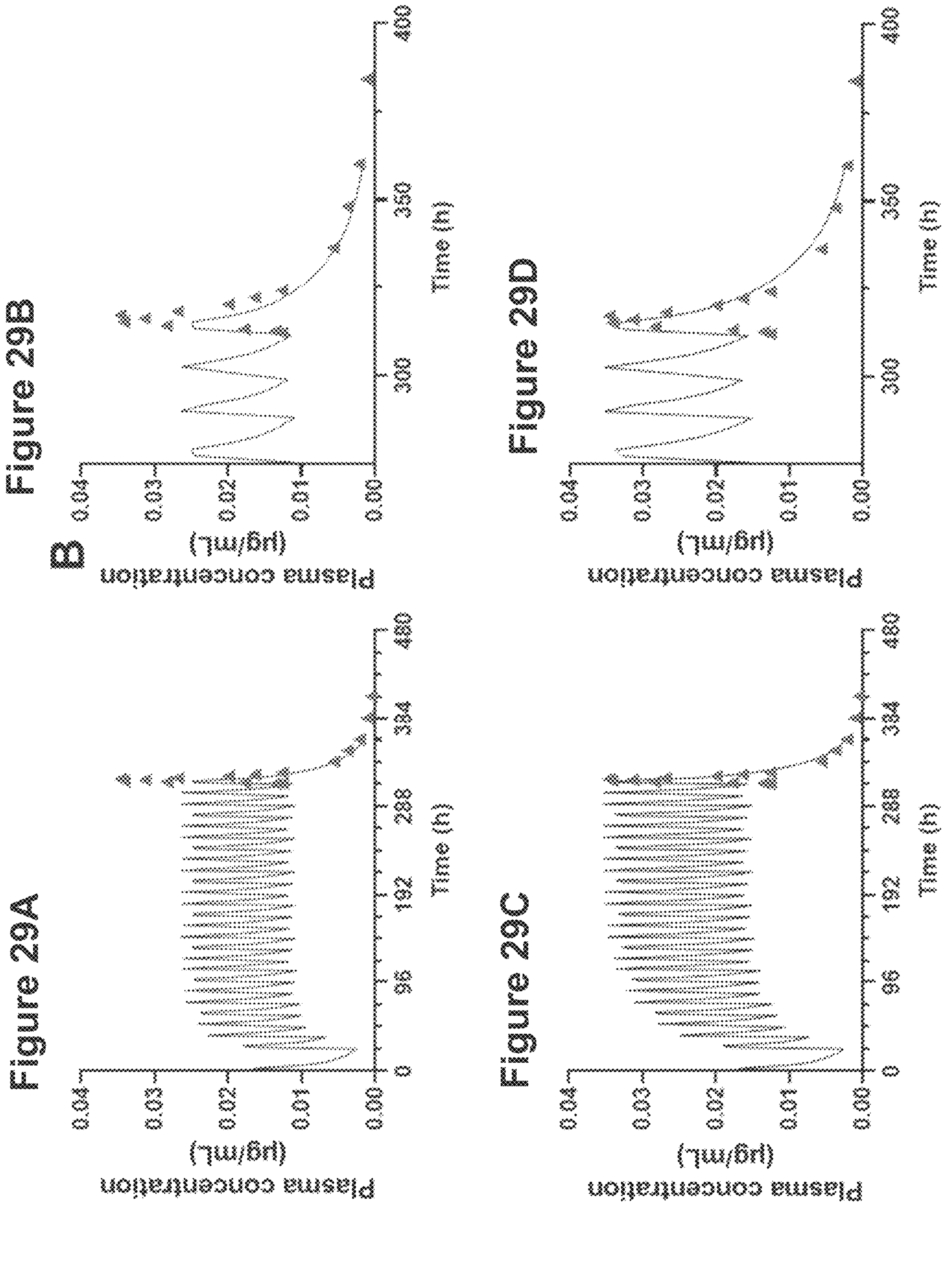

Development and verification of PBPK models. Our PBPK model characterized the clinical data of dronedarone successfully not just for intravenous and single oral dosing, but also multiple oral dosing where AUC is recapitulated within ~12% error in fasted state and ~34% in fed state (FIG. 28). The predicted PK parameters were compared with the clinical data based on the relevant success criteria. It is also intriguing to note that the satisfactory fitting of simulated multiple oral dosing data to clinical data (FIG. 29A, 29B) is lost when the effects of MBI are not simulated (FIG. 29C, 29D). This underscores the importance of integrating accurate MBI data into PBPK modelling for the successful prediction of time-dependent PK of dronedarone.

Dronedarone and poyendarone yield similar MBI potencies against CYP3A5 (0.00634 $\mu M^{-1}$ $min^{-1}$ and 0.00793 $\mu M^{-1}$ $min^{-1}$ respectfully, Table 6), but less so for CYP3A4 (0.00505 $\mu M^{-1}$ $min^{-1}$ and 0.0123 $\mu M^{-1}$ $min^{-1}$ respectively, Table 6). CYP3A4 is the major metabolising enzyme of dronedarone as compared to CYP3A5. This is likely the case for poyendarone as well since its metabolic hotspot is not deuterated. Taken together, we postulate that poyendarone would have a more potent MBI effect against its key metabolizing enzyme, culminating in a greater autoinhibition of CYP3A4 and thus resulting in higher systemic exposure. However, based on read-across PBPK modelling, the simulated multiple oral dosing of poyendarone differed only slightly from that of dronedarone. Indeed, given that the usual dose of dronedarone is 400 mg twice a day with food, provided that poyendarone has the same potency as dronedarone, it is likely that no dosage adjustment would be expected for poyendarone.

Here, the findings demonstrated for the first time the experimental framework of read-across PBPK modelling to predict the clinical PK profile of poyendarone based on verified PBPK model of dronedarone. Based on the augmented systemic exposure of poyendarone and assuming its comparable exposure-efficacy relationship as dronedarone, a dosing regimen can be subsequently designed for the first-in-human trial of payendarone.

Poyendarone Preserves Potential Anti-Atrial Fibrillatory Effects

Similar to dronedarone and amiodarone, poyendarone prolongs both AERP and VERP, and yields 1.8-2.7 times greater atrial selectivity (Table 9). This underscores its potential clinical efficacy against atrial arrhythmias.

Poyendarone Circumvents Potential Proarrhythmic Effects Associated with Dronedarone Poyendarone shows the lowest risk of re-entrant ventricular arrhythmias based on its lowest effect on terminal repolarization period (ΔTRP). Lack of early repolarization prolongation (ΔJ-Tpeakc) and minimal prolongation of late repolarization period (ΔTpeak-Tend) underscores potential low risk of Torsade de pointes associated with poyendarone (Table 10).

Poyendarone Possess Favourable Atrial Electropharmacological Properties as an Anti-Atrial Fibrillatory Drug in Paroxysmal AF Canine Model No animals exerted any lethal ventricular arrhythmias or hemodynamic collapse leading to their death during the experimental period.

Effects on the sinoatrial rate and mean blood pressure. The time courses of changes in the sinoatrial rate and mean blood pressure are summarized in FIG. 30. Their pre-drug basal control values (C) were 96±12 bpm and 83±12 mmHg, respectively. The low dose of 0.3 mg/kg as well as the high dose of 3 mg/kg hardly altered any of these variables.

Effects on the IACT. The time courses of changes in the ACT are summarized in FIG. 31. The pre-drug basal control values (C) of the $IACT_{(CL400)}$, $IACT_{(CL300)}$ and $IACT_{(CL200)}$ were 44±2 ms, 47±1 ms and 55±2 ms, respectively. The low dose did not alter these ACT values at any of the pacing cycle lengths. The high dose prolonged the $IACT_{(CL400)}$ at 10 min and for 30-60 min, the $IACT_{(CL300)}$ at 10 min, and the $IACT_{(CL200)}$ for 10-60 min.

Effects on the AERP and VERP. The time courses of changes in the AERP and VERP are summarized in FIG. 31. The pre-drug basal control values (C) of the $AERP_{(CL400)}$, $AERP_{(CL300)}$, $AERP_{(CL200)}$ and $VERP_{(CL400)}$ were 150±11 ms, 145±12 ms, 139±14 ms and 233±6 ms, respectively. The low dose prolonged the $AERP_{(CL400)}$ at 20 min, whereas no significant change was detected in the other variables. The high dose prolonged the $AERP_{(CL400)}$ and $AERP_{(CL300)}$ for 10-60 min, whereas no significant change was detected in the $AERP_{(CL200)}$ or $VERP_{(CL400)}$.

Figure 32:
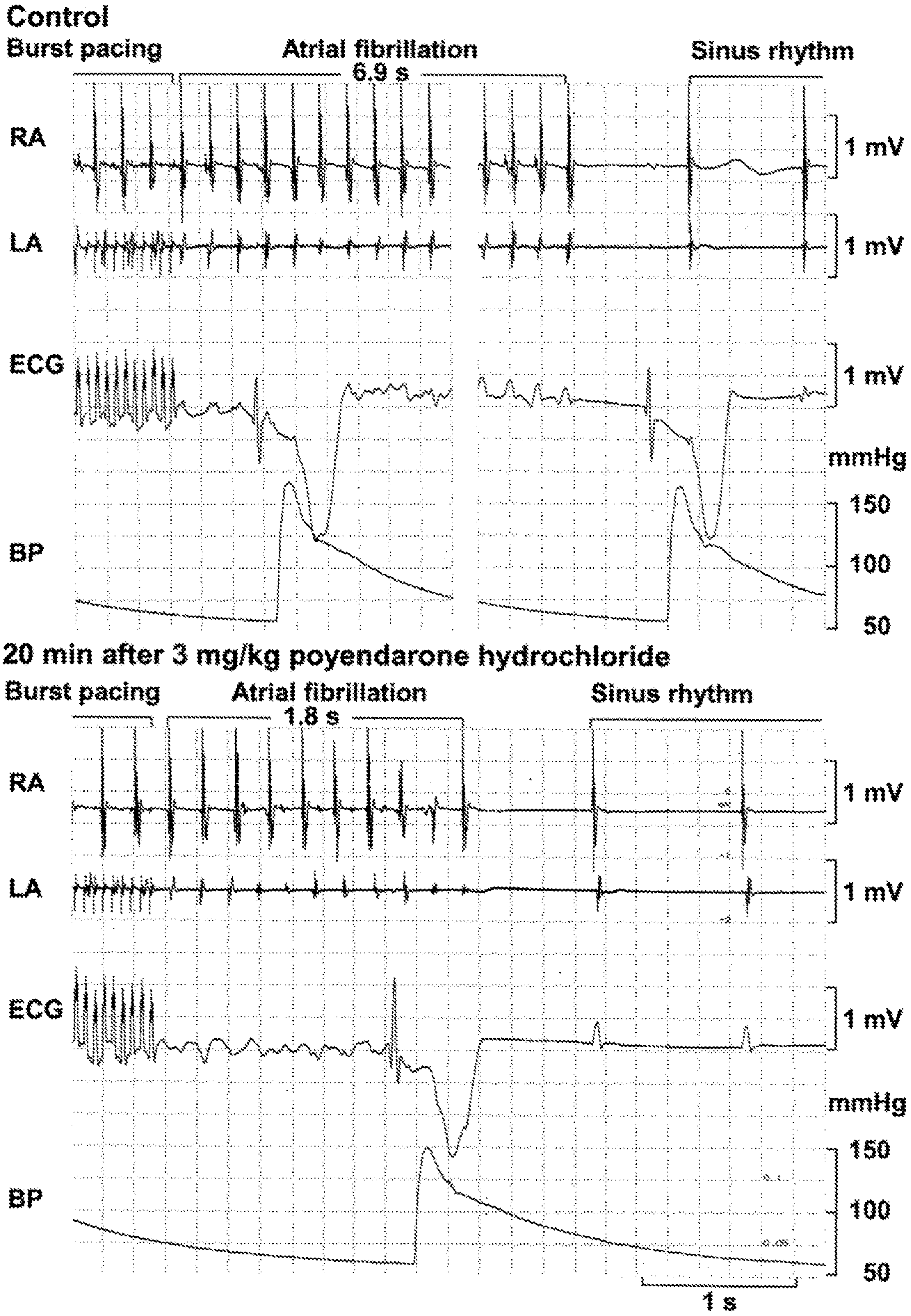

Effects on the duration and cycle length of atrial fibrillation. Typical tracings of the right and left atrial electrograms, electrocardiogram and arterial blood pressure during and after the burst pacing are depicted in FIG. 32, whereas the time courses of changes in the duration and cycle length of atrial fibrillation are summarized in FIG. 33. Their pre-drug basal control values (C) were 4.0±0.9 s and 155±15 ms, respectively. The low dose did not alter these variables. The high dose shortened the duration for 10-60 min, whereas the cycle length was tended to be prolonged, which did not achieve statistical significance.

In summary, poyendarone has atrial-selective, anti-atrial fibrillatory effects against paroxysmal atrial fibrillation in canines.

Summary

Our compelling in vitro and in vivo evidence confirms that site-directed deuteration is a viable strategy to optimize the safety and efficacy of benzofuran derived antiarrhythmic drugs such as dronedarone.

The site-specific deuterated compound poyendarone demonstrates:

- similar physicochemical, permeability and metabolic stability as dronedarone,
- comparable cardiac ion channel blockage activities as dronedarone,
- favourable pharmacokinetics similar to dronedarone, and
- comparable in vivo anti-atrial fibrillatory selectivity and activity as dronedarone.

Further, unlike dronedarone, the site-specific deuterated compound poyendarone does not cause:

- inactivation of human cardiac CYP2J2,
- mitochondrial dysfunction in cardiomyocytes, and instead yields a safer cytotoxicity/ATP depletion profile, which indicates a reduced cardiotoxicity risk in comparison to dronedarone,
- BBV in hiPSC-CM, and
- potential cardiac proarrhythmic risk in vivo.

Therefore, site-specific deuterated benzofuran derived antiarrhythmic drugs, in particular poyendarone, are/is a viable asset for the treatment of AF.

TABLE 1

| siRNA Targets/ qPCR Primers | Sequences | Sequence ID |
|---|---|---|
| CYP2J2 siRNA1 (A-008208-13) | CUCAGGUGUAAUAUUGUUA | SEQ ID NO: 1 |
| CYP2J2 SIRNA2 (A-008208-14) | GUCACAUACUUGGAGGCUU | SEQ ID NO: 2 |
| CYP2J2 siRNA3 (A-008208-15) | CCUGGAGGUUCAGCUGUUU | SEQ ID NO: 3 |
| CYP2J2 siRNA4 (A-008208-16) | UGGUGAGCUUUAAGUGGUU | SEQ ID NO: 4 |
| CYP2J2 qPCR Primer Forward | GAGCTTAGAGGAACGCATT CAG | SEQ ID NO: 5 |
| CYP2J2 qPCR Primer Reverse | GAAATGAGGGTCAAAAGGC TGT | SEQ ID NO: 6 |

TABLE 1-continued

| siRNA Targets/ qPCR Primers | Sequences | Sequence ID |
|---|---|---|
| B-ACTIN qPCR Primer Forward | CCCATCGAGCATGGTATCA TC | SEQ ID NO: 7 |
| B-ACTIN qPCR Primer Reverse | AGAAGCATACAGGGATAGC ACT | SEQ ID NO: 8 |

TABLE 2

| Compound Nomenclature | Q1 Mass (m/z) | Q3 Mass (m/z) | DP (Volts) | EP (Volts) | CE (Volts) | CXP (Volts) |
|---|---|---|---|---|---|---|
| O-desmethyl-astemizole | 445 | 121 | 131 | 10 | 41 | 8 |
| Buspirone | 386 | 122 | 100 | 10 | 37 | 8 |

Q1 Mass: Mass of parent ion
EP: Entrance potential
Q3 Mass: Mass of daughter ion
CE: Collision energy
DP: Declustering potential
CXP: Collision cell exit potential

TABLE 3

| Compound | Structure | MBI potency ($K_{inact}/K_I$ $\mu M^{-1} \cdot min^{-1}$) against human recombinant CYP2J2[a] | Comment |
|---|---|---|---|
| Poyendarone | 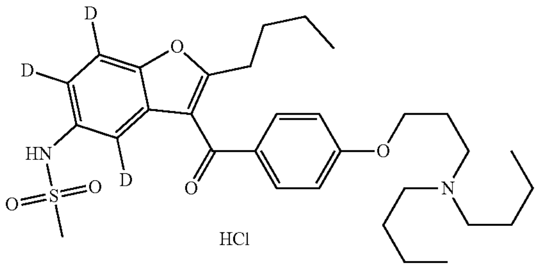 [SMILES: [2H]c1c(NS(C)(=O)=O)c([2H])c2c(C(=O)c3ccc(OCCCN(CCCC)CCCC)cc3)c(CCCC)oc2c1[2H] ; Cl] HCl | No MBI | Deuteration of benzofuran ring mitigates formation of quinone-oxime reactive metabolite and MBI of CYP2J2. |
| Dronedarone | 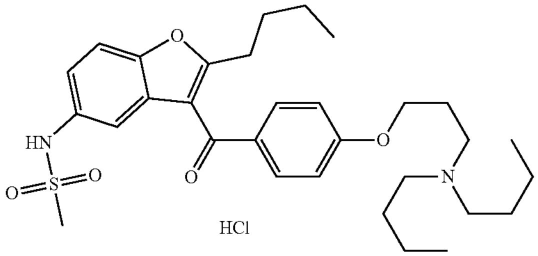 [SMILES: CCCCc1oc2ccc(NS(C)(=O)=O)cc2c1C(=O)c1ccc(OCCCN(CCCC)CCCC)cc1 ; Cl] HCl | 0.01909 | Quinone-oxime reactive metabolite derived from benzofuran ring causes MBI of CYP2J2. |
| Compound 2 | 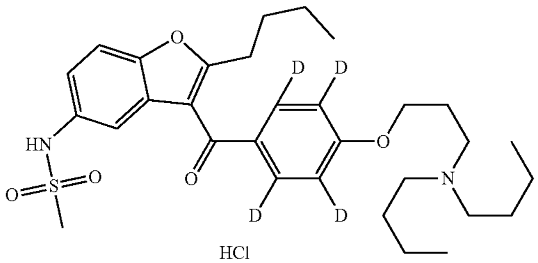 [SMILES: [2H]c1c([2H])c(C(=O)c2c(CCCC)oc3ccc(NS(C)(=O)=O)cc23)c([2H])c([2H])c1OCCCN(CCCC)CCCC ; Cl] HCl | 0.005643 | Quinone-oxime reactive metabolite derived from benzofuran ring causes MBI of CYP2J2. Deuteration of benzyl ring reduces MBI potency by 3.4-fold but does not eliminate the MBI effect. |

TABLE 3-continued

| Compound | Structure | MBI potency ($K_{inact}/K_I$ $\mu M^{-1}\cdot min^{-1}$) against human recombinant CYP2J2[a] | Comment |
|---|---|---|---|
| Compound 3 | 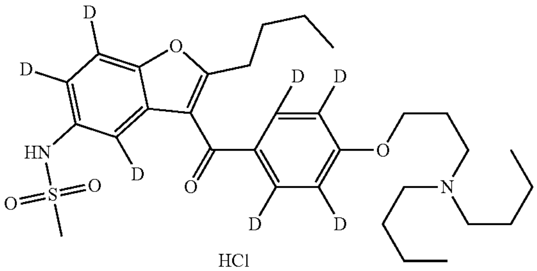 [SMILES: [2H]c1c([2H])c(C(=O)c2c(CCCC)oc3c([2H])c([2H])c(NS(C)(=O)=O)c([2H])c23)c([2H])c([2H])c1OCCCN(CCCC)CCCC ; Cl] HCl | No MBI | Deuteration of benzofuran ring mitigates formation of quinone-oxime reactive metabolite and MBI of CYP2J2. The confirms deuteration of benzofuran ring is critical in eliminating the MBI of CYP2J2. |

TABLE 4

| Gene | Forward sequence (5' → 3') | Reverse sequence (5' → 3') | References |
|---|---|---|---|
| CYP2J2 | GAGCTTAGAGGAACGCATT CAG (SEQ ID NO: 9) | GAAATGAGGGTCAAAAGG CTGT (SEQ ID NO: 10) | PrimerBank ID: 18491007c3 |
| EPHX2 | GACAAGGCGATTTCAGCC AGA (SEQ ID NO: 11) | GGTTCAGGTTTGACCATTC CC (SEQ ID NO: 12) | PrimerBank ID: 374532798c2 |
| GAPDH | GGCTGTTGTCATACTTCTC ATGG (SEQ ID NO: 13) | GGCTGTTGTCATACTTCTC ATGG (SEQ ID NO: 14) | PrimerBank ID: 378404907c1 |

TABLE 5

| A | |
|---|---|
| Flow rate (mL/min) | 0.6 |
| Curtain gas (psi) | 25 |
| Collision gas | Medium |
| Ion-spray voltage (V) | 5500 |
| Temperature (° C.) | 550° C. |
| Ion source gas 1 (psi) | 50 |
| Ion source gas 2 (psi) | 55 |

TABLE 5-continued

B

| Compound | Q1 (m/z) | Q3 (m/z) | DP (V) | EP (V) | CE (V) | CXP (V) |
|---|---|---|---|---|---|---|
| Dronedarone | 557 | 100 | 80 | 10 | 46 | 7 |
| Poyendarone | 560 | 438 | 110 | 12 | 41 | 16 |
| | | 142 | | | 45 | 8 |
| NDEA (IS) | 618 | 547 | 201 | 10 | 29 | 12 |
| | | 313 | | | 49 | 18 |

TABLE 6

| | Intrinsic clearance, $CL_{int}$ | | | $k_{inact}/K_I$ ($\mu M^{-1}$ $min^{-1}$) | |
|---|---|---|---|---|---|
| | CYP3A4 | CYP3A5 | HLM | | |
| Substrate | (μL/min/pmol) | | (μL/min/mg) | CYP3A4 | CYP3A5 |
| Dronedarone | 8.29 | 3.99 | 128.92 | $5.05\times10^{-3}$ | $6.34\times10^{-3}$ |
| Poyendarone | 9.18 | 2.76 | 129.44 | $1.23\times10^{-2}$ | $7.93\times10^{-3}$ |

TABLE 7

| | Dronedarone | Poyendarone |
|---|---|---|
| Physicochemical properties | | |
| Molecular Weight (g/mol) | 556.76 | 559.76 |
| log P | 6.46 | 6.442 |
| Compound type | Monoprotic base as deduced from chemical structures. | |
| $pK_a$ | 9.4 | 9.4 (assumed) |
| B/P | 1.5[1] | 1.5 (assumed) |
| $f_u$ | 0.003 | 0.003 (assumed) |
| Absorption: ADAM model | | |
| $f_{u,gut}$ | 0.000136127^ | 0.000136626^ |
| Caco-2 permeability ($\times 10^{-6}$ cm/s) | 0.595 | 0.595 (assumed) |
| Formulation | Solid, immediate release (assumed) | Solid, immediate release (assumed) |
| Intrinsic solubility (mg/mL) | $2.01 \times 10^{-3}$ (using ALOGPS 2.1) | $2.01 \times 10^{-3}$ (assumed) |
| Solubility-pH profile (mg/mL) | At pH 3, 4, 5, 6, 7: 1.6, 1.6, 1.5, 0.1,n 0.01 | N.A. |
| Distribution: full PBPK model | | |
| $V_{ss}$ (L/kg) | Method 2 used 16.3089 (based on $K_p$ values below) | Method 2 used 16.0789 (based on $K_p$ values below) |
| $K_p$ of tissues: | | |
| Adipose | 1 | 1 |
| Heart | 1 | 1 |
| Kidney | 1 | 1 |
| Liver | 38.05 | 38.05 (assumed) |
| Lung | 64.01 | 64.01 (assumed) |
| $K_p$ for other organs | Simcyp default values | Simcyp default values |
| $K_p$ scalar | 1 | 1 |
| Elimination | | |
| $CL_{int}$ (CYP3A4) (μL/min/mg microsomal protein) | 114.739* | 115.2016* |
| $CL_{int}$ (CYP3A5) (μL/min/mg microsomal protein) | 14.1812* | 14.2384* |
| Additional HLM clearance (μL/min/mg microsomal protein) | 55 (optimised via sensitivity analysis) | 55 (assumed) |

TABLE 7-continued

| | Dronedarone | Poyendarone |
|---|---|---|
| $f_{u,mic}$ ($f_{u,inc}$) | 0.003 (assumed to equal $f_u$) | 0.003 (assume same) |
| Renal clearance (L/h) | 0 | 0 |
| Additional systemic clearance (L/h) | 0 | 0 |
| Interaction Reversible inhibition $K_i$ (μM) | | |
| CYP3A4 | 0.64 | 0.64 |
| CYP2J2 | 0.93 | 0.93 |
| CYP2C9 | N.A. | N.A. |
| CYP2D6 | N.A. | N.A. |
| $f_{u,mic}$ | 0.003 | 0.003 (assume same as dronedarone) |
| Mechanism-based inactivation $K_I$ (μM), $K_{inact}$ ($h^{-1}$) | | |
| CYP3A4 | 5.3*, 1.6044* | 3.185*, 2.3532* |
| CYP3A5 | 5.369*, 2.0436* | 2.907*, 1.3836* |
| $f_{u,mic}$ | 0.003 | 0.003 (assume) |

*In vitro data obtained.

^Predicted by SimCYP.

N.A. = not applicable (data not entered).

[1]A value of 1 was first inferred from animal data in the Multaq analytical dossier [33]. Given that the human plasma clearance of dronedarone reported by most studies is ~140 L/h [8, 27], the (B/P) × $f_m$ needs to be at least ~1.5 to ensure that $CL_{b,h}$ does not exceed $Q_H$ (81 L/h per 70 kg in a male). Since the $f_m$ of dronedarone is ~1 [27], it is reasonable to assume that B/P needs to be at least 1.5.

[2]For poyendarone: Since the metabolism of dronedarone is mainly via N-debutylation which is unaffected by deuteration at an unrelated functional group, the extent to which poyendarone undergoes hepatic first-pass should be the same as that of dronedarone. We can further assume that the overall first-pass effect (including gut metabolism) is relatively unchanged from that of dronedarone, assuming that hepatic metabolism contributes much more to the first-pass effect than gut metabolism.

TABLE 8

| Properties | Poyendarone | Dronedarone |
|---|---|---|
| cLogP | 7.2 | 7.2 |
| Aqueous Solubility | 2.43 μg/mL | 3.22 μg/mL |
| Effective permeability | $4.08 \pm 0.5 \times 10^{-6}$ cm · $s^{-1}$ | $3.46 \pm 0.5 \times 10^{-6}$ cm · $s^{-1}$ |
| Metabolic half-life ( $T_{1/2}$) | 5.32 min | 4.95 min |

TABLE 9

| Drugs (Time after administration) | Poyendarone hydrochloride (30 min, 45 min) | Dronedarone hydrochloride (20 min) | Amiodarone hydrochloride (10 min) | Bepridil hydrochloride (10 min) | dl-Sotalol hydrochloride (20 min, 30 min) |
|---|---|---|---|---|---|
| Dose (mg/kg, i.v.) | 3 | 3 | 3 | 3 | 3 |
| ΔAERP (ms) | +25, +34 | +43 | +29 | +53 | +60, +56 |
| ΔVERP (ms) | +14, +13 | +23 | +18 | +55 | +53, +54 |
| Atrial selectivity (ΔAERP/ΔVERP) | 1.8, 2.7 | 1.9 | 1.6 | 1.0 | 1.1, 1.0 |

TABLE 10

| Drugs (Time after administration) | Poyendarone hydrochloride (45 min) | Dronedarone hydrochloride (60 min) | Amiodarone hydrochloride (15 min) | Bepridil hydrochloride (20 min) | dl-Sotalol hydrochloride (10 min) |
|---|---|---|---|---|---|
| Dose (mg/kg, i.v.) | 3 | 3 | 3 | 3 | 3 |
| ΔTRP (ms) | −13 | +11 | −11 | +4 | −1 |
| $\Delta J\text{-}T_{peak}{}^{c}$ | −5 | +7 | −10 | +31 | +35 |
| $\Delta T_{peak}\text{-}T_{end}$ (ms) | +1 | +28 | +18 | +14 | +17 |

REFERENCES

1. A. Mehta, Y.Y. Chung, A. Ng, F. Iskandar, S. Atan, H. Wei, et al., Pharmacological response of human cardiomyocytes derived from virus-free induced pluripotent stem cells., *Cardiovasc. Res.* 91 (2011) 577-586. doi:10.1093/cvr/cvr132.
2. A. Mehta, Y. Chung, G. L. Sequiera, P. Wong, R. Liew, W. Shim, Pharmacoelectrophysiology of viral-free induced pluripotent stem cell-derived human cardiomyocytes, *Toxicol. Sci.* 131 (2013) 458-69. doi:10.1093/toxsci/kfs309.
3. L. Zwi, O. Caspi, G. Arbel, I. Huber, A. Gepstein, I.-H. Park, L. Gepstein, Cardiomyocyte differentiation of human induced pluripotent stem cells., *Circulation.* 120 (2009) 1513-23. doi:10.1161/CIRCULATIONAHA.109.868885.
4. M. P. Tarvainen, J.-P. Niskanen, J. A. Lipponen, P. O. Ranta-aho, P. A. Karjalainen, Kubios HRV—Heart rate variability analysis software, *Comput. Methods Programs Biomed.* 113 (2014) 210-20. doi:10.1016/j.cmpb.2013.07.024.
5. A. Voss, S. Schulz, R. Schroeder, M. Baumert, P. Caminal, Methods derived from nonlinear dynamics for analysing heart rate variability., *Philos. Trans. A. Math. Phys. Eng. Sci.* 367 (2009) 277-96. doi:10.1098/rsta.2008.0232.
6. Y. Motokawa, Y. Nakamura, M. H. Nagasawa, A. Goto, K. Chiba, N. J. Lubna, H. I. Nakaseko, K. Ando, A.T. Naito, H. Yamazaki, A. Sugiyama, In vivo analysis of the anti-atrial fibrillatory, proarrhythmic and cardiodepressive profile of dronedarone as a guide for safety pharmacological evaluation of antiarrhythmic drugs., *Cardiovasc. Toxicol.* 18 (2018) 242-51. doi: 10.1007/s12012-017-9434-y.
7. A. Karkhanis, H. Y. Lam, G. Venkatesan, S. K. Koh, C. L. L. Chai, L. Zhou, Y. Hong, P. Kojodjojo, E C Y Chan, Multiple modes of inhibition of human cytochrome P450 2J2 by dronedarone, amiodarone and their active metabolites., *Biochem. Pharmacol.* 107 (2016) 67-80. doi: 10.1016/j.bcp.2016.03.005.
8. E.A. Evangelista, R. Kaspera, N. A. Mokadam, J. P. Jones, R. A. Totah, Activity, Inhibition, and Induction of Cytochrome P450 2J2 in Adult Human Primary Cardiomyocytes., *Drug. Metab. Dispos.* 41 (2013) 2087-94. doi: 10.1124/dmd.113.053389.
9. K. Abduljalil, T. Cain, H. Humphries, A. Rostami-Hodjegan, Deciding on success criteria for predictability of pharmacokinetic parameters from in vitro studies: An analysis based on in vivo observations., *Drug. Metab. Dispos.* 42 (2014) 1478-84. doi: 10.1124/dmd.114.058099.
10. Y. Hong, Y. M. F. Chia, R. H. Yeo, G. Venkatesan, S.K. Koh, C. L. L. Chai, L. Zhou, P. Kojodjojo, E. C. Y. Chan, Inactivation of human cytochrome P450 3A4 and 3A5 by dronedarone and n-desbutyl dronedarone., *Mol. Pharmacol.* 89 (2016)1-13. doi: 10.1124/mol.115.100891.
11. A. Sugiyama, Y. Ishida, Y. Satoh, S. Aoki, M. Hori, Y. Akie, Y. Kobayashi, K. Hashimoto, Electrophysiological, anatomical and histological remodeling of the heart to AV block enhances susceptibility to arrhythmogenic effects of QT-prolonging drugs., *Jpn J Pharmacol.* 88 (2002) 341-50. doi:10.1254/jjp.88.341.
12. K. Wang, A. Takahara, Y. Nakamura, K. Aonuma, M. Matsumoto, A. Sugiyama, In vivo electropharmacological effects of amiodarone and candesartan on atria of chronic atrioventricular block dogs., *J. Pharmacol. Sci.* 103 (2007) 207-13. doi: 10.1254/jphs.FP0060945.
13. H. Iwasaki, A. Takahara, Y. Nakamura, Y. Satoh, T. Nagai, N. Shinkai, A. Sugiyama. Simultaneous assessment of Pharmacokinetics of Pilsicainide transdermal patch and its electropharmacological effects on atria of chronic atrioventricular block dogs., *J. Pharmacol. Sci.* 110 (2009) 410-14. doi:10.1254/jphs.09061sc.
14. A. Sugiyama, Sensitive and reliable proarrhythmia in vivo animal models for predicting drug-induced torsades de pointes in patients with remodelled hearts. *Br. J. Pharmacol.* 154 (2008) 1528-37. doi: 10.1038/bjp.2008.240.

The invention claimed is:

1. A compound according to Formula (I) or a pharmaceutically acceptable salt thereof:

Formula (I)

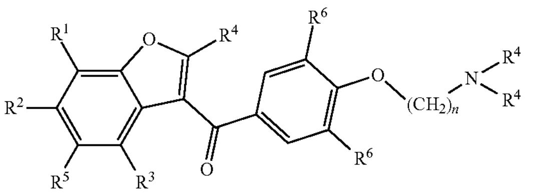

wherein:

$R^1$, $R^2$ and $R^3$ each represents deuterium;

n represents 2 or 3;

each $R^4$ independently represents a $C_{1-6}$ hydrocarbyl group which may be substituted with one or more of nitro, halogen, amino, amido, cyano, carboxyl, sulphonyl, hydroxyl, ketone or aldehyde groups;

$R^5$ represents hydrogen or

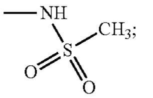

and each $R^6$ independently represents hydrogen or halogen.

2. The compound or pharmaceutically acceptable salt according to claim 1, wherein each $R^4$ represents a $C_{1-6}$ alkyl chain.

3. The compound or pharmaceutically acceptable salt according to claim 1, wherein $R^5$ represents

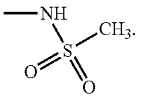

4. The compound or pharmaceutically acceptable salt according to claim 1, wherein each $R^6$ represents hydrogen.

5. The compound or pharmaceutically acceptable salt according to claim 1, wherein the compound is a compound of Formula (II):

Formula (II)

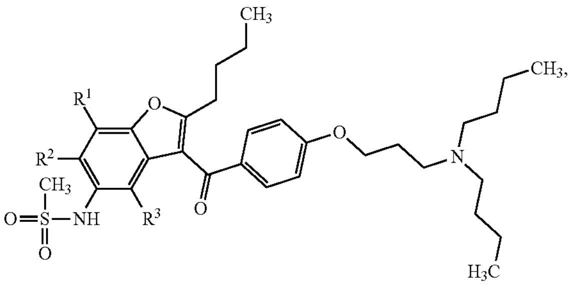

or the pharmaceutically acceptable salt is a pharmaceutically acceptable salt of Formula (II).

6. A pharmaceutical composition comprising the compound or pharmaceutically acceptable salt according to claim 1, and a pharmaceutically acceptable excipient or carrier.

7. A pharmaceutical composition comprising the compound or pharmaceutically acceptable salt according to claim 5, and a pharmaceutically acceptable excipient or carrier.

8. A method for treating a cardiac disease, the method comprising administering to a patient in need of such a treatment a therapeutically effective amount of the compound or pharmaceutically acceptable salt according to claim 1.

9. The method according to claim 8, wherein the cardiac disease is a cardiac arrhythmia.

10. The method according to claim 9, wherein the cardiac arrhythmia is atrial fibrillation.

11. A method for treating a cardiac disease, the method comprising administering to a patient in need of such a treatment a therapeutically effective amount of the compound or pharmaceutically acceptable salt according to claim 5.

12. A compound according to Formula (III) or a pharmaceutically acceptable salt thereof:

Formula (III)

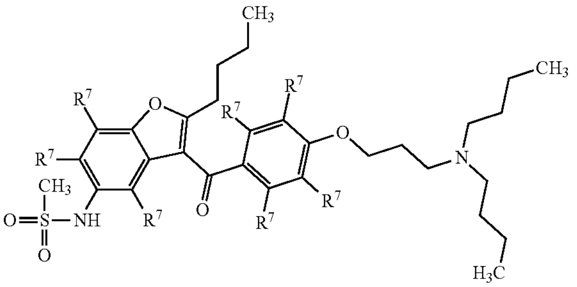

wherein each $R^7$ represents deuterium.

* * * * *

SEQUENCE LISTING

```
<160> NUMBER OF SEQ ID NOS: 14

<210> SEQ ID NO 1
<211> LENGTH: 19
<212> TYPE: RNA
<213> ORGANISM: Artificial Sequence
<220> FEATURE:
<223> OTHER INFORMATION: CYP2J2 siRNA1 (A-008208-13) target sequence

<400> SEQUENCE: 1

cucaggugua auauuguua                                               19
```

-continued

<210> SEQ ID NO 2
<211> LENGTH: 19
<212> TYPE: RNA
<213> ORGANISM: Artificial Sequence
<220> FEATURE:
<223> OTHER INFORMATION: CYP2J2 siRNA2 (A-008208-14) target sequence

<400> SEQUENCE: 2
gucacauacu uggaggcuu 19

<210> SEQ ID NO 3
<211> LENGTH: 19
<212> TYPE: RNA
<213> ORGANISM: Artificial Sequence
<220> FEATURE:
<223> OTHER INFORMATION: CYP2J2 siRNA3 (A-008208-15) target sequence

<400> SEQUENCE: 3
ccuggagguu cagcuguuu 19

<210> SEQ ID NO 4
<211> LENGTH: 19
<212> TYPE: RNA
<213> ORGANISM: Artificial Sequence
<220> FEATURE:
<223> OTHER INFORMATION: CYP2J2 siRNA4 (A-008208-16) target sequence

<400> SEQUENCE: 4
uggugagcuu uaagugguu 19

<210> SEQ ID NO 5
<211> LENGTH: 22
<212> TYPE: DNA
<213> ORGANISM: Artificial Sequence
<220> FEATURE:
<223> OTHER INFORMATION: CYP2J2 qPCR Primer Forward

<400> SEQUENCE: 5
gagcttagag gaacgcattc ag 22

<210> SEQ ID NO 6
<211> LENGTH: 22
<212> TYPE: DNA
<213> ORGANISM: Artificial Sequence
<220> FEATURE:
<223> OTHER INFORMATION: CYP2J2 qPCR Primer Reverse

<400> SEQUENCE: 6
gaaatgaggg tcaaaaggct gt 22

<210> SEQ ID NO 7
<211> LENGTH: 21
<212> TYPE: DNA
<213> ORGANISM: Artificial Sequence
<220> FEATURE:
<223> OTHER INFORMATION: beta-ACTIN qPCR Primer Forward

<400> SEQUENCE: 7
cccatcgagc atggtatcat c 21

<210> SEQ ID NO 8
<211> LENGTH: 22
<212> TYPE: DNA
<213> ORGANISM: Artificial Sequence
<220> FEATURE:
<223> OTHER INFORMATION: beta-ACTIN qPCR Primer Reverse -continued

<400> SEQUENCE: 8
agaagcatac agggatagca ct 22

<210> SEQ ID NO 9
<211> LENGTH: 22
<212> TYPE: DNA
<213> ORGANISM: Artificial Sequence
<220> FEATURE:
<223> OTHER INFORMATION: CYP2J2 PCR Primer Forward

<400> SEQUENCE: 9
gagcttagag gaacgcattc ag 22

<210> SEQ ID NO 10
<211> LENGTH: 22
<212> TYPE: DNA
<213> ORGANISM: Artificial Sequence
<220> FEATURE:
<223> OTHER INFORMATION: CYP2J2 PCR Primer Reverse

<400> SEQUENCE: 10
gaaatgaggg tcaaaaggct gt 22

<210> SEQ ID NO 11
<211> LENGTH: 21
<212> TYPE: DNA
<213> ORGANISM: Artificial Sequence
<220> FEATURE:
<223> OTHER INFORMATION: EPHX2 PCR Primer Forward

<400> SEQUENCE: 11
gacaaggcga tttcagccag a 21

<210> SEQ ID NO 12
<211> LENGTH: 21
<212> TYPE: DNA
<213> ORGANISM: Artificial Sequence
<220> FEATURE:
<223> OTHER INFORMATION: EPHX2 PCR Primer Reverse

<400> SEQUENCE: 12
ggttcaggtt tgaccattcc c 21

<210> SEQ ID NO 13
<211> LENGTH: 23
<212> TYPE: DNA
<213> ORGANISM: Artificial Sequence
<220> FEATURE:
<223> OTHER INFORMATION: GAPDH PCR Primer Forward

<400> SEQUENCE: 13
ggctgttgtc atacttctca tgg 23

<210> SEQ ID NO 14
<211> LENGTH: 23
<212> TYPE: DNA
<213> ORGANISM: Artificial Sequence
<220> FEATURE:
<223> OTHER INFORMATION: GAPDH PCR Primer Reverse

<400> SEQUENCE: 14
ggctgttgtc atacttctca tgg 23